(12) United States Patent
Kim et al.

(10) Patent No.: US 10,438,691 B2
(45) Date of Patent: Oct. 8, 2019

(54) NON-INVASIVE ASSESSMENT OF CHROMOSOME ALTERATIONS USING CHANGE IN SUBSEQUENCE MAPPABILITY

(71) Applicant: SEQUENOM, INC., San Diego, CA (US)

(72) Inventors: Sung Kim, Glendale, CA (US); Taylor Jacob Jensen, San Diego, CA (US); Mathias Ehrich, San Diego, CA (US)

(73) Assignee: SEQUENOM, INC., San Diego, CA (US)

( * ) Notice: Subject to any disclaimer, the term of this patent is extended or adjusted under 35 U.S.C. 154(b) by 503 days.

(21) Appl. No.: 15/026,939

(22) PCT Filed: Oct. 3, 2014

(86) PCT No.: PCT/US2014/059156
§ 371 (c)(1),
(2) Date: Apr. 1, 2016

(87) PCT Pub. No.: WO2015/054080
PCT Pub. Date: Apr. 16, 2015

(65) Prior Publication Data
US 2016/0292356 A1 Oct. 6, 2016

Related U.S. Application Data

(60) Provisional application No. 61/887,801, filed on Oct. 7, 2013.

(51) Int. Cl.
*G16B 30/00* (2019.01)
*G16B 20/00* (2019.01)

(52) U.S. Cl.
CPC ............. *G16B 30/00* (2019.02); *G16B 20/00* (2019.02)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,075,212 A | 12/1991 | Rotbart |
| 5,091,652 A | 2/1992 | Mathies et al. |
| 5,432,054 A | 7/1995 | Saunders et al. |
| 5,445,934 A | 8/1995 | Fodor |
| 5,670,325 A | 9/1997 | Lapidus et al. |
| 5,720,928 A | 2/1998 | Schwartz et al. |
| 5,786,146 A | 7/1998 | Herman et al. |
| 5,928,870 A | 7/1999 | Lapidus et al. |
| 5,939,598 A | 8/1999 | Kucherlapati et al. |
| 6,015,714 A | 6/2000 | Baldarelli et al. |
| 6,090,550 A | 7/2000 | Collinge et al. |
| 6,100,029 A | 8/2000 | Lapidus et al. |
| 6,214,558 B1 | 4/2001 | Shuber et al. |
| 6,214,560 B1 | 4/2001 | Yguerabide et al. |
| 6,235,475 B1 | 5/2001 | Brenner et al. |
| 6,258,540 B1 | 7/2001 | Lo et al. |
| 6,263,286 B1 | 7/2001 | Gilmanshin et al. |
| 6,403,311 B1 | 6/2002 | Chan |
| 6,566,101 B1 | 5/2003 | Shuber et al. |
| 6,617,133 B1 | 9/2003 | Deamer |
| 6,772,070 B2 | 8/2004 | Gilmanshin et al. |
| 6,818,395 B1 | 11/2004 | Quake et al. |
| 6,927,028 B2 | 8/2005 | Dennis et al. |
| 6,936,422 B2 | 8/2005 | Akeson et al. |
| 7,005,264 B2 | 2/2006 | Su et al. |
| 7,169,560 B2 | 1/2007 | Lapidus et al. |
| 7,279,337 B2 | 10/2007 | Zhu |
| 7,282,337 B1 | 10/2007 | Harris |
| 7,947,454 B2 | 5/2011 | Akeson et al. |
| 7,960,105 B2 | 6/2011 | Schwartz et al. |
| 7,972,858 B2 | 7/2011 | Meller et al. |
| 8,688,388 B2 | 4/2014 | Dzakula et al. |
| 2001/0014850 A1 | 8/2001 | Gilmanshin et al. |
| 2001/0049102 A1 | 12/2001 | Huang et al. |
| 2002/0006621 A1 | 1/2002 | Bianchi |
| 2002/0045176 A1 | 4/2002 | Lo et al. |
| 2002/0110818 A1 | 8/2002 | Chan |
| 2002/0119469 A1 | 8/2002 | Shuber et al. |
| 2002/0164629 A1 | 11/2002 | Quake et al. |
| 2003/0013101 A1 | 1/2003 | Balasubramanian |
| 2003/0082600 A1 | 5/2003 | Olek et al. |
| 2003/0180779 A1 | 9/2003 | Lofton-Day et al. |
| 2003/0207326 A1 | 11/2003 | Su et al. |
| 2003/0232346 A1 | 12/2003 | Su |

(Continued)

FOREIGN PATENT DOCUMENTS

| | | |
|---|---|---|
| CN | 101230403 A | 7/2008 |
| CN | 101316936 A | 12/2008 |

(Continued)

OTHER PUBLICATIONS

Talkowski, Michael E., et al. "Next-generation sequencing strategies enable routine detection of balanced chromosome rearrangements for clinical diagnostics and genetic research." The American Journal of Human Genetics 88.4 (2011): 469-481.*
Derrien et al., "Fast Computation and Applications of Genome Mappability", Plos One, vol. 7, No. 1, Jan. 2012, pp. e30377.
JP 2016-546892, "Office Action", dated Jul. 10, 2018, 7 pages.
Bergstrom et al. "Synthesis, Structure, and Deoxyribonucleic Acid Sequencing with a Universal Nucleoside: 1-(2'-Deoxy-.beta.-D-ribofuranosyl)-3-nitropyrrole," (1995) J. Am. Chem. Soc. 117, 1201-1209.

(Continued)

*Primary Examiner* — G Steven Vanni
(74) *Attorney, Agent, or Firm* — Kilpatrick Townsend & Stockton LLP

(57) ABSTRACT

Provided herein are methods, processes, systems, machines and apparatuses for non-invasive assessment of chromosome alterations.

20 Claims, 11 Drawing Sheets
Specification includes a Sequence Listing.

(56) References Cited

U.S. PATENT DOCUMENTS

| | | |
|---|---|---|
| 2004/0081993 A1 | 4/2004 | Cantor et al. |
| 2004/0110208 A1 | 6/2004 | Chan et al. |
| 2004/0137470 A1 | 7/2004 | Dhallan et al. |
| 2005/0019784 A1 | 1/2005 | Su et al. |
| 2005/0095599 A1 | 5/2005 | Pittaro et al. |
| 2005/0112590 A1 | 5/2005 | Boom et al. |
| 2005/0147980 A1 | 7/2005 | Berlin et al. |
| 2005/0164241 A1 | 7/2005 | Hahn et al. |
| 2005/0227278 A1 | 10/2005 | Wall |
| 2005/0287592 A1 | 12/2005 | Kless |
| 2006/0046258 A1 | 3/2006 | Lapidus et al. |
| 2006/0063171 A1 | 3/2006 | Akeson et al. |
| 2006/0068440 A1 | 3/2006 | Chan et al. |
| 2006/0141519 A1 | 6/2006 | Millonig et al. |
| 2006/0252071 A1 | 11/2006 | Lo et al. |
| 2007/0065823 A1 | 3/2007 | Dressman et al. |
| 2007/0202525 A1 | 8/2007 | Quake et al. |
| 2008/0020390 A1 | 1/2008 | Mitchell et al. |
| 2008/0070792 A1 | 3/2008 | Stoughton et al. |
| 2008/0081330 A1 | 4/2008 | Kahvejian et al. |
| 2008/0138809 A1 | 6/2008 | Kapur et al. |
| 2008/0187915 A1 | 8/2008 | Polonsky et al. |
| 2008/0233575 A1 | 9/2008 | Harris |
| 2008/0286793 A1 | 11/2008 | Nagaoka |
| 2009/0026082 A1 | 1/2009 | Rothberg et al. |
| 2009/0029377 A1 | 1/2009 | Lo et al. |
| 2009/0075252 A1 | 3/2009 | Harris |
| 2009/0129647 A1 | 5/2009 | Dimitrova et al. |
| 2009/0191565 A1 | 7/2009 | Lapidus et al. |
| 2009/0197257 A1 | 8/2009 | Harris |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0112575 A1 | 5/2010 | Fan et al. |
| 2010/0112590 A1 | 6/2010 | Lo et al. |
| 2010/0138165 A1 | 6/2010 | Fan et al. |
| 2010/0151471 A1 | 6/2010 | Faham et al. |
| 2010/0216151 A1 | 8/2010 | Lapidus et al. |
| 2010/0216153 A1 | 8/2010 | Lapidus et al. |
| 2010/0109197 A1 | 9/2010 | Stoddart et al. |
| 2010/0261285 A1 | 10/2010 | Goldstein et al. |
| 2010/0310421 A1 | 12/2010 | Oliver et al. |
| 2010/0330557 A1 | 12/2010 | Yakhini et al. |
| 2011/0086769 A1 | 4/2011 | Oliphant et al. |
| 2011/0159601 A1 | 6/2011 | Golovchenko et al. |
| 2011/0171634 A1 | 7/2011 | Xiao et al. |
| 2011/0174625 A1 | 7/2011 | Akeson et al. |
| 2011/0177498 A1 | 7/2011 | Clarke et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0288780 A1 | 11/2011 | Rabinowitz et al. |
| 2011/0294699 A1 | 12/2011 | Lee et al. |
| 2011/0312503 A1 | 12/2011 | Chuu et al. |
| 2011/0319272 A1 | 12/2011 | Fan et al. |
| 2012/0046877 A1 | 2/2012 | Hyland et al. |
| 2012/0122701 A1 | 5/2012 | Ryan et al. |
| 2012/0165203 A1 | 6/2012 | Quake et al. |
| 2012/0184449 A1 | 7/2012 | Hixson et al. |
| 2012/0192298 A1 | 7/2012 | Weinstein et al. |
| 2012/0214678 A1 | 8/2012 | Rava et al. |
| 2012/0264115 A1 | 10/2012 | Rava |
| 2012/0270212 A1 | 10/2012 | Rabinowitz et al. |
| 2012/0270739 A1 | 10/2012 | Rava et al. |
| 2013/0012399 A1 | 1/2013 | Meyers |
| 2013/0022977 A1 | 1/2013 | Lapidus et al. |
| 2013/0034546 A1 | 2/2013 | Rava et al. |
| 2013/0085681 A1 | 4/2013 | Deciu et al. |
| 2013/0096011 A1 | 4/2013 | Rava et al. |
| 2013/0130921 A1 | 5/2013 | Gao et al. |
| 2013/0130923 A1 | 5/2013 | Ehrich et al. |
| 2013/0150253 A1 | 6/2013 | Deciu et al. |
| 2013/0196317 A1 | 8/2013 | Lapidus et al. |
| 2013/0196859 A1 | 8/2013 | Van Eijk et al. |
| 2013/0237431 A1 | 9/2013 | Lo et al. |
| 2013/0245961 A1 | 9/2013 | Lo et al. |
| 2013/0261983 A1 | 10/2013 | Dzakula et al. |
| 2013/0288244 A1 | 10/2013 | Deciu et al. |
| 2013/0304392 A1 | 11/2013 | Deciu et al. |
| 2013/0309666 A1 | 11/2013 | Deciu et al. |
| 2013/0325360 A1 | 12/2013 | Deciu et al. |
| 2013/0338933 A1 | 12/2013 | Deciu et al. |
| 2014/0100792 A1 | 4/2014 | Deciu et al. |
| 2014/0180594 A1 | 6/2014 | Kim et al. |
| 2014/0229495 A1 | 8/2014 | Makkapati et al. |
| 2014/0235474 A1 | 8/2014 | Tang et al. |
| 2014/0242588 A1 | 8/2014 | Van Den Boom et al. |
| 2014/0322709 A1 | 10/2014 | Lapidus et al. |
| 2015/0005176 A1 | 1/2015 | Kim et al. |
| 2015/0100244 A1 | 4/2015 | Hannum |
| 2015/0347676 A1 | 12/2015 | Zhao et al. |
| 2016/0034640 A1 | 2/2016 | Zhao et al. |
| 2016/0110497 A1 | 4/2016 | Dzakula et al. |

FOREIGN PATENT DOCUMENTS

| | | |
|---|---|---|
| CN | 102272334 A | 12/2011 |
| CN | 102409088 A | 4/2012 |
| CN | 102858985 A | 1/2013 |
| CN | 103329138 A | 9/2013 |
| WO | 01/06001 A3 | 6/2002 |
| WO | 2013/086424 A1 | 6/2013 |

OTHER PUBLICATIONS

Bianchi et al., "Isolation of fetal DNA from nucleated erythrocytes in maternal blood," PNAS, 1990,87(9): 3279-3283.

Derrien et al. (2012) Fast Computation and Applications of Genome Mappability. PLoS One 7(1): e30377, doi:10.1371/journal.pone.0030377.

European Patent Application No. 14 709 656.2, Office Action dated Jul. 5, 2017.

Chen, E. Z. et al., "Noninvasive prenatal diagnosis of fetal trisomy 18 and trisomy 13 by maternal plasma DNA sequencing," Plos One 6(7):e21791, pp. 1-7 (2011).

CN 201480066990.7, "Office Action," dated Mar. 28, 2019, 12 pages.

EP 18193672.5, "Extended European Search Report," dated Mar. 1, 2019, 9 pages.

Jensen, T. J. et al., "High-throughput massively parallel sequencing for fetal aneuploidy detection from maternal plasma," Plos One 8(3):e57381, pp. 1-8 (2013).

Li, H. et al., "Mapping short DNA sequencing reads and calling variants using mapping quality scores," Genome Research 18:1851-1858 (2008).

* cited by examiner

Consensus Sequence Chr8:34880907 Chr11:44556834

*Event on CHR8*

CHR8          CAGATTGAGAGTCGATCCACAGACAGCCTAGCAGAGCAATCCAAGAGTAA
CHR8/CHR11    CAGATTGAGAGTCGATCCACAGACACAAGGGCGGGGCTGGGTTTTAGCCGTA
CHR11         ACAACTGGAGGATCTGGGCGCCTCGAGGGCGGGGCTGGGTTTTAGCCGTA

*Event on CHR11*

CHR11         ACAACTGGAGGATCTGGGCGCCTCGAGGGCGGGGCTGGGTTTTAGCCGTA
CHR11/CHR8    ACAACTGGAGGATCTGGGC----GCCTAGCAGACAGCCTAGCAGAGAGTAA
CHR8          CAGATTGAGAGTCGATCCACAGACAGCCTAGCAGAGCAATCCAAGAGTAA

FIG. 1C

NON-INVASIVE ASSESSMENT OF CHROMOSOME ALTERATIONS USING CHANGE IN SUBSEQUENCE MAPPABILITY

CROSS REFERENCE TO RELATED APPLICATIONS

This patent application is a U.S. national phase of International Application PCT/US2014/059156 filed Oct. 3, 2014, which claims priority to U.S. Provisional Application No. 61/887,801 filed on Oct. 7, 2013, each of which is incorporated herein by reference in it entirety for all purposes.

SEQUENCE LISTING

The instant application contains a Sequence Listing which has been submitted electronically in ASCII format and is hereby incorporated by reference in its entirety. Said ASCII copy, created on May 10, 2016, is named SEQ-6074-US.txt and is 919 bytes in size.

FIELD

Technology provided herein relates in part to methods, processes, machines and apparatuses for non-invasive assessment of chromosome alterations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Identifying one or more chromosome alterations can lead to diagnosis of, or determining predisposition to, a particular medical condition. Identifying a chromosome alteration can result in facilitating a medical decision and/or employing a helpful medical procedure. In certain embodiments, identification of one or more chromosome alterations involves the analysis of cell-free DNA. Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

The presence of fetal nucleic acid in maternal plasma allows for non-invasive prenatal diagnosis through the analysis of a maternal blood sample. For example, quantitative abnormalities of fetal DNA in maternal plasma can be associated with a number of pregnancy-associated disorders and genetic diseases associated with fetal chromosomal alterations. Hence, fetal nucleic acid analysis in maternal plasma can be a useful mechanism for the monitoring of feto-maternal well-being.

SUMMARY

Provided herein, in certain aspects, is a system comprising memory and one or more microprocessors, which memory comprises instructions and which one or more microprocessors are configured to perform, according to the instructions, a process for determining the presence or absence of one or more chromosome alterations in sample nucleic acid, which process comprises (a) characterizing mappability of a plurality of sequence read subsequences for sequence reads, where there are multiple sequence read subsequences for each sequence read, the sequence read subsequences for each sequence read are of different lengths, and the sequence reads are of the sample nucleic acid, (b) identifying a subset of sequence reads for which there is a change in mappability of one or more subsequences, (c) comparing (i) the number of each of the sequence reads in the subset identified in (b) from the sample, to (ii) the number of each of the sequence reads in the subset identified in (b) from a reference, thereby generating a comparison; and (d) determining the presence or absence of one or more chromosome alterations for the sample according to the comparison in (c).

Also provided herein, in certain aspects, is a method comprising memory and one or more microprocessors, which memory comprises instructions and which one or more microprocessors are configured to perform, according to the instructions, a process for determining the presence or absence of one or more chromosome alterations in sample nucleic acid, which process comprises (a) characterizing mappability of a plurality of sequence read subsequences for sequence reads, where there are multiple sequence read subsequences for each sequence read, the sequence read subsequences for each sequence read are of different lengths, and the sequence reads are of the sample nucleic acid, (b) identifying a subset of sequence reads for which there is a change in mappability of one or more subsequences, (c) comparing (i) the number of each of the sequence reads in the subset identified in (b) from the sample, to (ii) the number of each of the sequence reads in the subset identified in (b) from a reference, thereby generating a comparison; and (d) determining the presence or absence of one or more chromosome alterations for the sample according to the comparison in (c).

Also provided herein, in certain aspects, is a non-transitory computer-readable storage medium with an executable program stored thereon, which program is configured to instruct a microprocessor to (a) characterize mappability of a plurality of sequence read subsequences for sequence reads, where there are multiple sequence read subsequences for each sequence read, the sequence read subsequences for each sequence read are of different lengths, and the sequence reads are of the sample nucleic acid, (b) identify a subset of sequence reads for which there is a change in mappability of one or more subsequences, (c) compare (i) the number of each of the sequence reads in the subset identified in (b) from the sample, to (ii) the number of each of the sequence reads in the subset identified in (b) from a reference, thereby generating a comparison and (d) determine the presence or absence of one or more chromosome alterations for the sample according to the comparison in (c).

Certain aspects and embodiments of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A-C shows the identification of a fetal balanced translocation in maternal plasma. FIG. 1A shows a Circos plot (Krzywinski M. et al., (2009) Genome Res. 19:1639-45) detailing the identified fetal balanced translocation between chromosomes 8 and 11. The diagonal line represents the start and end of a sequenced fragment. The chromosome is highlighted to accentuate banding patterns and centromeres. FIG. 1B shows a Circos plot focused on the area of the identified translocation for each of the affected chromosomes. Repetitive regions within each of these regions are highlighted in black. Each line represents the start and end positions of a sequenced fragment. FIG. 1C shows a base level description of individual sequencing reads spanning the translocation breakpoint for each of the reciprocal translocation events. Sequences from chromosome 8 are indicated by "CHR8" (SEQ ID NO: 1) and are located to the right of the indicator. Sequences from chromosome 11 are indicated by "CHR11" (SEQ ID NO: 3) and are located to the right of the indicator. Vertical dashed lines indicate the chromosome breakpoint positions. The indicator "CHR8/CHR11" (SEQ ID NO: 2) shows chromosome 8 sequence to the left of the breakpoint position and chromosome 11 sequence to the right of the breakpoint position. The indicator "CHR11/CHR8" (SEQ ID NO: 4) shows chromosome 11 sequence to the left of the breakpoint position and chromosome 8 sequence to the right of the breakpoint position. Horizontal dashes indicated deleted nucleotides.

FIG. 2A-2D shows the overall mapping confidence of each sequence read subsequence (pseudo reads) for mate pair 1, (R1), and mate pair 2 (R2) where the breakpoint occurs at position 10 (FIG. 2A), 40 (FIG. 2B), 70 (FIG. 2C) or 120 (FIG. 2D) for a given target fragment length of about 140 bp. For R1, the mean MAPQ scores for pseudo read lengths from 32 to 100 bp are plotted as grey squares from the left most start position of the fragment. For R2, the mean MAPQ scores for pseudo read lengths from 32 to 100 bp are plotted as black squares in reverse order from the right most position of the fragment. FIG. 2C demonstrates the change in the average MAPQ as pseudo reads with high mappability become unmappable due to an increase in sequences derived from a different genomic region.

DETAILED DESCRIPTION

Figure 1A:
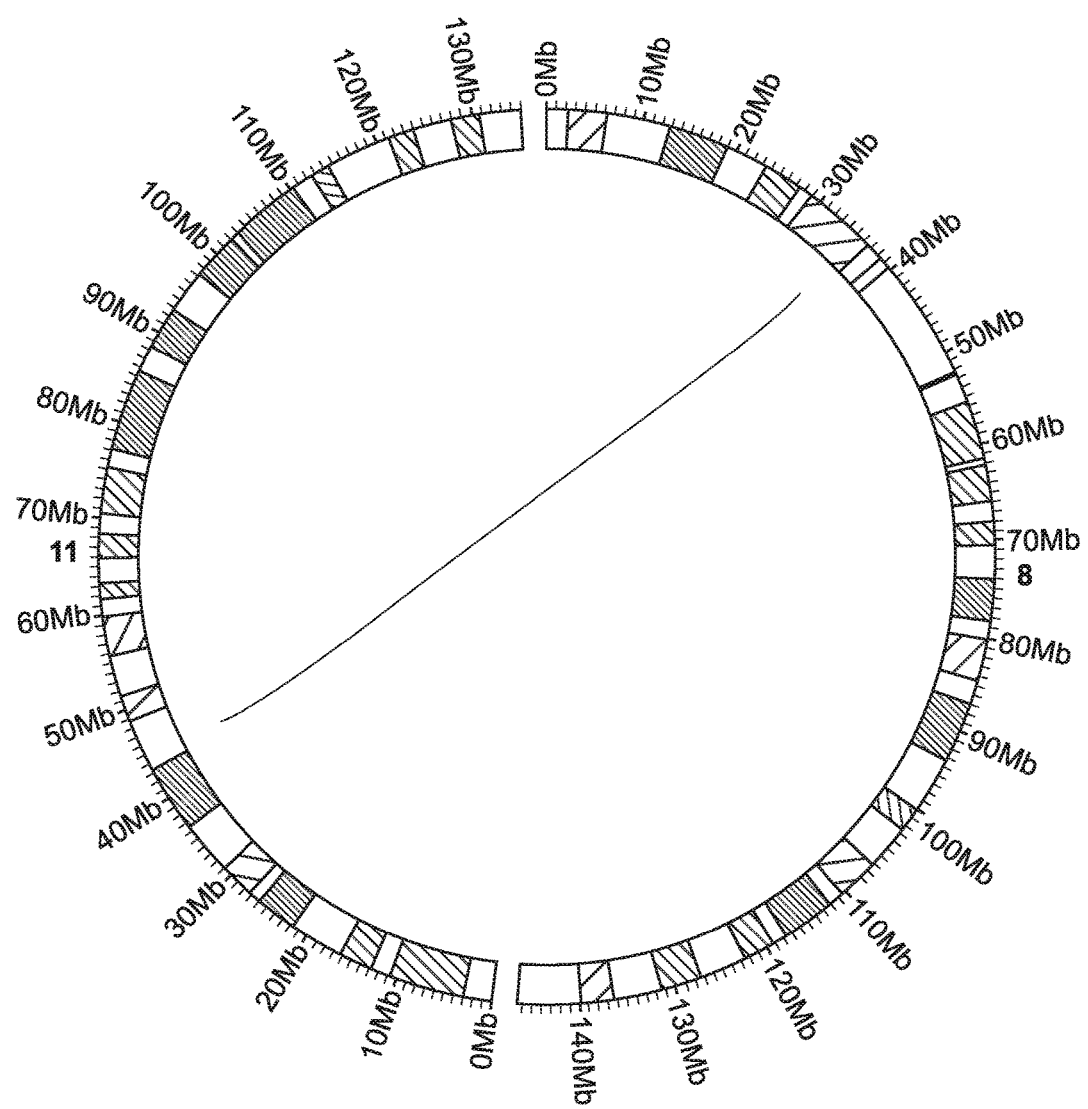

Provided herein are systems and methods for analyzing polynucleotides in a nucleic acid mixture which include, for example, methods for determining the presence or absence of a chromosome alteration (e.g., translocations, deletions, inversions, insertions). Chromosome alterations are widespread in a population and contribute to phenotypic variations within a population. Certain chromosome alterations can play a role in the onset and progression of various diseases (e.g., cancers), disorders (e.g., structural deformities, fertility disorders) and disabilities (e.g., mental disabilities). Systems, methods and products provided herein are useful for locating and/or identifying chromosome alterations and are useful for diagnosing and treating diseases, disorders and disabilities associated with certain chromosome alterations.

Next generation sequencing allows for sequencing nucleic acids on a genome-wide scale by methods that are faster and cheaper than traditional methods of sequencing. Methods, systems and products provided herein can utilize advanced sequencing technologies to locate and identify chromosome alterations and/or associated diseases and disorders. Methods, systems and products provided herein can often provide for a non-invasive assessment of a subjects genome (e.g., a fetal genome) using a blood sample, or part thereof, and are often safer, faster and/or less expensive than more invasive techniques (e.g., amniocentesis, biopsy). In some embodiments, provided herein are methods that comprise, in part, obtaining sequence reads (also referred to herein as "sequencing reads") nucleic acids present in a sample, which sequence reads often are mapped to a reference sequence, identifying certain mapping characteristics of selected subsets of sequence reads and determining the presence or absence of a chromosome alteration. Also provided herein are systems, machines, apparatuses, products and modules that, in some embodiments, carry out methods described herein.

Chromosome Alterations

Provided herein are methods and systems for identifying the presence or absence of one or more chromosome alterations. A "chromosome alteration" as used herein refers to any insertion, deletion (e.g., a loss), translocation, inversion, and/or fusion of genetic material in one or more human chromosomes. The term "genetic material" as used herein refers to one or more polynucleotides. A chromosome alteration can comprise, or is, an insertion, deletion and/or translocation of a polynucleotide of any length, non-limiting examples of which include polynucleotides of at least 10 bp, at least 20 bp, at least 50 bp, at least 100 bp, at least 500 bp, at least 1000 bp, at least 2500 bp, at least 5000 bp, at least 10,000 bp, at least 50,000 bp, at least 100,000 bp, least 500,000 bp, at least 1 mega base pairs (Mbp), at least 5 Mbp, at least 10 Mbp, at least 20 Mbp, at least 50 Mbp, at least 100 Mbp, and at least 150 Mbp. In some embodiments chromosome alterations comprise an insertion, deletion or translocation of a polynucleotide of about 10 bp to about 200 Mbp, about 20 bp to about 200 Mbp, about 50 bp to about 200 Mbp, about 100 bp to about 200 Mbp, about 500 bp to about 200 Mbp, about 1000 bp to about 200 Mbp, about 2500 bp to about 200 Mbp, about 5000 bp to about 200 Mbp, about 10,000 bp to about 200 Mbp, about 50,000 bp to about 200 Mbp, about 100,000 bp to about 200 Mbp, about 500,000 bp to about 200 Mbp, about 1 Mbp to about 200 Mbp, about 5 Mbp to about 200 Mbp, about 10 Mbp to about 200 Mbp, about 20 Mbp to about 200 Mbp, about 50 Mbp to about 200 Mbp, about 100 Mbp to about 200 Mbp, or about 150 Mbp to about 200 Mbp. In some embodiments chromosome alterations comprise an insertion, deletion and/or translocation of about 1% or more of a chromosome, about 2% or more of a chromosome, about 3% or more of a chromosome, about 4% or more of a chromosome, about 5% or more of a chromosome, about 10% or more of a chromosome, about 15% or more of a chromosome, about 20% or more of a chromosome, about 25% or more of a chromosome, or about 30% or more of a chromosome. Non-limiting examples of chromosome alterations that can be detected by a method and/or system described herein are described in greater detail herein and are presented in Table 1 (provided hereafter).

A chromosome alteration sometimes comprises or is an insertion, deletion and/or translocation of homologous genetic material. Homologous genetic material often comprises any suitable polynucleotide that is homologous to a human reference genome or a portion thereof. In some embodiments a chromosome alteration comprises an insertion, deletion and/or translocation of heterologous genetic material. "Heterologous genetic material" as used herein refers to genetic material originating from any non-human species. Heterologous genetic material sometimes comprises a polynucleotide that is highly homologous to the genome or a portion thereof, of any non-human species. An example of heterologous genetic material includes viral genomes, or portions thereof. Non-limiting examples of genera, families, groups and species of virus that may contribute heterologous genetic material include herpesviridae, adenoviridae, papovaviridae, anelloviridae, circoviridae, parvoviridae, reoviridae, alpharetrovirus, betaretrovirus, gammaretrovirus, deltaretrovirus, epsilonretrovirus, lentivirus, pumavirus, parvovirus, bornavirus, circoviruses, and polyoma virus.

In some embodiments a genetic alteration comprises or is a translocation. The term "translocation" as used herein refers to a chromosome mutation in which a segment of a chromosome changes positions. A translocation can be a nonreciprocal translocation or a reciprocal translocation. A nonreciprocal translocation comprises a transfer of genetic material from one segment of a genome, where the genetic material is deleted or copied, to another segment of a genome, where the genetic material is inserted. A reciprocal translocation comprises an exchange of genetic material from one segment of a genome with another segment of a genome. A translocation can occur within a chromosome (e.g., an intrachromosomal translocation) or between chromosomes (e.g., an interchromosomal translocation). A translocation can be a balanced translocation, where an exchange of genetic material does not involve a loss or gain of genetic material. For example, a balanced translocation is often an exchange of a segment x and a segment y where the length and integrity (e.g., sequence) of segment x and y is retained in the exchange, and no genetic material in addition to segment x and/or y is added or removed. In certain embodiments a balanced translocation is a nonreciprocal translocation where a segment of a genome is inserted and no additional genetic material, other than the insert, is added or removed at the site of insertion. In some embodiments one or both of the polynucleotides that are exchanged in a balanced translocation comprise one or more genetic variations (e.g., SNPs, microinsertions, microdeletion) as determined upon comparison with a reference genome. Such genetic variations often are located internal to a translocated polynucleotide (e.g., not at or near the breakpoints) and such genetic variations are often not a result of a translocation event. In some embodiments a translocation is an unbalanced translocation where an exchange of a segment x and a segment y comprises a loss of genetic material from x and/or y. In some embodiments of an unbalanced translocation comprises an exchange of a segment x and a segment y where genetic material is added to x and/or y (e.g., a duplication, an insertion). An unbalance translocation often comprises a gain or loss of genetic material at the ends of a translocated polynucleotide (e.g., at or near the breakpoints of either segment). The presence or absence of translocations and the position of translocation beak points can be determined by a method or system described herein. Determining the presence or absence of a translocation often comprises determining the presence or absence of genetic material (e.g., a polynucleotide) that has been inserted, deleted and/or exchanged. In some embodiments, the presence or absence of a translocation is determined by a method and/or system described herein.

In certain embodiments a translocation comprises or is an inversion. An inversion is sometimes referred to herein as a "chromosome inversion". In certain embodiments an inversion is where a segment of a chromosome is removed and rejoins with the same chromosome in an opposite orientation (e.g., relative to a 5'→3' DNA strand). In some embodiments of an inversion, a segment rejoins a chromosome at about the same site where it was removed. In certain embodiments of an inversion, a segment rejoins a chromosome at a different site from where it was removed. In certain embodiments genetic material is not lost or added when an inversion takes place, although sometimes there can be phenotypic consequences when an inversion breakpoint occurs within a gene or a region that controls gene expression. In some embodiments of an inversion, genetic material is lost or added and can be detected by methods described herein.

In some embodiments a chromosome alteration comprises or is an insertion. An insertion is sometimes referred to herein as a "chromosome insertion". An insertion is sometimes the addition of one or more nucleotide base pairs or a polynucleotide into a genome or segment thereof (e.g., a chromosome). In some embodiments an insertion refers to the insertion of a large sequence into a chromosome that often occurs due to unequal crossover during meiosis. An insertion sometimes refers to a translocation, or part thereof. For example, in a non-reciprocal translocation, a polynucleotide is deleted at one site (a deletion) and is inserted at another site (e.g., an insertions). In some embodiments an insertion is independent of a translocation (e.g., an insertion comprising insertion of viral DNA). In some embodiments an insertion is not a translocation. An insertion often accompanies a translocation. For example sometimes an insertion comprises additional genetic material that is added during an unbalanced translocation. A insertion that accompanies an unbalanced translocation is often added between a chromosome breakpoint and one or both ends of a translocated polynucleotide. A insertion that accompanies an unbalanced translocation is referred to herein as a "micro-insert". A micro-insert, or portion thereof, may comprise homologous genetic material and/or heterologous genetic material. In some embodiments, a micro-insert, or portion thereof, comprises nucleic acids or a polynucleotide of unknown origin and/or of unknown homology. Determining the presence or absence of an insertion often comprises determining the presence or absence of a micro-insert and/or a translocation (e.g., the presence of a translocated polynucleotide).

In some embodiments a micro-insert is from about 1 bp to about 10,000 bp, from about 1 bp to about 5000 bp, from about 1 bp to about 1000 bp, from about 1 bp to about 500 bp, from about 1 bp to about 250 bp, from about 1 bp to about 100 bp, from about 1 bp to about 50 bp, or from about 1 bp to about 30 bp. In some embodiments a polynucleotide insert is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 bp in length.

In some embodiments a chromosome alteration comprises or is a deletion. A deletion is sometimes referred to herein as a chromosome deletion. A deletion, as used herein, refers to the absence and/or loss of genetic material (e.g., one or more nucleotides, a polynucleotide sequence) that would be expected at a particular location (e.g., a site) or for a particular sequence of a genome according to a reference genome. In some embodiments a deletion refers to a loss of a contiguous strand of nucleic acids (e.g., a polynucleotide). In some embodiments a deletion results in the loss of genetic material from a genome. A deletion sometimes refers to a non-reciprocal translocation, or part thereof. For example, in a non-reciprocal translocation, a polynucleotide is deleted at one site (a deletion) and is inserted at another site. In some embodiments a deletion is not a translocation. Sometimes a deletion is independent of a translocation. A deletion often accompanies a translocation. For example sometimes a deletion comprises genetic material that is lost during an unbalanced translocation. Genetic material that is determined absent and/or lost due to a deletion that accompanies an unbalanced translocation is referred to herein as a micro-deletion. A micro-deletion that accompanies an unbalanced translocation can be lost from one or both ends of a translocated polynucleotide. In some embodiments a micro-deletion that accompanies an unbalanced translocation is lost from one or both ends of a site of insertion. A micro-deletion may comprise a loss of genetic material at one or both ends of a breakpoint. In some embodiments determining the presence of a micro-deletion often comprises determining the absence of genetic material and/or the presence of a translocation (e.g., the presence of a translocated polynucleotide).

In some embodiments a length of a micro-deletion is from about 1 bp to about 10,000 bp, from about 1 bp to about 5000 bp, from about 1 bp to about 1000 bp, from about 1 bp to about 500 bp, from about 1 bp to about 250 bp, from about 1 bp to about 100 bp, from about 1 bp to about 50 bp or from about 1 bp to about 30 bp. In some embodiments a micro-deletion comprises a loss of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 bp.

Samples

Provided herein are systems, methods and products for analyzing nucleic acids. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, cancer vs. non-cancer origin, tumor vs. non-tumor origin, sample origins, subject origins, and the like), or combinations thereof.

Nucleic acid or a nucleic acid mixture utilized in systems, methods and products described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, infant, child, adult).

Nucleic acid may be isolated from any type of suitable biological specimen or sample (e.g., a test sample). A sample or test sample can be any specimen that is isolated or obtained from a subject or part thereof (e.g., a human subject, a pregnant female, a fetus). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo; cancer biopsy), celocentesis sample, cells (blood cells, placental cells, embryo or fetal cells, fetal nucleated cells or fetal cellular remnants) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. In some embodiments, a biological sample may be blood and sometimes plasma or serum. The term "blood" as used herein refers to a blood sample or preparation from a pregnant woman or a woman being tested for possible pregnancy. The term encompasses whole blood, blood product or any fraction of blood, such as serum, plasma, buffy coat, or the like as conventionally defined. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain embodiments buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments, fetal cells or cancer cells may be included in the sample.

A sample can be a liquid sample. A liquid sample can comprise extracellular nucleic acid (e.g., circulating cell-free DNA). Non-limiting examples of liquid samples, include, blood or a blood product (e.g., serum, plasma, or the like), umbilical cord blood, amniotic fluid, cerebrospinal fluid, spinal fluid, lavage fluid (e.g., bronchoalveolar, gastric, peritoneal, ductal, ear, arthroscopic), biopsy sample (e.g., liquid biopsy for the detection of cancer), celocentesis sample, washings of female reproductive tract, urine, sputum, saliva, nasal mucous, prostate fluid, lavage, semen, lymphatic fluid, bile, tears, sweat, breast milk, breast fluid, the like or combinations thereof. In certain embodiments, a sample is a liquid biopsy, which generally refers to an assessment of a liquid sample from a subject for the presence, absence, progression or remission of a disease (e.g., cancer). A liquid biopsy can be used in conjunction with, or as an alternative to, a sold biopsy (e.g., tumor biopsy). In certain instances, extracellular nucleic acid is analyzed in a liquid biopsy.

A sample often is heterogeneous, by which is meant that more than one type of nucleic acid species is present in the sample. For example, heterogeneous nucleic acid can include, but is not limited to, (i) cancer and non-cancer nucleic acid, (ii) pathogen and host nucleic acid, (iii) fetal derived and maternal derived nucleic acid, and/or more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In certain embodiments a fluid or tissue sample is collected from a pregnant female during or just after (e.g., 0 to 72 hours after) giving birth (e.g., vaginal or non-vaginal birth (e.g., surgical delivery)).

Acquisition of Blood Samples and Extraction of DNA

In some embodiments methods herein comprise separating, enriching, sequencing and/or analyzing DNA found in the blood of a subject as a non-invasive means to detect the presence or absence of a chromosome alteration in a subject's genome and/or to monitor the health of a subject.

Acquisition of Blood Samples

A blood sample can be obtained from a subject (e.g., a male or female subject) of any age using a method of the present technology. A blood sample can be obtained from a pregnant woman at a gestational age suitable for testing using a method of the present technology. A suitable gestational age may vary depending on the disorder tested, as discussed below. Collection of blood from a subject (e.g., a pregnant woman) often is performed in accordance with the standard protocol hospitals or clinics generally follow. An appropriate amount of peripheral blood, e.g., typically between 5-50 ml, often is collected and may be stored according to standard procedure prior to further preparation. Blood samples may be collected, stored or transported in a manner that minimizes degradation or the quality of nucleic acid present in the sample.

Preparation of Blood Samples

An analysis of DNA found in a subjects blood may be performed using, e.g., whole blood, serum, or plasma. An analysis of fetal DNA found in maternal blood may be performed using, e.g., whole blood, serum, or plasma. Methods for preparing serum or plasma from blood obtained from a subject (e.g., a maternal subject) are known. For example, a subject's blood (e.g., a pregnant woman's blood) can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a subject. Combinations of more than one of these methods may also be used.

In some embodiments, a sample obtained from a pregnant female subject may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, virus, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons). Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

Nucleic Acid Isolation and Processing

Nucleic acid may be derived from one or more sources (e.g., cells, serum, plasma, buffy coat, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), the like or combinations thereof.

Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 µg/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid, "circulating cell-free nucleic acid" (e.g., CCF fragments, ccf DNA) and/or "cell-free circulating nucleic acid". Extracellular nucleic acid can be present in and obtained from blood (e.g., from the blood of a human, e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, small fragments of fetal nucleic acid (e.g., 30 to 500 bp fragments) can be purified, or partially purified, from a mixture comprising both fetal and maternal nucleic acid fragments. In certain examples, nucleosomes comprising smaller fragments of fetal nucleic acid can be purified from a mixture of larger nucleosome complexes comprising larger fragments of maternal nucleic acid. In certain examples, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid.

In some embodiments nucleic acids are sheared or cleaved prior to, during or after a method described herein. Sheared or cleaved nucleic acids may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Sheared or cleaved nucleic acids can be generated by a suitable method known in the art, and the average, mean or nominal length of the resulting nucleic acid fragments can be controlled by selecting an appropriate fragment-generating method.

In some embodiments nucleic acid is sheared or cleaved by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 20050112590, the like or combinations thereof.

As used herein, "shearing" or "cleavage" refers to a procedure or conditions in which a nucleic acid molecule, such as a nucleic acid template gene molecule or amplified product thereof, may be severed into two or more smaller nucleic acid molecules. Such shearing or cleavage can be sequence specific, base specific, or nonspecific, and can be accomplished by any of a variety of methods, reagents or conditions, including, for example, chemical, enzymatic, physical shearing (e.g., physical fragmentation). As used herein, "cleavage products", "cleaved products" or grammatical variants thereof, refers to nucleic acid molecules resultant from a shearing or cleavage of nucleic acids or amplified products thereof.

The term "amplified" as used herein refers to subjecting a target nucleic acid in a sample to a process that linearly or exponentially generates amplicon nucleic acids having the same or substantially the same nucleotide sequence as the target nucleic acid, or segment thereof. In certain embodiments the term "amplified" refers to a method that comprises a polymerase chain reaction (PCR). For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule).

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel). The term "specific cleavage agent" as used herein refers to an agent, sometimes a chemical or an enzyme that can cleave a nucleic acid at one or more specific sites.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a suitable sequence analysis.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Minority Vs. Majority Species

At least two different nucleic acid species can exist in different amounts in extracellular (e.g., circulating cell-free) nucleic acid and sometimes are referred to as minority species and majority species. In certain instances, a minority species of nucleic acid is from an affected cell type (e.g., cancer cell, wasting cell, cell attacked by immune system). In certain embodiments, a chromosome alteration is determined for a minority nucleic acid species. In certain embodiments, a chromosome alteration is determined for a majority nucleic acid species. As used herein, it is not intended that the terms "minority" or "majority" be rigidly defined in any respect. In one aspect, a nucleic acid that is considered "minority", for example, can have an abundance of at least about 0.1% of the total nucleic acid in a sample to less than 50% of the total nucleic acid in a sample. In some embodiments, a minority nucleic acid can have an abundance of at least about 1% of the total nucleic acid in a sample to about 40% of the total nucleic acid in a sample. In some embodiments, a minority nucleic acid can have an abundance of at least about 2% of the total nucleic acid in a sample to about 30% of the total nucleic acid in a sample. In some embodiments, a minority nucleic acid can have an abundance of at least about 3% of the total nucleic acid in a sample to about 25% of the total nucleic acid in a sample. For example, a minority nucleic acid can have an abundance of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total nucleic acid in a sample. In some instances, a minority species of extracellular nucleic acid sometimes is about 1% to about 40% of the overall nucleic acid (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40% of the nucleic acid is minority species nucleic acid). In some embodiments, the minority nucleic acid is extracellular DNA. In some embodiments, the minority nucleic acid is extracellular DNA from apoptotic tissue. In some embodiments, the minority nucleic acid is extracellular DNA from tissue affected by a cell proliferative disorder. In some embodiments, the minority nucleic acid is extracellular DNA from a tumor cell. In some embodiments, the minority nucleic acid is extracellular fetal DNA.

In another aspect, a nucleic acid that is considered "majority", for example, can have an abundance greater than 50% of the total nucleic acid in a sample to about 99.9% of the total nucleic acid in a sample. In some embodiments, a majority nucleic acid can have an abundance of at least about 60% of the total nucleic acid in a sample to about 99% of the total nucleic acid in a sample. In some embodiments, a majority nucleic acid can have an abundance of at least about 70% of the total nucleic acid in a sample to about 98% of the total nucleic acid in a sample. In some embodiments, a majority nucleic acid can have an abundance of at least about 75% of the total nucleic acid in a sample to about 97% of the total nucleic acid in a sample. For example, a majority nucleic acid can have an abundance of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the total nucleic acid in a sample. In some embodiments, the majority nucleic acid is extracellular DNA. In some embodiments, the majority nucleic acid is extracellular maternal DNA. In some embodiments, the majority nucleic acid is DNA from healthy tissue. In some embodiments, the majority nucleic acid is DNA from non-tumor cells.

In some embodiments, a minority species of extracellular nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of extracellular nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of extracellular nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of extracellular nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less).

Cell Types

As used herein, a "cell type" refers to a type of cell that can be distinguished from another type of cell. Extracellular nucleic acid can include nucleic acid from several different cell types. Non-limiting examples of cell types that can contribute nucleic acid to circulating cell-free nucleic acid include liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney/renal cells, heart cells, muscle cells, blood cells (e.g., white blood cells), central nervous system (CNS) cells, the like and combinations of the foregoing. In some embodiments, cell types that contribute nucleic acid to circulating cell-free nucleic acid analyzed include white blood cells, endothelial cells and hepatocyte liver cells. Different cell types can be screened as part of identifying and selecting nucleic acid loci for which a marker state is the same or substantially the same for a cell type in subjects having a medical condition and for the cell type in subjects not having the medical condition, as described in further detail herein.

A particular cell type sometimes remains the same or substantially the same in subjects having a medical condition and in subjects not having a medical condition. In a non-limiting example, the number of living or viable cells of a particular cell type may be reduced in a cell degenerative condition, and the living, viable cells are not modified, or are not modified significantly, in subjects having the medical condition.

A particular cell type sometimes is modified as part of a medical condition and has one or more different properties than in its original state. In a non-limiting example, a particular cell type may proliferate at a higher than normal rate, may transform into a cell having a different morphology, may transform into a cell that expresses one or more different cell surface markers and/or may become part of a tumor, as part of a cancer condition. In embodiments for which a particular cell type (i.e., a progenitor cell) is modified as part of a medical condition, the marker state for each of the one or more markers assayed often is the same or substantially the same for the particular cell type in subjects having the medical condition and for the particular cell type in subjects not having the medical condition. Thus, the term "cell type" sometimes pertains to a type of cell in subjects not having a medical condition, and to a modified version of the cell in subjects having the medical condition. In some embodiments, a "cell type" is a progenitor cell only and not a modified version arising from the progenitor cell. A "cell type" sometimes pertains to a progenitor cell and a modified cell arising from the progenitor cell. In such embodiments, a marker state for a marker analyzed often is the same or substantially the same for a cell type in subjects having a medical condition and for the cell type in subjects not having the medical condition.

In certain embodiments, a cell type is a cancer cell. Certain cancer cell types include, for example, leukemia cells (e.g., acute myeloid leukemia, acute lymphoblastic leukemia, chronic myeloid leukemia, chronic lymphoblastic leukemia); cancerous kidney/renal cells (e.g., renal cell cancer (clear cell, papillary type 1, papillary type 2, chromophobe, oncocytic, collecting duct), renal adenocarcinoma, hypernephroma, Wilm's tumor, transitional cell carcinoma); brain tumor cells (e.g., acoustic neuroma, astrocytoma (grade I: pilocytic astrocytoma, grade II: low-grade astrocytoma, grade III: anaplastic astrocytoma, grade IV: glioblastoma (GBM)), chordoma, cns lymphoma, craniopharyngioma, glioma (brain stem glioma, ependymoma, mixed glioma, optic nerve glioma, subependymoma), medulloblastoma, meningioma, metastatic brain tumors, oligodendroglioma, pituitary tumors, primitive neuroectodermal (PNET), schwannoma, juvenile pilocytic astrocytoma (JPA), pineal tumor, rhabdoid tumor).

Different cell types can be distinguished by any suitable characteristic, including without limitation, one or more different cell surface markers, one or more different morphological features, one or more different functions, one or more different protein (e.g., histone) modifications and one or more different nucleic acid markers. Non-limiting examples of nucleic acid markers include single-nucleotide polymorphisms (SNPs), methylation state of a nucleic acid locus, short tandem repeats, insertions (e.g., micro-insertions), deletions (micro-deletions) the like and combinations thereof. Non-limiting examples of protein (e.g., histone) modifications include acetylation, methylation, ubiquitylation, phosphorylation, sumoylation, the like and combinations thereof.

As used herein, the term a "related cell type" refers to a cell type having multiple characteristics in common with another cell type. In related cell types, 75% or more cell surface markers sometimes are common to the cell types (e.g., about 80%, 85%, 90% or 95% or more of cell surface markers are common to the related cell types).

Enrichment and Separation of Subpopulations of Nucleic Acid

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Methods herein sometimes comprise separating, enriching, and analyzing fetal DNA found in maternal blood as a non-invasive means to detect the presence or absence of a maternal and/or fetal chromosome alteration. Thus, in certain embodiments, methods of the technology comprise an additional step of enriching for a subpopulation of nucleic acid in a sample, such as, for example, fetal nucleic acid. In certain embodiments, a method for determining fetal fraction described herein also can be used to enrich for fetal nucleic acid. In certain embodiments, maternal nucleic acid is selectively removed (partially, substantially, almost completely or completely) from the sample. In certain embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In certain embodiments, a subset of nucleic acid fragments is selected prior to sequencing. In certain embodiments, hybridization-based techniques (e.g., using oligonucleotide arrays) can be used to first select for nucleic acid sequences from certain chromosomes (e.g., sex chromosomes and/or chromosome suspected of comprising a chromosome alteration. In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected set of nucleic acid fragments is sequenced randomly. In some embodiments, the nucleic acid is amplified prior to sequencing. In some embodiments, a portion or subset of the nucleic acid is amplified prior to sequencing.

Nucleic Acid Library

In some embodiments a nucleic acid library is a plurality of polynucleotide molecules (e.g., a sample of nucleic acids) that is prepared, assembled and/or modified for a specific process, non-limiting examples of which include immobilization on a solid phase (e.g., a solid support, e.g., a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigenin moiety and an anti-digoxigenin antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adaptors. In some embodiments a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments a polynucleotide of known sequence comprises a universal sequence. A universal sequence is a specific nucleotide acid sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using ccfDNA).

In certain embodiments, a ligation-based library preparation method is used. Non-limiting examples of ligation-based library preparation methods and kits include TRUSEQ or ScriptMiner, Illumina, San Diego Calif.; KAPA library preparation kits, KAPA Biosystems, Inc., Woburn, Mass.; NEBNext, New England Biolabs, Ipswich, Mass.; MuSeek, Thermo Fisher Scientific, Waltham, Mass.; NxSeq® DNA Sample Prep Kits, Lucigen Corp., Middleton, Wis.; PureGenome, EMD Millipore, Billerica, Mass. or the like). Ligation-based library preparation methods often make use of an adaptor design which can incorporate an index sequence at the initial ligation step and often can be used to prepare samples for single-read sequencing, paired-end sequencing and multiplexed sequencing. For example, sometimes nucleic acids (e.g., fragmented nucleic acids or ccfDNA) are end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing).

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, apparatus or machine, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus (e.g., a sequencing machine, e.g., a sequencer), the like and combinations thereof.

In some embodiments, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Sequencing

In some embodiments, nucleic acids (e.g., nucleic acid fragments, sample nucleic acid, cell-free nucleic acid) may be sequenced. In some embodiments, a full or substantially full sequence is obtained and sometimes a partial sequence is obtained. Sequencing, mapping and related analytical methods are described herein and are known in the art (e.g., United States Patent Application Publication US2009/0029377, incorporated by reference). Certain aspects of such processes are described hereafter.

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g. transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments MPS sequencing methods utilize a targeted approach, where sequence reads are generated from specific chromosomes, genes or regions of interest. Specific chromosomes, genes or regions of interest are sometimes referred to herein as targeted genomic regions. In certain embodiments a non-targeted approach is used where most or all nucleic acid fragments (e.g., ccf fragments, ccf DNA, polynucleotides) in a sample are sequenced, amplified and/or captured randomly.

MPS sequencing sometimes makes use of sequencing by synthesis and certain imaging processes. A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers).

Sequencing by synthesis, in some embodiments, comprises iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus or machine, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof. Other sequencing methods that may be used to conduct methods herein include digital PCR and sequencing by hybridization.

A suitable MPS method, system or technology platform for conducting methods described herein can be used to obtain nucleic acid sequencing reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, US patent publication no. US20130012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, and the like.

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number.

In certain embodiments, sequencing by hybridization can be used. The method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligonucleotide to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

In some embodiments, a sequence module obtains, generates, gathers, assembles, manipulates, transforms, processes, transforms and/or transfers sequence reads. A sequence module can determine the sequence of a nucleic acid utilizing a sequencing technology known in the art. In some embodiments a sequence module can align, assemble, fragment, complement, reverse complement, error check, or error correct sequence reads. In some embodiments a sequence module provides sequence reads to a mapping module or any other suitable module.

Sequencing Reads

As used herein, "reads" (i.e., "a read", "a sequence read") are short nucleotide sequences produced by any sequencing process described herein or known in the art. Reads can be generated from one end of a polynucleotide fragment ("single-end reads"), and sometimes are generated from both ends of a polynucleotide fragment (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length about 1000 bp or more.

Single end reads can be of any suitable length. In some embodiments the nominal, average, mean or absolute length of single-end reads sometimes is about 10 nucleotides to about 1000 contiguous nucleotides, about 10 nucleotide to about 500 contiguous nucleotides, about 10 nucleotide to about 250 contiguous nucleotides, about 10 nucleotide to about 200 contiguous nucleotides, about 10 nucleotide to about 150 contiguous nucleotides, about 15 contiguous nucleotides to about 100 contiguous nucleotides, about 20 contiguous nucleotides to about 75 contiguous nucleotides, or about 30 contiguous nucleotides or about 50 contiguous nucleotides. In certain embodiments the nominal, average, mean or absolute length of single-end reads is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 or more nucleotides in length.

Paired-end reads can be of any suitable length. In certain embodiments, both ends are sequenced at a suitable read length that is sufficient to map each read (e.g., reads of both ends of a fragment template) to a reference genome. In certain embodiments, the nominal, average, mean or absolute length of paired-end reads is about 10 contiguous nucleotides to about 100 contiguous nucleotides, about 10 contiguous nucleotides to about 75 contiguous nucleotides, about 10 contiguous nucleotides to about 50 contiguous nucleotides, about 15 contiguous nucleotides to about 50 contiguous nucleotides, about 15 contiguous nucleotides to about 40 contiguous nucleotides, about 15 contiguous nucleotides to about 30 contiguous nucleotides, or about 15 contiguous nucleotides to about 20 contiguous nucleotides. In certain embodiments, the nominal, average, mean or absolute length of paired-end reads is about 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80 or more nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads are often obtained from a nucleic acid sample from a pregnant female bearing a fetus. Sequence reads obtained from a nucleic acid sample from a pregnant female bearing a fetus are often sequence reads representative of the fetus and/or the mother of the fetus (e.g., a pregnant female subject).

Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a chromosome alteration, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

It has been observed that circulating cell free nucleic acid fragments (CCF fragments) obtained from a pregnant female generally comprise nucleic acid fragments originating from fetal cells (i.e., fetal fragments) and nucleic acid fragments originating from maternal cells (i.e., maternal fragments). Sequence reads derived from CCF fragments originating from a fetus are referred to herein as "fetal reads." Sequence reads derived from CCF fragments originating from the genome of a pregnant female (e.g., a mother) bearing a fetus are referred to herein as "maternal reads." CCF fragments from which fetal reads are obtained are referred to herein as fetal templates and CCF fragments from which maternal reads are obtained are referred herein to as maternal templates.

In some embodiments, a length of a polynucleotide fragment (e.g., a polynucleotide template) is determined. A length of a polynucleotide fragment or an average or mean length of polynucleotide fragments in a sample can be estimated and/or determined by a suitable method. In some embodiments a length of a polynucleotide fragment or an average or mean length of polynucleotide fragments in a sample is determined using a sequencing method. In some embodiments, fragment length is determined using a paired-end sequencing platform. Sometimes the length of a fragment template is determined by calculating the difference between genomic coordinates assigned to each mapped read of a paired-end read. In some embodiments, fragment length can be determined using a sequencing process whereby a complete, or substantially complete, nucleotide sequence is obtained for the fragment. Such sequencing processes include platforms that generate relatively long read lengths (e.g., Roche 454, Ion Torrent, single molecule (Pacific Biosciences), real-time SMRT technology, and the like).

In some embodiments, a subset of reads is selected for analysis and sometimes a certain portion of reads is removed from analysis. Selection of a subset of reads can, in certain instances, enrich for a species of nucleic acid (e.g., fetal nucleic acid). Enrichment of reads from fetal nucleic acid, for example, often increases the accuracy of a method described herein (e.g., detection of a chromosome alteration). However, selection and removal of reads from an analysis often decreases the accuracy of a method described herein (e.g., due to increased variance). Thus, without being limited by theory, there generally is a tradeoff between increased accuracy associated with fetal read enrichment and decreased accuracy associated with a reduced amount of reads in methods comprising selection and/or removal of reads (e.g., from fragments in a particular size range). In some embodiments, a method comprises selecting a subset of reads enriched for reads from fetal nucleic acid without significantly decreasing the accuracy of the method. Despite this apparent tradeoff, it has been determined, as described herein, that utilizing a subset of nucleotide sequence reads (e.g., reads from relatively short fragments), can improve or maintain the accuracy of fetal genetic analysis. For example, in certain embodiments, about 80% or more of nucleotide sequence reads can be discarded while maintaining sensitivity and specificity values that are similar to values for a comparable method that does not discard such nucleotide sequence reads.

In some embodiments some or all nucleic acids in a sample are enriched and/or amplified (e.g., non-specifically, e.g., by a PCR based method) prior to or during sequencing. In certain embodiments specific nucleic acid portions or subsets in a sample are enriched and/or amplified prior to or during sequencing. In some embodiments, a portion or subset of a pre-selected pool of nucleic acids is sequenced randomly. In some embodiments, nucleic acids in a sample are not enriched and/or amplified prior to or during sequencing.

In some embodiments a targeted enrichment, amplification and/or sequencing approach is used. A targeted approach often isolates, selects and/or enriches a subset of nucleic acids (e.g., targeted genomic regions) in a sample for further processing by use of sequence-specific oligonucleotides. In some embodiments, targeted genomic regions are associated with chromosome alterations including, but not limited to, translocations, insertions, additions, deletions, and/or inversions. In some embodiments, nucleic acid fragments from a plurality of targeted genomic regions are sequenced and/or assayed. Polynucleotides (e.g., ccf DNA) derived from any suitable chromosome, part thereof, or combination of chromosomes can be sequenced and/or analyzed by a targeted approach or a non-targeted approach using a method or system described herein. Non-limiting examples of chromosomes that can be analyzed by a method or system described herein includes chromosomes 1, 2, 3, 4, 5, 6, 7, 8, 9, 10, 11, 12, 13, 14, 15, 16, 17, 18, 19, 20, 21, 22, X and Y. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.01-fold to about 100-fold coverage, about 0.2-fold to 20-fold coverage, or about 0.2-fold to about 1-fold coverage (e.g., about 0.02-, 0.03-, 0.04-, 0.05-, 0.06-, 0.07-, 0.08, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In some embodiments, sequence coverage is reduced without significantly resulting in a decrease the accuracy (e.g., sensitivity and/or specificity) of a method described herein. A significant decrease in accuracy can be a decrease in accuracy of about 1% to about 20% compared to a method that does not use a reduced sequence read count. For example, a significant decrease in accuracy can be about a 2%, 3%, 4%, 5%, 6%, 7%, 8%, 9%, 10%, 15% or more decrease. In some embodiments, sequence coverage and/or sequence read count is reduced by about 50% or more. For example, sequence coverage and/or sequence read count can be reduced by about 55%, 60%, 65%, 70%, 75%, 80%, 85%, 90%, 95% or more. In some embodiments, sequence coverage and/or sequence read count is reduced by about 60% to about 85%. For example, sequence coverage and/or sequence read count can be reduced by about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83% or 84%. In some embodiments, sequence coverage and/or sequence read count can be reduced by removing certain sequence reads. In some instances, sequence reads from fragments longer than a particular length (e.g., fragments longer than about 160 bases) are removed.

In some embodiments, one or more samples are sequenced in a sequencing run. Nucleic acids from different samples are often identified by one or more unique identifiers or identification tags. A sequencing method often utilizes identifiers that allow multiplexing of sequence reactions in a sequencing process. A sequencing process can be performed using any suitable number of samples and/or unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane are dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Mapping Reads

Sequence reads, or parts thereof (e.g., sequence read subsequences), can be mapped and/or aligned to a reference sequence (e.g., a reference genome) by a suitable method. The process of aligning one or more reads to a reference genome is referred to herein as "mapping". Sometimes the number of sequence reads mapping to a specified nucleic acid region (e.g., a chromosome, portion or segment thereof) can be quantitated. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped", "a mapped sequence read" or "a mapped read".

As used herein, the terms "aligned", "alignment", or "aligning" refer to two or more nucleic acid sequences that can be identified as a match (e.g., 100% identity) or partial match. Alignments can be done manually (e.g., by visual inspection) or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads, or parts thereof, can be aligned with sequences in a reference genome. In some embodiments, sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database.

In some embodiments, a read may uniquely or non-uniquely map to a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. removed by a filter method). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, or portion thereof, whether partial or complete, of any organism or virus which may be used to reference identified sequences from a subject. For example, a reference genome of human subjects, bacteria, parasites, viruses, and many other organisms can be found at the National Center for Biotechnology Information at world wide web uniform resource locator: ncbi.nlm.nih.gov. In some embodiments a reference genome is obtained from a reference sample, or a set of reference samples. A "genome" refers to the complete genetic information of an organism or virus, expressed in nucleic acid sequences. A "reference sequence" as used herein can refer to a reference genome, or a portion thereof (e.g., a chromosome, a gene, a conserved region, a region of high mappability). A reference sequence is sometimes a reference genome or portion thereof. As used herein, a reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes. In some embodiments, a reference genome is a virus genome, or portion thereof. In some embodiments a reference genome of one or more viruses is used to align and/or map nucleic acids (e.g., sequence reads) obtained from a human subject (e.g., a human sample).

In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

Sequence reads can be mapped by a mapping module or by a machine comprising a mapping module, which mapping module generally maps reads to a reference genome or segment thereof. A mapping module can map sequencing reads by a suitable method known in the art or described herein. In some embodiments, a mapping module or a machine comprising a mapping module is required to provide mapped sequence reads. A mapping module often comprises a suitable mapping and/or alignment program or algorithm.

Discordant Reads

Presented herein are methods of determining the presence or absence of chromosome alterations and, in some embodiments, methods of identifying breakpoints associated with chromosome alterations. In certain embodiments, a method of identifying breakpoints and/or chromosome alterations comprises identifying sequence reads that are discordant. In some embodiments a method comprises identifying a condition of discordancy for a sequence, a sequencing read and/or a pair of sequencing reads (e.g., a pair of read mates). The term "discordancy" as used herein refers to a condition where (i) a first read, or portion thereof, maps to a first location of a reference genome and (ii) a second read, a portion thereof, or a second portion of a first read is unmappable, comprises a low mappability score, and/or maps to a second location of a reference genome where the first and second locations of the reference genome are non-contiguous and/or, separated by a distance longer than the size of a template polynucleotide fragment from which one or more of the sequence reads were obtained. In some embodiments discordancy refers to a condition where both reads of a pair of sequencing reads (e.g., a pair of read mates) are unmappable. Discordant sequence reads and/or discordant pairs of sequence reads often comprise discordancy. Discordancy can be determined for a polynucleotide sequence, a sequence read, a single-end read, and double-end reads (e.g., paired-end reads). In some embodiments a method comprises identifying discordant reads and/or discordant read pairs. Discordant reads and/or discordant read pairs can be identified using any suitable sequencing method. In some embodiments discordant read pairs are identified from paired-end sequencing reads. The terms "paired-end sequencing reads" and "paired-end reads" are used synonymously herein and refer to a pair of sequencing reads where each member of the pair is derived from sequencing complementary strands of a polynucleotide fragment. Each read of a paired-end read is referred to herein as a "read mate".

Sequence reads and/or paired-end reads are often mapped to a reference genome by use of a suitable mapping and/or alignment program non-limiting examples of which include BWA (Li H. and Durbin R. (2009) *Bioinformatics* 25, 1754-60), Novoalign [Novocraft (2010)], Bowtie (Langmead B, et al., (2009) *Genome Biol.* 10:R25), SOAP2 (Li R, et al., (2009) *Bioinformatics* 25, 1966-67), BFAST (Homer N, et al., (2009) *PLoS ONE* 4, e7767), GASSST (Rizk, G. and Lavenier, D. (2010) *Bioinformatics* 26, 2534-2540), and MPscan (Rivals E., et al. (2009) *Lecture Notes in Computer Science* 5724, 246-260), or the like. Sequence reads and/or paired-end reads can be mapped and/or aligned using a suitable short read alignment program. Non-limiting examples of short read alignment programs are BarraCUDA, BFAST, BLASTN, BLAT, Bowtie, BWA, CASHX, CUDA-EC, CUSHAW, CUSHAW2, drFAST, ELAND, ERNE, GNUMAP, GEM, GensearchNGS, GMAP, Geneious Assembler, iSAAC, LAST, MAQ, mrFAST, mrsFAST, MOSAIK, MPscan, Novoalign, NovoalignCS, Novocraft, NextGENe, Omixon, PALMapper, Partek, PASS, PerM, QPalma, RazerS, REAL, cREAL, RMAP, rNA, RTG, Segemehl, SeqMap, Shrec, SHRiMP, SLIDER, SOAP, SOAP2, SOAP3, SOCS, SSAHA, SSAHA2, Stampy, SToRM, Subread, Subjunc, Taipan, UGENE, VelociMapper, TimeLogic, XpressAlign, ZOOM, the like or combinations thereof. Paired-end reads are often mapped to opposing ends of the same polynucleotide fragment, according to a reference genome. In some embodiments sequence reads are mapped independently. In some embodiments, read mates are mapped independently. In some embodiments, information from both sequence reads (i.e., from each end) is factored in the mapping process. A reference genome is often used to determined and/or infer the sequence of nucleic acids located between paired-end read mates. The term "discordant read pairs" as used herein refers to a paired-end read comprising a pair of read mates, where one or both read mates fail to unambiguously map to the same region of a reference genome defined, in part, by a segment of contiguous nucleotides. In some embodiments discordant read pairs are paired-end read mates that map to unexpected locations of a reference genome. Non-limiting examples of unexpected locations of a reference genome include (i) two different chromosomes, (ii) locations separated by more than a predetermined fragment size (e.g., more than 300 bp, more than 500 bp, more than 1000 bp, more than 5000 bp, or more than 10,000 bp), (iii) an orientation inconsistent with a reference sequence (e.g., opposite orientations), the like or a combination thereof. In some embodiments read mates that map and/or align to two different chromosomes are identified as discordant read mates. Read mates that map and/or align to two different chromosomes are referred to herein as "chimeric read pairs". In some embodiments a discordant read pair does not comprise a pair of read mates where a first read mate maps to a first chromosome and a second read mate maps to a second chromosome and where the first chromosome is a different chromosome than the second chromosome. In some embodiments a discordant read pair comprises a first read mate that maps to a first segment of a reference genome (e.g., a first chromosome) and a second read mate that partially maps to a first segment of a reference genome (e.g., a first chromosome). The term "partially" as used in the term "partially maps" as used herein refers to 90% or less, 80% or less, 60% or less, 50% or less, 40% or less, 30% or less, 25% or less, 20% or less, 15% or less, 10% or less or 5% or less of the nucleotides of a read. In some embodiments a discordant read pair comprises a first read mate that maps to a first segment of a reference genome (e.g., a first chromosome) and a second read mate that is unmappable and/or comprises low mappability (e.g., a low mappability score). In some embodiments a discordant read pair comprises a first read mate that maps to a first segment of a reference genome (e.g., a first chromosome) and a second read mate, where the mappability of the second read mate, or a portion thereof, is not determined. In some embodiments a discordant read pair comprises a first read mate that maps to a first segment of a reference genome (e.g., a first chromosome) and a second read mate that partially maps to a second segment of a reference genome (e.g., a second chromosome), where the first segment and the second segment are different segments (e.g., different chromosomes). In some embodiments a subset (e.g., a collection) of discordant read pairs comprises first and second read mates that maps to different chromosome and first and second read mates where one or both read mates are unmappable and/or partially map to the same or different chromosomes. In some embodiments discordant read mates are identified according to a length (e.g., an average length, a predetermined fragment size) or expected length of template polynucleotide fragments in a sample. For example, read mates that map to a location that is separated by more than the average length or expected length of polynucleotide fragments in a sample are sometimes identified as discordant read pairs. Read pairs that map in opposite orientation are sometimes determined by taking the reverse complement of one of the reads and comparing the alignment of both reads using the same strand of a reference sequence. Discordant read pairs can be identified by any suitable method and/or algorithm known in the art or described herein. Discordant read pairs can be identified by a discordant read identifying module or by a machine comprising a discordant read identifying module, which discordant read identifying module generally identifies discordant read pairs. Non-limiting examples of discordant read identifying modules include SVDetect, Lumpy, BreakDancer, BreakDancerMax, CREST, DELLY, the like or combinations thereof. In some embodiments discordant read pairs are not identified by an algorithm that identifies only read mates that map or align to different chromosomes. In certain embodiments discordant read pairs are identified by an algorithm that identifies a collection comprising paired-end read mates that map or align to different chromosomes and paired-end read mates, where one or both read mates are unmappable and/or partially map to the same or different chromosomes. In some embodiments, a discordant read identifying module or a machine comprising a discordant read identifying module is required to provide discordant read pairs.

In some embodiments discordant read pairs are not clustered or subjected to a clustering analysis. A clustering analysis, as referred to herein, means a process of grouping paired-end reads according to the mapped location of one or both read mates within a genome. In some embodiments a clustering analysis comprises generating a subset of paired reads where one read mate of each read pair maps to a first chromosome and the other read mate of each read pair maps to a second chromosome, where the first chromosome is a different chromosome than the second chromosome.

The term "discordant read" as used herein refers to a sequence read where a first portion of a read fails to unambiguously map to the same region of a reference genome as a second portion of a read, where the same region of a reference genome is defined, in part, as a segment of contiguous nucleotides. In some embodiments a discordant read comprises a first portion and a second portion that map to unexpected locations of a reference genome. In some embodiments a discordant read comprises a first portion that maps to a first chromosome and a second portion that maps to a second chromosome, where the first chromosome is a different chromosome than the second chromosome. In some embodiments a discordant read comprises a portion that partially maps to a first segment of a reference genome (e.g., a first chromosome). In some embodiments a discordant read comprises a first portion that maps to a first segment of a reference genome (e.g., a first chromosome) and a second portion that is unmappable and/or comprises low mappability (e.g., a low mappability score). In some embodiments a discordant read comprises a first portion that maps to a first segment of a reference genome (e.g., a first chromosome) and a second portion, where the mappability of the second portion, or a part thereof, is not determined. In some embodiments a discordant read comprises a first portion that maps to a first segment of a reference genome (e.g., a first chromosome) and a second portion that partially maps to a second segment of a reference genome (e.g., a second chromosome), where the first segment and the second segment are different segments (e.g., different chromosomes). Discordant reads can be identified by a suitable method and/or algorithm known in the art or described herein. Discordant reads are sometimes identified by a process of characterizing a read. Discordant reads can be identified by a discordant read identifying module or by a machine comprising a discordant read identifying module, which discordant read identifying module generally identifies discordant reads. In certain embodiments discordant reads are identified by an algorithm that identifies a subset or collection of discordant reads. In some embodiments, a discordant read identifying module or a machine comprising a discordant read identifying module is required to provide discordant reads.

Change in Mappability

In some embodiments the mappability of one or more reads is characterized. In some embodiments characterizing the mappability of reads comprises characterizing the mappability of a plurality of sequence read subsequences. The term "characterizing the mappability of a plurality of sequence read subsequences of a read" is sometimes referred to herein as "characterizing a read". Characterizing a read sometimes comprises generating a plurality of sequence read subsequences of a read and mapping each of the sequence read subsequences to a reference genome. In some embodiments sequence read subsequences are generated for both read mates of a discordant read pair. Sequence read subsequences are sometimes referred to herein as pseudo reads. Sequence read subsequences can be generated by any suitable method. Sequence read subsequences are often generated by an in silico process. In some embodiments sequence read subsequences are generated and mapped by the following method: (i) mapping a read, (ii) removing, by an in silico process, one or more bases from the end of the mapped read, (iii) mapping the resulting shortened reads (i.e., sequence read subsequences), and (v) repeating (ii) and (iii). In some embodiments steps (ii) and (iii) are repeated until the end of the read is reached. In certain embodiments steps (ii) and (iii) are repeated until a resulting, shortened read is no longer mappable. Sequence read subsequences can be generated by progressively and/or incrementally removing one or more bases from the 3' end of a read or from the 5' end of a read. Sequence read subsequences can be generated by removing bases from the end of a read (e.g., in step (ii)) one at a time, two at a time, three at a time, four at a time, five at time or by a combination thereof. In some embodiments each sequence read subsequence that is generated for a read is of a different length. In some embodiments each sequence read subsequence for a read is a subsequence of contiguous nucleotides from a read. In some embodiments each of the sequence read subsequences of a read is shorter than the full length read and sometimes the largest sequence read subsequence is shorter than the read by about 1 base, by about 2 bases or less, by about 3 bases or less, by about 4 bases or less, by about 5 bases or less, by about 6 bases or less, by about 7 bases or less, by about 8 bases or less, by about 9 bases or less, or by about 10 bases or less. In some embodiments each of the sequence read subsequences of a read is shorter than the next largest sequence read subsequence or the read by about 1 base, by about 2 bases or less, by about 3 bases or less, by about 4 bases or less, by about 5 bases or less, by about 6 bases or less, by about 7 bases or less, by about 8 bases or less, by about 9 bases or less, or by about 10 bases or less. In some embodiments sequence read subsequences of each discordant read mate is incrementally shorter than the next largest subsequence or the read mate by about 1 base, by about 2 bases or less, by about 3 bases or less, by about 4 bases or less, by about 5 bases or less, by about 6 bases or less, by about 7 bases or less, by about 8 bases or less, by about 9 bases or less, by about 10 bases or less, or combination thereof. The term "sequence read subsequences" as used herein refers to a set of in silico generated polynucleotide fragments generated for a read by a method described herein. The term "sequence read subsequences" as used herein can also refer to one or more sets of in silico generated polynucleotide fragments generated for one or more reads. The term "sequence read subsequences" as used herein also refers to and/or comprises a full-length read from which a set of sequence read subsequences were generated. Sequence read subsequences are sometimes referred to herein as "subsequences". The term "sequence read subsequence" and/or "subsequence" as used herein in a singular tense, refers to a member of set of in silico generated polynucleotide fragments generated for a read.

Sequence read subsequences can be generated by a suitable module, program or method. In certain embodiments, sequence read subsequences are generated by a fragmentation module. Sequence read subsequences can be mapped by a suitable mapping module, program or method, non-limiting examples of which include BWA (Li H. and Durbin R. (2009) *Bioinformatics* 25, 1754-60), Novoalign [Novocraft (2010)], Bowtie (Langmead B, et al., (2009) *Genome Biol.* 10:R25)., SOAP2 (Li R, et al., (2009) *Bioinformatics* 25, 1966-67), BFAST (Homer N, et al., (2009) *PLoS ONE* 4, e7767), GASSST (Rizk, G. and Lavenier, D. (2010) *Bioinformatics* 26, 2534-2540), and MPscan (Rivals E., et al. (2009) *Lecture Notes in Computer Science* 5724, 246-260), or the like.

In some embodiments some or all sequence read subsequences generated for a sample are mapped to a reference genome. In some embodiments sequence read subsequences of a read are mapped to a combination of one or more reference genomes. Subsequences of one or more reads are often mapped to a human reference genome. In some embodiments subsequences are mapped to a human genome and/or a viral genome. In some embodiments the mappability of some or all sequence read subsequences of a read are determined. The term "mappability" refers to a measure of how well a polynucleotide fragment maps to a reference genome. Sometimes a mappability comprises a mappability score or value. Sometimes a mappability score or value is determined for each sequence read subsequence of a read (e.g., a read mate). Any suitable mappability score or value can be determined for a sequence read subsequence. A mappability score can be any suitable score generated by a mapping module, program or method known or described herein, the like or combinations thereof. For example, in some embodiments a mappability score can be a MAPQ score. In some embodiments a mappability score comprises an alignment score. For example an alignment score can be generated by a suitable local alignment algorithm (e.g., such as Smith-Waterman Algorithm) or an alignment score can be generated according to a euclidean distance between two sequences weighted by the number of occurrences in a reference genome. An alignment score can be generated by any suitable metric that qualifies or quantitates the uniqueness of a polynucleotide sequence. Standards for determining a high, good, acceptable, low, non-acceptable, and/or a poor mappability score are known in the art and are often specific to the mapping or alignment program that is used.

In some embodiments determining the presence or absence of a chromosome alteration comprises determining and/or identifying a change in mappability of sequence read subsequences of a read (e.g., a discordant read, a read mate of a discordant read pair). In some embodiments characterizing a read comprises determining and/or identifying a change in mappability of sequence read subsequences of a read. A change in mappability is sometimes determined between one or more sequence read subsequences. For example, sometimes a change in mappability is indicated where one or more subsequences comprising one or more nucleotides positioned on a first side of a read comprise a first subset of mappability scores that are substantially the same or similar, and one or more subsequences comprising nucleotides on a second side of a read comprise a second subset of mappability scores that are substantially different than the first subset. A change in mappability identified in sequence read subsequences of a read is sometimes referred to herein as a change in mappability of a read. For example, a read can comprise a change in mappability where sequence read subsequences of the read comprise a change in mappability. In certain embodiments, discordancy can be identified in a read where a change in mappability is determined for the read. In certain embodiments, a discordant read comprises a change in mappability. In some embodiments, a change in mappability can be determined for a read for which discordancy is identified. In some embodiments a change in mappability is not identified and/or determined for a read and the read does not comprise discordancy. Sometimes one or both read mates of a discordant read pair comprise a change in mappability. In certain embodiments a discordant read pair is identified where one or both read mates of a pair of paired-end reads comprise a change in mappability. In some embodiments, a change in mappability can be determined for one or both read mates of a discordant read pair. In some embodiments, one or both read mates of a chimeric read pair do not comprise a change in mappability.

Sometimes determining and/or identifying a change in mappability of sequence read subsequences of a read comprises determining a relationship between the mappability of each sequence read subsequence of a read and a suitable feature of each sequence read subsequence of a read (e.g., a discordant read, a discordant read pair, a read mate of a discordant read pair). A relationship can be determined for one or more reads. For example, in some embodiments a relationship is determined for both read mates of a discordant read pair.

The term "relationship" as use herein refers to a mathematical and/or a graphical relationship between two or more variables or values. Non-limiting examples of a relationship include a mathematical or graphical representation of a function, a correlation, a distribution, a linear or non-linear equation, a line, a regression, a fitted regression, the like or a combination thereof. In some embodiments, determining a relationship comprises generating a linear, non-linear or fitted relationship. In some embodiments a relationship is plotted or graphed.

Non-limiting examples of a suitable feature of a sequence read subsequence that can be used for determining a relationship include a fragment length, an identifier of each fragment indicating its relative order, a molecular weight, a GC content, the like or a combination thereof. In certain embodiments determining and/or identifying a change in mappability of sequence read subsequences of a read comprises determining a relationship between the mappability and a length of each sequence read subsequence of a read (e.g., one or both read mates).

In some embodiments determining and/or identifying a change in mappability comprises determining a presence or absence of a change in one or more coefficients, variables, values, constants, the like, or a combination thereof that describe and/or quantifies a relationship. A "change" as used herein sometimes refers to "a difference". Non limiting examples of coefficients, constants, values and variables that can be used to determine a change in mappability include slope (e.g., a slope of a linear, non-linear or fitted relationship), a sum, average, median or mean of a coordinate (e.g., an x-coordinate or y-coordinate value), an intercept (e.g., a y-intercept), a maximum value (e.g., a maximum peak height), a minimum value (e.g., lowest value), an integral of a curve (e.g., an area under the curve), the like or combinations thereof. In some embodiments a change in mappability is determined mathematically. A change can be determined by a suitable statistical test of significance (e.g., significant difference), non-limiting examples of which include a Wilcoxon test (e.g., a Wilcoxon signed rank), a t-test, chi squared, or the like. In some embodiments a change in mappability is identified and/or determined visually (e.g., from a plot or graph). In some embodiments a change in mappability comprises a mean, median or average of a change in mappability determined for one or more reads. For example, sometimes a change in mappability comprises a mean, median or average of a change in mappability determined for both read mates of a discordant read pair. In some embodiments a change in mappability comprises a mean, median or average slope of a first relationship generated for subsequences of a first read and a second relationship generated for subsequences of a second read (e.g., a first and second read mate of a discordant read pair). A change in mappability can be generated, determined and/or identified by any suitable module, system or software. A change in mappability is often identified and/or determined by a mapping characterization module. A mapping characterization module can generate subsequences, generate relationships, characterize the mappability of subsequences, determine a change in mappability, receive or generate a mappability threshold and/or compare a change in mappability to a mappability threshold.

In some embodiments a mapping characterization module comprises instructions for a microprocessor (e.g., an algorithm) in the form of code and/or source code (e.g., a collection of standard or custom scripts) and/or one or more software packages (e.g., statistical software packages) that carry out the functions of a mapping characterization module. In some embodiments a mapping characterization module comprises code (e.g., script) written in S or R that utilizes a suitable package (e.g., an S package, an R package). For example, a slope of a change in mapping characterization can be computed in R and may comprise the following script:
lm(y~x)[["coefficients"]][2]
where y is the MAPQ scores for each stepwise alignment and x is the length of the stepwise alignment. In some embodiments a mapping characterization module comprises and/or uses a suitable statistical software package. Non-limiting examples of statistical software packages include S-plus, stata, SAS, MATLAB, statistical packages in R, the like or combinations thereof.

In some embodiments, a change in mappability can be determined for a read and/or a subset of reads. In some embodiments, a change in mappability can be determined for a read and/or a subset of reads for which discordancy is identified. In some embodiments one or more reads (e.g., a subset of reads, a subset of discordant read pairs) are selected and/or identified according to a change in mappability of sequence read subsequences. In some embodiments, identifying and/or determining a change in mappability comprises identifying and/or determining a substantial difference (e.g., a statistical difference) in mappability between two or more subsequences or subsets of subsequences of a read. In some embodiments one or more reads (e.g., a subset of reads) are identified and/or selected according to a change in mappability and/or a mappability threshold. In some embodiments a discordant read pair is selected according to a change in mappability of one or both reads and/or a mappability threshold. In some embodiments, selecting reads comprises comparing a change in mappability to a mappability threshold. In some embodiments selected reads comprising a change in mappability above, below, within, outside, significantly different or substantially the same as a mappability threshold are selected. Often one or more reads are selected where a change in mappability for one or more reads comprises a numerical (e.g., quantitative) value that is significantly different from a predetermined mappability threshold or falls outside a predetermined range of values defined by a mappability threshold. Reads (e.g., subsets of reads) can be identified and/or selected according to a read selector module (e.g., 120). In some embodiments a read selector module comprises instructions for a microprocessor (e.g., an algorithm) in the form of code and/or source code (e.g., a collection of standard or custom scripts) and/or one or more software packages (e.g., statistical software packages) that carry out the functions of a mapping characterization module. In some embodiments a read selector module comprises code (e.g., script) written in S or R that utilizes a suitable package (e.g., an S package, an R package). For example, to select reads with the average slope of mate 1 and mate 2 less than the threshold of 0 in R can be written as: data[data<0]
where data contains the mean slope of mate 1 and mate 2. In some embodiments a read selector module comprises and/or uses a suitable statistical software package. Non-limiting examples of statistical software packages include S-plus, stata, SAS, MATLAB, statistical packages in R, Prism (GraphPad Software, Inc., La Jolla, Calif.), SigmaPlot (Systat Software, Inc., San Jose, Calif.), Microsoft Excel (Redmond, Wash., USA), the like or combinations thereof.

A mappability threshold often comprises one or more predetermined values, value limits and/or a range of values. The terms "threshold" and "threshold value" herein refer to any number that is calculated using a qualifying data set and serves as a limit of selection. A mappability threshold often is calculated by mathematically and/or statistically manipulating a change in mappability.

In some embodiments a subset of reads are identified and/or selected where reads in the subset comprise a change in slope for a relationship determined between mappability and fragment length for a plurality of subsequences of each read in the subset. In some embodiments a change in slope indicates the presence of a candidate breakpoint. In some embodiments a slope of a relationship (e.g., between mappability and fragment length for a plurality of subsequences of a read) that is substantially greater than or less than 1 (e.g., a mappability threshold of 1) often indicates a read comprising a candidate breakpoint and/or identifies a subset of reads for which there is a change in mappability. In some embodiments reads (e.g., a subset of reads) comprising a change in mappability (e.g., a slope) greater than a mappability threshold of about 0, about 0.1, about 0.2, about 0.3, about 0.4, about 0.5, about 0.6, about 0.7, about 0.8, about 0.9, or greater than about 1.0 are identified and/or selected. In some embodiments reads comprising a change in mappability (e.g., a slope) outside a mappability threshold range of about −0.1 to about 0.1, about −0.2 to about 0.2, about −0.3 to about 0.3, about −0.4 to about 0.4, about −0.5 to about 0.5, about −0.6 to about 0.6, about −0.7 to about 0.7, about −0.8 to about 0.8, about −0.9 to about 0.9, or about −1.0 to about 1.0 are identified and/or selected. In some embodiments a change in mappability (e.g., an average, mean, or median slope) and/or a mappability threshold are expressed as an absolute value. A threshold can be any suitable parameter that indicates a change in mappability (e.g., a variance, standard deviation, or MAD of one or more mappability scores).

Characterizing a read and/or assessing a change in mappability of a read (e.g., subsequences of a read) can provide one or more breakpoints and/or candidate breakpoints. The term "breakpoint" as used herein refers to a position between two adjacent base calls of a read mate where bases on a first side of the breakpoint map to a first chromosome region and bases on a second side of the breakpoint map to a second chromosome region, where the first chromosome region and second chromosome region are not adjacent according to a reference genome. In some embodiments a first chromosome region and a second chromosome region are on different chromosomes. In some embodiments a first chromosome region and a second chromosome region are on the same chromosomes, where the first chromosome region and second chromosome region are not adjacent according to a reference genome. In some embodiments the term "breakpoint" as used herein refers to a position between two adjacent base calls of a read mate where bases on a first side of the position map to a reference genome and bases on a second side of the position are unmappable (e.g., cannot be mapped with a level of certainty). In some embodiments term "breakpoint" as used herein refers to a position between two adjacent base calls of a read mate where bases on a first side of the position map to a human genome and bases on a second side of the position map to heterologous genetic material (e.g., a viral genome). In some embodiments a breakpoint indicates a location and/or position of a chromosome alteration, or part thereof. In some embodiments a breakpoint identifies a nucleic acid position, according to a reference genome, where genetic material has been inserted, deleted and/or exchanged. In some embodiments, where a chromosome alteration comprises an insertion or a translocation, a breakpoint may indicate the position and/or location of one side of the insertion or translocation. In some embodiments, a first breakpoint of an insertion or translocation is identified in a first read or in a first subset of reads and a second breakpoint of the insertion or translocation is identified in a second read or second subset of reads. The term "candidate breakpoint" as used herein refers to a read and/or a position in a read that is likely to comprise a breakpoint. In some embodiments a candidate breakpoint comprises a breakpoint. In certain embodiments a candidate breakpoint does not comprises a breakpoint. Reads and/or subsets of reads identified and/or selected according to a change in mappability and/or according to a mappability threshold often comprise a candidate breakpoint.

In certain embodiments, characterizing the mappability of a plurality of sequence read subsequences generated from a read comprises identifying and/or determining the location and/or position of a candidate breakpoint. In some embodiments a read is a representation of a genome (e.g., a maternal genome, fetal genome, or a portion thereof). In certain embodiments, a mapped read comprising a candidate breakpoint is a representation of a candidate breakpoint located within a genome (e.g., a maternal genome, fetal genome, or a portion thereof). In some embodiments the location and/or position of a candidate breakpoint in a read is determined according to a relationship (e.g., a relationship between mappability and length of sequence read subsequences). In some embodiments the location and/or position of a candidate breakpoint in a read is determined according to a change in mappability. In some embodiments, identifying and/or determining the location and/or position of a candidate breakpoint in a read comprises identifying a substantial difference (e.g., a statistical difference) in mappability between two or more sequence read subsequences of a read. In some embodiments the position of a candidate breakpoint is determined at a position x where sequence read subsequences on a first side of position x comprise a mappability value that is substantially different than a mappability value for sequence read subsequences located on a second side of position x, thereby indicating a candidate breakpoint at position x. In some embodiments a position of a candidate breakpoint is determined according to a slope analysis. For example, a relationship is often determined between mappability and fragment length for a plurality of subsequences, the relationship is defined in part by a line, and the line, or portions thereof, are defined, in part, by a slope. In the foregoing example, a substantial change in slope often indicates a position of a candidate breakpoint (e.g., at a position x where subsequences on a first side of a position x comprise a slope that is substantially different than a slope for subsequences located on a second side of position x). In some embodiments, all reads comprising a putative breakpoint (e.g., as determined according to a change in mappability and/or a threshold) are de novo assembled and a breakpoint is determined. Sometimes a breakpoint is determined by aligning a read comprising a change in mappability with a reference genome. In some embodiments a location of a candidate breakpoint and/or a breakpoint is identified at a resolution of a read length. For example, a mapped read may comprise a change in mappability indicating a candidate breakpoint located at a position within a reference genome where the read is mapped. In some embodiments a location of a candidate breakpoint and/or a breakpoint is identified at a resolution of 150 or less bases, 100 or less bases, 75 or less bases, 50 or less bases, 10 or less bases, 9 or less bases, 8 or less bases, 7 or less bases, 6 or less bases, 5 or less bases, 4 or less bases, 3 or less bases, 2 or less basses or at a single base resolution.

In some embodiments candidate breakpoints are identified by a breakpoint module. A breakpoint module is often configured to identify breakpoints by a method described herein. In some embodiments a breakpoint module comprises code (e.g., script) written in S or R that utilizes a suitable package (e.g., an S package, an R package). In some embodiments a breakpoint module comprises and/or uses a suitable statistical software package. Any suitable de novo assembler, such as SOAP de-novo or those listed in Wikipedia (e.g., Wikipedia, Sequence Assembly[online], [retrieved on 2013 Sep. 25], retrieved from the internet at world wide web uniform resource locator: en.wikipedia.org/wiki/Sequence_assembly), can be used independently or in conjunction with custom scripts to identify the location of a break point. In some embodiments, given positions of mate 1 and 2, an R and/or one or more bioconductor packages in R (world wide web uniform resource locator: bioconductor.org) are used to evaluate each read, their similarity to a human reference genome to determine the break point. To determine the exact position of a break point using a slope, any suitable statistical package software or custom scripts can be used.

In some embodiments one or both discordant read mates of a discordant read pair comprise candidate breakpoints that are substantially similar and/or the same. In some embodiments one read mate of a discordant read pair comprises a candidate breakpoint and the other read mate of the pair does not comprise a candidate breakpoint. In some embodiments the sequence of a first read mate of a discordant read pair overlaps with the sequence of a second read mate of the pair and both read mates comprise the same or substantially similar candidate breakpoints. The term "substantially similar breakpoints" (e.g., "substantially similar candidate breakpoints") as used herein means breakpoints that are positioned at the same or substantially the same locations according to a reference genome. Substantially similar breakpoints are sometimes located at different relative positions (e.g., often determined relative to an end of a read) on different reads where the position of each breakpoint on each read is substantially the same according to a reference genome. Sometimes two or more reads (e.g., discordant read mates) comprise the same and/or substantially similar breakpoints, where the position of the breakpoint on each read can be the same or different. In some embodiments substantially similar breakpoints are located at the same position on different reads. In some embodiments the sequence of 1, 2, 3, 4, 5, 6, 7, or 8 or more nucleotides (e.g., base calls) that flank each side of substantially similar breakpoints are substantially the same sequence. In some embodiments substantially similar breakpoints are located on a first read and a second read where the first read is a reverse complement of the second read.

In some embodiments a subset of reads is selected according to a change in mappability where each read in a selected subset comprises a minimum length of 20 contiguous bases, 21 contiguous bases, 22 contiguous bases, 23 contiguous bases, 24 contiguous bases, 25 contiguous bases, 26 contiguous bases, 27 contiguous bases, 28 contiguous bases, 29 contiguous bases, 30 contiguous bases, 31 contiguous bases, 32 contiguous bases, 33 contiguous bases, 34 contiguous bases, 35 contiguous bases, 36 contiguous bases, 37 contiguous bases, 38 contiguous bases, 39 contiguous bases, 40 contiguous bases, 50 contiguous bases, 60 contiguous bases, 70 contiguous bases, 80 contiguous bases, 90 contiguous bases, or 100 contiguous bases.

In some embodiments a subset of reads is selected according to a change in mappability where each read in a selected subset comprise at least about 10 to about 60, 15 to about 50, 15 to about 40, 15 to about 30, 15 to about 25, or about 15 to about 20 contiguous bases on each side of a candidate breakpoint.

In some embodiments two or more reads (e.g., discordant read mates) in a sample comprise substantially similar candidate breakpoints. In some embodiments 2 or more, 5 or more, 10 or more, 20 or more, 50 or more, 100 or more or a 1000 or more reads obtained from a sample comprise the same or a substantially similar candidate breakpoint. In certain embodiments reads, discordant read mates and/or discordant read pairs that comprise a substantially similar candidate breakpoint are grouped into a subset. In some embodiments two or more subsets are identified and/or selected where each subset comprises reads comprising a substantially similar candidate breakpoint. In some embodiments a first subset of reads and a second subset of reads comprise different breakpoints. Sometimes a first subset of reads comprising a substantially similar candidate breakpoint comprises a different breakpoint than and a second subset of reads comprising a substantially similar candidate breakpoint. Often any one subset or reads comprises candidate breakpoints that are different than breakpoints in another subset of reads.

In some embodiments one or more subsets of reads comprising a substantially similar candidate breakpoint are obtained and/or generated from a reference using a system or method described herein. A subset of discordant read mates comprising substantially similar candidate breakpoints is often obtained and/or generated from a reference and a test sample (e.g., a test subject) using the same, or substantially the same method. A "reference" as used herein refers to one or more reference subjects or reference samples. A "reference" as used herein often refers to data (e.g., reads, a subset of discordant read mates, a selected set of reads) obtained from one or more reference subjects or reference samples. Often reference subjects and/or reference samples are known or presumed to lack a chromosome alteration. For example reference subjects and/or reference samples often do not comprise a chromosome alteration. In some embodiments, a reference comprises polynucleotides and/or reads of polynucleotides from a particular genomic region or a plurality of genomic regions not associated with a chromosome alteration.

Generating a Comparison

One or more subsets of reads generated and/or obtained from a test sample and a reference can be compared. Often a subset of reads from a sample comprising substantially similar candidate breakpoints is compared to a subset of reads from a reference comprising substantially similar candidate breakpoints. In some embodiments a subset of reads from a sample is compared to a subset of reads from a reference where reads from both subsets (i.e., the subset from the sample and the subset from the reference) comprise substantially similar candidate breakpoints. In some embodiments a subset of reads from a sample is compared to a subset of reads from a reference where reads from both subsets (i.e., the subset from the sample and the subset from the reference) map to the same or substantially the same locations in a reference genome. Reads that map to "substantially the same" locations in a reference genome refers to reads that map within a distance of 100,000 kilobases (kb) or less, 50,000 kb or less, 25,000 kb or less, 10,000 kb or less, 5000 kb or less, 1000 kb or less, 500 kb or less, 100 kb or less, 50 kb or less, 25 kb or less, 10 kb or less, 5 kb or less, 1000 base pairs (bp) or less, 500 bp or less, or within 100 bp or less. Reads that map to "substantially the same" locations in a reference genome sometimes refers to reads that map within a distance of 50, 30, 20, 10, 9, 8, 7, 6, 5, 4, 3, 2, 1, or 0 bases from each other. For example, sometimes a subset of reads from a sample is compared to a subset of reads from a reference where both subsets (i.e., the subset from the sample and the subset from the reference) were selected according to a change in mappability and reads from both subsets map to the same or substantially the same locations in a reference genome. In some embodiments selected subsets of reads from a sample and reference are identified according to a change in mappability, map to the same bin or portion of a genome and are compared. A bin or preselected portion of a genome to which reads are mapped can be any suitable length. In some embodiments the length of a bin or pre-selected portion of a genome to which reads are mapped is about 100,000 kilobases (kb) or less, 50,000 kb or less, 25,000 kb or less, 10,000 kb or less, 5000 kb or less, 1000 kb or less, 500 kb or less, 100 kb or less, 50 kb or less, 25 kb or less, 10 kb or less, 5 kb or less, 1000 base pairs (bp) or less, or about 500 bp or less. In some embodiments the number of reads in one or more subsets is quantitated and compared. In some embodiments the number of reads in one or more subsets of a test sample are compared to the number of reads in one or more subsets of a reference.

Subsets of reads comprising substantially similar candidate breakpoints can be compared by a suitable statistical, graphical or mathematical method. In some embodiments a comparison comprises a determination that a subset of reads from a test sample and a reference are the same or different. In some embodiments a determination that a subset of reads from a test sample and a reference are the same or different comprises a statistical analysis. In some embodiments subsets of reads are compared and a determination is made that the subsets are substantially the same or substantially different. In some embodiments the number of reads in a subset are compared and a determination is made that the number of reads from a first subset and a second subset are statistically different or not statistically different. The terms "statistically different" and "statistical difference" as used herein refers to a statistically significant difference. A statistically significant difference can be assessed by a suitable method. Non-limiting examples of a method of determining a statistically significant difference include determining and/or comparing Z-scores, distributions, correlations (e.g., a correlation coefficient, t-test, k-test and the like), uncertainty values, a measure of confidence (e.g., a confidence interval, confidence level, confidence coefficient), the like or combinations thereof. Calculating and/or comparing distributions can comprise calculating and/or comparing a probability distribution function (e.g., a kernel density estimation). Calculating and/or comparing distributions can comprise calculating and/or comparing an uncertainty value of two or more distributions. An uncertainty value generally is a measure of variance or error and can be any suitable measure of variance or error. Non-limiting examples of an uncertainty value include a standard deviation, standard error, calculated variance, p-value, mean absolute deviation (MAD), the like or combinations thereof.

In some embodiments, a comparison (e.g., determining a statistical difference) comprises comparing a subset of reads (e.g., a number of reads) to a threshold value or range. The terms "threshold" and "threshold value" herein refer to any number that is calculated using a qualifying data set (e.g., one or more references) and serves as a limit of determination (e.g., a determination of the presence or absence of a breakpoint and/or a chromosome alteration). In certain embodiments a threshold is exceeded and two or more subsets are determined as statistically different. In certain embodiments a threshold is exceeded and a test sample (e.g., a subject, e.g., a fetus) is determined to comprise a chromosome alteration. In certain embodiments a threshold is exceeded and a subset of reads is determined to comprise a breakpoint. In some embodiments a quantitative value determined for a subset of reads (e.g., a count of reads, a distribution or reads, a Z-score, an uncertainty value, a measure of confidence, the like or combinations thereof) is within or outside a threshold range of values and a determination of the presence or absence of a breakpoint and/or a chromosome alteration is determined. A threshold value or range of values often is calculated by mathematically and/or statistically manipulating read data (e.g., the number of reads in one or more subset, e.g., from a reference and/or test subject), in some embodiments. In some embodiments threshold comprises an uncertainty value.

Any suitable threshold or range can be used to determine that two subsets of reads are significantly different. In some cases two subsets of reads that differ by about 0.01 percent or more (e.g., 0.01 percent of one or either of the subset values) are significantly different. Sometimes two subsets that differ by about 0.1 percent or more are significantly different. In some cases, two subsets that differ by about 0.5 percent or more are significantly different. Sometimes two subsets that differ by about 0.5, 0.75, 1, 1.5, 2, 2.5, 3, 3.5, 4, 4.5, 5, 5.5, 6, 6.5, 7, 7.5, 8, 8.5, 9, 9.5 or more than about 10% are significantly different. Sometimes two subsets are significantly different and there is no overlap in either subsets and/or no overlap in a range defined by an uncertainty value calculated for one or both subsets. In some cases an uncertainty value (e.g., a standard deviation) is expressed as sigma. Sometimes two subsets are significantly different and they differ by about 1 or more times the uncertainty value (e.g., 1 sigma). Sometimes two subsets are significantly different and they differ by about 2 or more times the uncertainty value (e.g., deviation, standard deviation, MAD, sigma), about 3 or more, about 4 or more, about 5 or more, about 6 or more, about 7 or more, about 8 or more, about 9 or more, or about 10 or more times the uncertainty value. Sometimes two subsets are significantly different when they differ by about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 times the uncertainty value or more. In some embodiments, the confidence level increases as the difference between two subsets increases. In some cases, the confidence level decreases as the difference between two subsets decreases and/or as the uncertainty value increases.

In some embodiments the absence of a statistical difference is determined when the number of deviations (e.g., standard deviation, mean absolute deviations) between the number of reads of a test sample and reference is less than about 3.5, less than about 3.4, less than about 3.3, less than about 3.2, less than about 3.1, less than about 3.0, less than about 2.9, less than about 2.8, less than about 2.7, less than about 2.6, less than about 2.5, less than about 2.0, less than about 1.5, or less than about 1.0. For example, sometimes a number of reads of a test sample differs from a number of reads of a reference by less than 3 measures of deviation (e.g., 3 sigma, 3 MAD) and the absence of a statistical difference is determined. In some embodiments a number of reads of a test sample obtained from a pregnant female differs from a number of reads of a reference by less than 3 measures of deviation (e.g., 3 sigma, 3 MAD) and the absence of a statistical difference is determined is determined. In some embodiments a deviation of less than three between a number of reads of a test sample and a reference (e.g., 3-sigma for standard deviation) often is indicative of an absence of a chromosome alteration. A measure of deviation between a number of reads of a test sample and a number of reads of a reference for one or more reference subjects can be plotted and visualized (e.g., z-score plot).

In some embodiments a comparison comprises comparing Z-scores. In certain embodiments a comparison comprises comparing a Z-score for a subset of reads of a test sample to a predetermined threshold, a threshold range and/or to one or more Z-scores derived from a reference (e.g., a range of Z-scores). In some embodiments Z-scores and/or a threshold determined according to Z-scores is used to determine that a subset of reads is significantly different from another subset and/or from a reference. In some embodiments a subset of reads that comprise a Z-score less than and/or within a threshold range (e.g., within a level of uncertainty, e.g., less than 3, 2, or 1 sigma, within a predetermined range) are not significantly different. In some embodiments a subset of reads that comprise a Z-score greater than and/or outside a threshold range (e.g., greater than a predetermined level of uncertainty, e.g., greater than 2, 2.5, 3, 3.5, 4, 5 or 6 sigma, outside a predetermined range) are significantly different. In some embodiments the threshold or predetermined value used for comparison of a Z-score is at least 2.5, at least 2.75, at least 3.0, at least 3.25, at least 3.5, at least 3.75, at least 4.0, at least 4.25, at least 4.5, at least 4.75, at least 5.0, at least 5.25, at least 5.5, at least 5.75, at least 6.0, at least 6.25, at least 6.5, at least 6.75, at least 7.0, at least 7.25, at least 7.5, at least 7.75, at least 8, at least 8.5, at least 9, at least 9.5 or at least 10.

Comparing often comprises a multivariate analysis. In some embodiments a multivariate analysis comprises generating and/or comparing heatmaps. In some embodiments heatmaps can be compared visually and the presence and/or absence of a breakpoint and/or a chromosome alteration is determined visually. A multivariate analysis sometimes comprises a mathematical manipulation of two or more data sets (e.g., two or more subsets of reads). For example, sometimes two or more data sets (e.g., number of reads, Z-scores, uncertainty values and/or coefficients derived for two or more subsets of reads) are added, subtracted, divided, multiplied, and/or normalized.

A comparison as described herein can be performed by a comparison module (e.g., 130) or by a machine comprising a comparison module. In some embodiments a comparison module comprises code (e.g., script) written in S or R that utilizes a suitable package (e.g., an S package, an R package). For example, a heatmap can be generated using heatmap.2, an R package described in gplots (gplots [online], [retrieved on 2013 Sep. 25], retrieved from the internet at world wide web uniform resource locator: cran.r-project.org/web/packages/gplots/gplots.pdf) and available for download at gplots (gplots [online], [retrieved on 2013 Sep. 25], retrieved from the internet at world wide web uniform resource locator: cran.r-project.org/web/packages/gplots). For example a heatmap can be generated using heatmap.2 and the script heatmap.2(x)
where x is a matrix of Z-scores (computed directly using R) comparing a sample against a reference set for chromosome A and B. In some embodiments a comparison module comprises and/or uses a suitable statistical software package.

Identifying a Chromosome Alteration

In some embodiments a presence or absence of a chromosome alteration is determined. Determining the presence or absence of a chromosome alterations is sometimes referred to herein as determining or generating "an outcome" or "making a call." In some embodiments a presence or absence of a chromosome alteration is determined according to a comparison. A presence or absence of a chromosome alteration is often determined by comparing one or more selected subsets of discordant reads obtained from a sample to those obtained from a reference. In some embodiments the number of discordant read mates comprising substantially similar candidate breakpoints determined for a test sample are compared to the number of discordant read mates comprising substantially similar candidate breakpoints determined for a reference.

An absence of a chromosome alteration in a test subject (e.g., a fetus) can be determined according to a comparison. In some embodiments the absence of a chromosome alteration is determined when a selected subset of discordant reads mates from a test sample comprises the same or a substantially similar candidate breakpoint as a selected subset of discordant reads mates obtained from a reference. Sometimes an absence of a chromosome alteration in a test subject is determined where one or more, or all subsets of reads of a test sample are not different (e.g., statistically different) from subsets of reads of a reference. In certain embodiment determining the absence of a chromosome alteration comprises determining the absence of one or more breakpoints in a test sample (e.g., a test subject) according to a comparison.

A presence of one or more chromosome alterations in a test subject (e.g., a fetus) can be determined according to a comparison. In certain embodiments a presence of a chromosome alteration in a test subject is determined where one or more subsets of reads (e.g., selected subsets of reads) of a test sample are different (e.g., statistically different) from one or more subsets of reads of a reference. Sometimes a presence of a chromosome alteration in a test subject is determined by identifying a substantially greater number of reads from a test sample that comprise a candidate breakpoint or a substantially similar breakpoint compared to the number of reads from a reference that comprise a candidate breakpoint or a substantially similar breakpoint, where the candidate breakpoint and/or substantially similar breakpoint of the test sample and reference are substantially similar. In some embodiments the presence of a chromosome alteration is determined when a selected subset of discordant reads mates from a test sample comprises a candidate breakpoint and/or breakpoint that is substantially different (e.g., statistically different) than a candidate breakpoint in a selected subset of discordant reads mates obtained from a reference. In certain embodiment determining the presence of a chromosome alteration comprises identifying one or more breakpoints in a test sample (e.g., a test subject) by comparing candidate breakpoints of a test sample to candidate breakpoints of a reference. In some embodiments determining the presence of a chromosome alteration comprises identifying a subset of reads from a test sample comprising a substantially similar breakpoint, where it is determined that a reference (e.g., a subset of reads from a reference sample) does not comprise a candidate breakpoint that is substantially similar to the breakpoint identified in the test sample. In some embodiments determining the presence of a chromosome alteration comprises identifying a first breakpoint and a second breakpoint of a chromosome alteration (e.g., a translocation or an insertion) in a test subject. In some embodiments determining the presence of a chromosome deletion comprises identifying a single breakpoint in a test subject. In some embodiments determining the presence of a chromosome alteration comprises providing one or more breakpoints associated with the chromosome alteration identified in a test subject.

Sometimes a candidate breakpoint comprises a true breakpoint and sometimes a candidate breakpoint does not comprise a true breakpoint. Without being limited to theory, sometimes a candidate breakpoint is identified according to a mapping artifact caused by misalignment of two regions of a read to two different chromosomes or non-adjacent positions of a chromosome where the candidate breakpoint does not comprise a true breakpoint. Mapping artifacts and/or misalignments often occur in test samples and in reference samples (e.g., samples known not to comprise a chromosome alteration) resulting in candidate breakpoints that do not actually comprise a true breakpoint. In some embodiments the presence or absence of a breakpoint is determined according to a comparison. For example, candidate breakpoints that do not comprise a breakpoint and candidate breakpoints that comprise a true breakpoint can often be identified and/or distinguished from one another by comparing candidate breakpoints of a test sample to candidate breakpoints of a reference. For example, sometimes a breakpoint is identified by comparing a subset of reads from a test sample to a subset of reads of a reference where both subsets comprise substantially similar candidate breakpoints. Often a subset of reads from a test sample that comprise a substantially similar candidate breakpoint is determined to comprise a true breakpoint according to a comparison, where it is determined that a reference (e.g., a subset of reads from a reference sample) does not comprise a subset of reads comprising a candidate breakpoint that is substantially similar to the breakpoint identified in the test sample.

In some embodiments a location and/or position of a breakpoint is determined according to a location and/or position of a candidate breakpoint (e.g., a candidate breakpoint that comprises a the breakpoint). In certain embodiments the location and/or position of a breakpoint is determined by a method described herein to determine the location and/or position of a candidate breakpoint. In some embodiments a location and/or position of 2, 3, 4, 5, 6, 7, 8, 9, 10, 11, 12, 13, 14, 15, 16, 17, 18, 19, 20 or more breakpoints in a test subject is determined.

In some embodiments a location and/or position of a chromosome alteration is determined according to a location and/or position of one or more breakpoints. In some embodiments a first breakpoint is determined in a test sample where the location and/or position of the first breakpoint indicates the location and/or position of a chromosome alteration (e.g., a translocation, an insertion). For example, where a first translocation is located at an end of a chromosome, a single breakpoint of the first translocation can be identified indicating the location of the first translocation event. In some embodiments a first breakpoint and a second breakpoint is determined in a test sample where the location and/or position of the first and second breakpoints indicates the location and/or position of a chromosome alteration (e.g., a translocation, an insertion). For example, where a chromosome comprises an insertion, two breakpoints can sometimes be determined (e.g., 5' and 3' breakpoints representing the 5' and 3' sides of an inserted segment) where all sequence reads are mapped to the same strand (e.g., the positive strand) of a reference genome. Where a translocation is within a chromosome (e.g., a translocation comprising insertion of a segment into a chromosome), two breakpoints can often be identified. For a balanced translocation between a first and second chromosome, where a complete segment is exchanged between the two chromosomes, one or two breakpoints can sometimes be identified on the first chromosome (e.g., the 5' and/or 3' breakpoints on the first chromosome) and one or two breakpoints can sometimes be identified on the second chromosome (e.g., the 5' and/or 3' breakpoints on the second chromosome) where all sequence reads are mapped to the same strand (e.g., the positive strand) of a reference genome. In some embodiments a location and/or position of a breakpoint is determined in a test sample where the location and/or position of the breakpoint indicates a location and/or position of a chromosome deletion.

Methods described herein can provide a determination of the presence or absence of a chromosome alterations (e.g., fetal translocation) for a sample, thereby providing an outcome (e.g., thereby providing an outcome determinative of the presence or absence of a chromosome alteration (e.g., fetal translocation)). Presence or absence of a chromosome alteration can be determined by transforming, analyzing and/or manipulating sequence reads that have been mapped to a reference genome. Determining an outcome, in some embodiments, comprises analyzing nucleic acid from a pregnant female.

Any other suitable reference can be factored with a number of reads of a test sample for determining presence or absence of a chromosome alteration for a test region of a test sample. For example, a fetal fraction determination can be factored with a number of reads of a test sample to determine the presence or absence of a chromosome alteration. A suitable process for quantifying fetal fraction can be utilized, non-limiting examples of which include a mass spectrometric process, sequencing process or combination thereof.

In some embodiments a determination of the presence or absence of a chromosome alteration (e.g., translocation) is determined according to a call zone. In certain embodiments a call is made (e.g., a call determining the presence or absence of a chromosome alteration, e.g., an outcome) when a value (e.g. a measured value and/or a level of uncertainty) or collection of values falls within a pre-defined range (e.g., a zone, a call zone). In some embodiments a call zone is defined according to a collection of values that are obtained from the same patient sample. In certain embodiments a call zone is defined according to a collection of values that are derived from the same chromosome or segment thereof. In some embodiments a call zone based on a ploidy determination is defined according a level of confidence (e.g., high level of confidence, e.g., low level of uncertainty) and/or a fetal fraction. In some embodiments a call zone is defined according to a ploidy determination and a fetal fraction of about 2.0% or greater, about 2.5% or greater, about 3% or greater, about 3.25% or greater, about 3.5% or greater, about 3.75% or greater, or about 4.0% or greater. For example, in some embodiments a call is made that a fetus comprises a trisomy 21 based on a ploidy determination of greater than 1.25 with a fetal fraction determination of 2% or greater or 4% or greater for a sample obtained from a pregnant female bearing a fetus. In certain embodiments, for example, a call is made that a fetus is euploid based on a ploidy determination of less than 1.25 with a fetal fraction determination of 2% or greater or 4% or greater for a sample obtained from a pregnant female bearing a fetus. In some embodiments a call zone is defined by a confidence level of about 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. In some embodiments a call is made without using a call zone. In some embodiments a call is made using a call zone and additional data or information. In some embodiments a call is made based on a ploidy value without the use of a call zone. In some embodiments a call is made without calculating a ploidy value. In some embodiments a call is made based on visual inspection of a profile (e.g., visual inspection of genomic section levels). A call can be made by any suitable method based in full, or in part, upon determinations, values and/or data obtained by methods described herein, non-limiting examples of which include a change in mappability, a mappability threshold, a relationship, a comparison, uncertainty and/or confidence determinations, z-scores, the like or combinations thereof.

In some embodiments a no-call zone is where a call is not made. In some embodiments a no-call zone is defined by a value or collection of values that indicate low accuracy, high risk, high error, low level of confidence, high level of uncertainty, the like or a combination thereof. In some embodiments a no-call zone is defined, in part, by a fetal fraction of about 5% or less, about 4% or less, about 3% or less, about 2.5% or less, about 2.0% or less, about 1.5% or less or about 1.0% or less.

In some embodiments, a method for determining the presence or absence of a chromosome alteration (e.g., a translocation) is performed with an accuracy of at least about 90% to about 100%. For example, the presence or absence of a chromosome alteration may be determined with an accuracy of at least about 91%, 92%, 93%, 94%, 95%, 96%, 97%, 98%, 99%, 99.1%, 99.2%, 99.3%, 99.4%, 99.5%, 99.6%, 99.7%, 99.8% or 99.9%. In some embodiments, the presence or absence of a chromosome alteration is determined with an accuracy that is about the same or higher than the accuracy using other methods of chromosome alteration determination (e.g., karyotype analysis). In some embodiments, the presence or absence of a chromosome alteration is determined with an accuracy having confidence interval (CI) of about 80% to about 100%. For example, the confidence interval (CI) can be about 81%, 82%, 83%, 84%, 85%, 86%, 87%, 88%, 89%, 90%, 91%, 92%, 93%, 94%, 95%, 96%, 97%, 98%, or 99%.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater than about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein. Specific examples of generating outcomes and associated confidence levels are described in the Examples section and in international patent application no. PCT/US12/59123 (WO2013/052913) the entire content of which is incorporated herein by reference, including all text, tables, equations and drawings.

The term "sensitivity" as used herein refers to the number of true positives divided by the number of true positives plus the number of false negatives, where sensitivity (sens) may be within the range of 0≤sens≤1. The term "specificity" as used herein refers to the number of true negatives divided by the number of true negatives plus the number of false positives, where sensitivity (spec) may be within the range of 0≤spec≤1. In some embodiments a method that has sensitivity and specificity equal to one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

Ideally, the number of false negatives equal zero or close to zero, so that no subject is wrongly identified as not having at least one chromosome alteration when they indeed have at least one chromosome alteration. Conversely, an assessment often is made of the ability of a prediction algorithm to classify negatives correctly, a complementary measurement to sensitivity. Ideally, the number of false positives equal zero or close to zero, so that no subject is wrongly identified as having at least one chromosome alteration when they do not have the chromosome alteration being assessed.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a chromosome alteration can be expressed in a suitable form, which form comprises without limitation, a probability (e.g., odds ratio, p-value), likelihood, value in or out of a cluster, value over or under a threshold value, value within a range (e.g., a threshold range), value with a measure of variance or confidence, or risk factor, associated with the presence or absence of a chromosome alteration for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. In certain embodiments a predetermined threshold or cutoff value is an expected level or an expected level range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a chromosome alteration. The term "false positive" as used herein refers to a subject wrongly identified as having a chromosome alteration. The term "true negative" as used herein refers to a subject correctly identified as not having a chromosome alteration. The term "false negative" as used herein refers to a subject wrongly identified as not having a chromosome alteration. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, presence or absence of a chromosome alteration is determined from nucleic acid in a sample. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular chromosome alteration detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid. In some embodiments, the presence or absence of a chromosome alteration (e.g., translocation) is determined for a fetus. In such embodiments, the presence or absence of a chromosome alteration (e.g., translocation) is determined for a mother.

Some chromosome alterations (e.g., translocations, insertions, deletions, inversions) that can be detected by a method and/or system described herein are associated with a disorder or disease, non-limiting examples of which are shown in TABLE 1.

TABLE 1

Translocations and Associated Disorders

| Disease or Disorder | Translocation |
| --- | --- |
| 22q13.3 deletion syndrome | t(12;22)(q24.1;q13.3) |
| 3p deletion syndrome | t(X;3)(p11.2;p25) |
| 3p deletion syndrome | t(3;10)(p26;q26) |

TABLE 1-continued

Translocations and Associated Disorders

| Disease or Disorder | Translocation |
|---|---|
| 6q− like phenotype | t(5;6)(q23.1;q26) |
| Abnormal baby, mild dysmorphism, developmental delay | t(9;15)(q21.31;q26.2) |
| Abnormal hand, right radius curved and short | inv(2)(p21q31) |
| Abnormal Ultrasound | t(X;8)(q26.2;p23.2) |
| Absence of corpus callosum and ocular abnormalities | t(2;9)(p24;q32) |
| Absence of eyebrows and eyelashes, scanty scalp hair | t(1;18)(p32;q21) |
| Acampomelic campomelic dysplasia with male to female sex reversal | t(4;7;8;17)(4qter−>4p15.1::17q25.1−>17qter;7qter−>7p15.3::4p15.1−>4pter;8pter−>8q12.1::7p15.3−>7pter;17pter−>17q25.1::8q12.1−>8qter) |
| Acrobrachycephaly, ventriculomegaly, pulmonary stenosis, ectopic anus and mental retardation | t(5;21)(q13;q22) |
| Acrocephalopolysyndactyly, pentalogy of Fallot, psychomotor retardation, hypoacusis | t(1;18)(p31;q11) |
| Acute myeloblastic leukemia with maturation | t(8;21)(q22;q22)[8] |
| Acute myelogenous leukemia | t(1;12)(q21;p13) |
| Acute myeloid leukemia, congenital fibrosarcoma, secretory breast carcinoma | t(12;15)(p13;q25) |
| Acute promyelocytic leukemia | t(15;17)(q22;q21)[8] |
| Adrenogenital syndrome | t(8;10)(q21;q24) |
| Agenesis of the corpus callosum | t(1;13)(q44;q32.1) |
| Aicardi syndrome | t(X;3)(p22;q12), |
| Alagille syndrome | t(4;14)(q21;q21)pat, t(2;20)(q21.3;p12)pat, t(3;20)(q13.3;p12.2) |
| ALL | t(12;21)(p12;q22) |
| ALL | t(17;19)(q22;p13) |
| Allergy | t(3;15)(q21;q22) |
| Alport syndrome | inv(X)(q22.3q25) |
| Alstrom syndrome | t(2;11)(p13;q21)mat |
| Alternating hemiplegia of childhood | t(3;9)(p26;q34)pat |
| Ambiguous external genitalia | t(2;6)(q14;p12) |
| Amyotrophic lateral sclerosis (ALS) with frontotemporal dementia (FTD) | t(18;21)(q23;q22) |
| Anaplastic large cell lymphoma | t(2;5)(p23;q35) |
| Androgen insensitivity syndrome (AIS) | inv(X)(q11.2q27) |
| Aniridia type II | t(4;11)(q22;p13), t(11;22)(p13;q12.2), t(5;11)(q13.1;p13)pat, t(7;11)(q31.2;p13), inv(11)(p13), dir ins(12;11)(q24.11;p13p15.1), inv(11)(p13q13)mat |
| Aniridia, developmental delay | t(2;6)(q33.1;p12.1) |
| Ankylosing spondylitis | t(13;14)(q;q) |
| Anophthalmia | t(3;11)(q27;p11.2) |
| Anophthalmia (bilateral) with anomalies of the face and cervical vertebrae (1st arch syndrome) | t(4;14)(p15.3;q11) |
| Anophthalmia, esophageal atresia, genital malformation (AEG) syndrome | t(3;7)(q28;p21.3) |
| Anorchism | t(3;20)(q12;p13) |
| Anosomia, retarded bone age, dysmorphic ear | t(1;7)(q44;q22), t(8;10)(q22;q26) |
| Anterior chamber eye anolmalies, redundant skin and syndactyly | t(2;7)(q37.2;q36.3) |
| Aortic stenosis and tachycardia | t(2;6)(q21;q25) |
| Apert syndrome | t(2;9)(p11.2;q34.2)pat |
| Aplasia of the fibula and the radius (bilateral), bilateral unossified carpal bones and hypoplasia and dislocation of both tibiae | inv(2)(p15q31) |
| Aplasia of the ulna, shortening of the radius, finger anomalies and scoliosis. | t(2;10)(q31.1;q23.33) |
| Aplastic anaemia, cerebellar ataxia | t(1;20)(p22;q13.3) |
| Arthrogryposis | t(1;16)(p10;q10) |
| Asperger syndrome | t(17;19)(p13.3;p11) |
| Asplenia with cardiovascular abnormalities | t(11;20)(q13.1;q13.13)pat |
| Asplenia with cardiovascular abnormalities | inv(11)(q13q25)pat |
| Asthma | t(2;12)(q31;q24.1)pat, t(7;12)(p14;q24) |
| Atrioventricularseptal defect (AVSD), hypopituitary, posterior embryotoxon, myopia, dislocated hips | t(X;10)(q23;q25.1) |
| Attention defecit hyperactivity disorder (ADHD) | t(2;3)(q21.3;q13.31) |
| Autism | t(2;8)(q35;q21.2), t(5;13)(q12.1;q13.2) |
| Autism | t(1;15)(p35.3;q24.2) |
| Autism | t(14;16)(q12;q24.3) |
| Autism | inv(10)(q11.1q21.3) |
| Autism | t(7;13)(q31.3;q21)mat |

TABLE 1-continued

Translocations and Associated Disorders

| Disease or Disorder | Translocation |
|---|---|
| Autism | t(7;20)(q11.2;p11.2) |
| Autism | t(5;7)(q14;q32)mat |
| Autism | inv(7)(q22q31.2) |
| Autism | inv(4)(p12p15.3) |
| Autism and mental retardation | t(9;10)(q22.2;q22) |
| Autism and mental retardation | t(6;7)(p11-p12;q22)pat |
| Autism and psychomotor retardation | t(5;18)(q33.1;q12.2) |
| Autism and specific language impairment (SLI) | inv(7)(p12.2q31.3) |
| Autism and specific language impairment (SLI) | t(2;7)(p23;q31.3) |
| Autism spectrum disorder | t(2;9)(p13;p24) |
| Autistic disorder and developmental delay | t(6;8)(q13;q23.2) |
| Autistic disorder, developmental delay and epilepsy | t(5;8)(q14.3;q23.3) |
| Autistic spectrum disorder, severe learning disability, Pierre Robin sequence | t(2;3)(q33.1;q26.33) |
| Autoimmune anemia | t(1;13)(q21;q31) |
| Azoospermia | inv(1)(q22q32) |
| Azoospermia/Oligozoospermia | t(7;16)(q21.2;p13.3) |
| Azoospermia/Oligozoospermia | t(3;22) |
| Azoospermia/Oligozoospermia | t(Y;1)(q21;p13) |
| Azoospermia/Oligozoospermia | t(Y;1)(q11;p11) |
| Azoospermia/Oligozoospermia | t(Y;1)(q12;q34.3) |
| Azoospermia/Oligozoospermia | t(Y;3)(q11.2;q12) |
| Azoospermia/Oligozoospermia | t(Y;3)(q12;p21) |
| Azoospermia/Oligozoospermia | t(Y;4)(p11;q32) |
| Azoospermia/Oligozoospermia | t(Y;5)(q11;p15.3) |
| Azoospermia/Oligozoospermia | t(Y;6)(Yp6p;Yq6q) |
| Azoospermia/Oligozoospermia | t(Y;7)(q12.2;q11.1) |
| Azoospermia/Oligozoospermia | t(Y;7)(q11.2;p22) |
| Azoospermia/Oligozoospermia | t(Y;10)(q12;p13) |
| Azoospermia/Oligozoospermia | t(Y;14)(q11;p11) |
| Azoospermia/Oligozoospermia | t(Y;14)(q12.2;q11.1) |
| Azoospermia/Oligozoospermia | t(Y;16)(q11;q13) |
| Azoospermia/Oligozoospermia | t(Y;16)(q11;q13) |
| Azoospermia/Oligozoospermia | t(Y;16)(q12;q11-q12) |
| Azoospermia/Oligozoospermia | t(Y;17)(q11.21;q12) |
| Azoospermia/Oligozoospermia | t(Y;19)(q11;p or q13) |
| Azoospermia/Oligozoospermia | t(Y;19)(q12;q13) |
| Azoospermia/Oligozoospermia | t(Y;F) |
| Azoospermia/Oligozoospermia | inv(9)(p24q13) |
| Azoospermia/Oligozoospermia | t(8;22)(q21.3;p11.2) |
| Azoospermia/Oligozoospermia | t(X;5)(q28;q11) |
| Azoospermia/Oligozoospermia | t(1;22)(p22;q13) |
| Azoospermia/Oligozoospermia | t(1;15)(q11;p11) |
| Azoospermia/Oligozoospermia | t(2;13)(q37;q15) |
| Azoospermia/Oligozoospermia | t(1;20)(q21;q13) |
| Azoospermia/Oligozoospermia | t(1;10;12;5)(q42;q24;q24;p13) |
| Azoospermia/Oligozoospermia | t(19;22)(p13.1;q11) |
| Azoospermia/Oligozoospermia | t(17;21)(p13;q11) |
| Azoospermia/Oligozoospermia | t(5;8)(p14;q11) |
| Azoospermia/Oligozoospermia | t(8;9)(q23;pter) |
| Azoospermia/Oligozoospermia | t(6;13)(q15;q13) |
| Azoospermia/Oligozoospermia | t(10;13)(q26;q11) |
| Azoospermia/Oligozoospermia | t(6;11)(q15;p15) |
| Azoospermia/Oligozoospermia | t(9;20)(q34;q11)mat |
| Azoospermia/Oligozoospermia | t(11;22)(q23.3;q11.2) |
| Azoospermia/Oligozoospermia | inv(1), t(1;6)(1qter->1q25::1p13->1q25::1p13->1p22::6q23->6qter;6pter->6q23::1p22->1pter) |
| Azoospermia/Oligozoospermia | t(14;20)(q11;q13) |
| Azoospermia/Oligozoospermia | t(1;11)(p36;q13) |
| Azoospermia/Oligozoospermia | inv(2)(p11q31) |
| Azoospermia/Oligozoospermia | t(6;13)(p25;q12) |
| Azoospermia/Oligozoospermia | inv(10)(q11q22) |
| Azoospermia/Oligozoospermia | t(4;11)(q31;q23) |
| Azoospermia/Oligozoospermia | t(6;9)(q13;p24)pat |
| Azoospermia/Oligozoospermia | t(Y;4)(q11;q12) |
| Azoospermia/Oligozoospermia | t(Y;4)(q13;p16) |
| Azoospermia/Oligozoospermia | inv(9)(p11q13) |
| Azoospermia/Oligozoospermia | t(Y;15)(q15;q12) |
| Azoospermia/Oligozoospermia | inv(9)(p11q13) |
| Azoospermia/Oligozoospermia | t(Y;1)(q11.2;p34.3) |
| Azoospermia/Oligozoospermia | t(Y;6)(q11.23-q12;p11.1) |
| Azoospermia/Oligozoospermia | t(Y;16)(q11.21;q24) |
| Azoospermia/Oligozoospermia | t(17;22)(q11;q12) |

TABLE 1-continued

Translocations and Associated Disorders

| Disease or Disorder | Translocation |
|---|---|
| Azoospermia/Oligozoospermia | t(1;2)(p34;p21) |
| Azoospermia/Oligozoospermia | t(4;5)(q21;q11.2)pat |
| Azoospermia/Oligozoospermia | t(1;9;21)(1qter->1p11::21q11.2->21qter;9pter->9p24?::9p21->9qter;21pter->21q11.1::1p12->1p34.1?::9p21->9p24?::1p34.1?-1pter) |
| Azoospermia/Oligozoospermia | t(1;5)(p32;q31)mat |
| Azoospermia/Oligozoospermia | t(1;15)(q43?;q15?) |
| Azoospermia/Oligozoospermia | t(3;12)(p14;p11) |
| Azoospermia/Oligozoospermia | inv(9)(q32q34) |
| Azoospermia/Oligozoospermia | t(3;12)(p24;p12)pat |
| Azoospermia/Oligozoospermia | t(X;5)(p22.1;p11) |
| Azoospermia/Oligozoospermia | inv(10)(p11.3q21.2) |
| Azoospermia/Oligozoospermia | inv(7)(q11.2q22) |
| Azoospermia/Oligozoospermia | t(4;5)(q32;q14) |
| Azoospermia/Oligozoospermia | t(Y;2)(q11.22;q34) |
| Azoospermia/Oligozoospermia | t(4;15)(p16;q22.2) |
| Azoospermia/Oligozoospermia | t(9;15)(q22;q26) |
| Azoospermia/Oligozoospermia | t(3;14)(p13;q13) |
| Azoospermia/Oligozoospermia | t(1;16)(q23;p13) |
| Azoospermia/Oligozoospermia | inv(1)(p34q23) |
| Azoospermia/Oligozoospermia | t(1;11)(p36;q25) |
| Azoospermia/Oligozoospermia | inv(1)(p32q42) |
| Azoospermia/Oligozoospermia | inv(1)(p32q31) |
| Azoospermia/Oligozoospermia | inv(1)(p32q42) |
| Azoospermia/Oligozoospermia | t(Y;1)(q12;q12) |
| Azoospermia/Oligozoospermia | t(X;19)(q22;q13.3) |
| Azoospermia/Oligozoospermia | t(X;8)(p22;q11) |
| Azoospermia/Oligozoospermia | t(1;21)(q11;p13) |
| Azoospermia/Oligozoospermia | t(1;22)(q11;p11) |
| Azoospermia/Oligozoospermia | t(1;13)(q11;p13) |
| Azoospermia/Oligozoospermia | t(1;21)(p13;p13) |
| Azoospermia/Oligozoospermia | t(Y;1)(q11;q11)pat |
| Azoospermia/Oligozoospermia | t(1;21)(q21;p11) |
| Azoospermia/Oligozoospermia | t(16;21)(q12;p11) |
| Azoospermia/Oligozoospermia | t(16;22)(p13;q11) |
| Azoospermia/Oligozoospermia | t(Y;1)(q12;q25) |
| Azoospermia/Oligozoospermia | t(4;15)(q25;p11) |
| Azoospermia/Oligozoospermia | t(3;20;21) |
| Azoospermia/Oligozoospermia | inv(1)(p13q25) |
| Azoospermia/Oligozoospermia | inv(1)(p34q23)mat |
| Azoospermia/Oligozoospermia | inv(1)(p35q21.3)mat |
| Azoospermia/Oligozoospermia | inv(1)(p32q12) |
| Azoospermia/Oligozoospermia | inv(1)(p36.3q12) |
| Azoospermia/Oligozoospermia | inv(1)(p32q42) |
| Azoospermia/Oligozoospermia | inv(1)(p31q43) |
| Azoospermia/Oligozoospermia | inv(1)(p34q23)mat |
| Azoospermia/Oligozoospermia | inv(Y)(p11q11) |
| Azoospermia/Oligozoospermia | t(X;11)(q26;q21) |
| Azoospermia/Oligozoospermia | t(8;13)(q21;p11) |
| Bardet-Biedl syndrome | t(2;17)(p;p) |
| Bartter syndrome associated with 21-hydroxylase deficiency | t(6;9)(q;p)mat |
| Beckwith Weidemann syndrome (BWS) | t(11;12)(p15.5;q13.1) |
| Beckwith Weidemann syndrome (BWS) | t(11;16)(p15.5;q12) |
| Beckwith Weidemann syndrome (BWS) | t(4;11)(p15.2;p15.4) |
| Beckwith Weidemann syndrome (BWS) | t(10;11)(p13;p15.5) |
| Beckwith Weidemann syndrome (BWS) | inv(11)(p15.4q22.3) |
| Beckwith Weidemann syndrome (BWS) | inv(11)(p11.2p15.5) |
| Beckwith-Wiedemann syndrome (BWS) | t(11;22)(p15.5;q12)mat |
| Beckwith-Wiedemann syndrome (BWS) | t(9;11)(p11;p15.5)mat |
| Beckwith-Wiedemann syndrome (BWS) | t(X;1)(q26;q12) |
| Benign neonatal epilepsy | inv(5)(p15.1q11.2) |
| Bilateral internal carotid artery agenesis, severe psychomotor developmental delay, dysmorphic face | t(1;3)(p31.2;p21) |
| Bilateral periventricular nodular heterotopia (BPNH) and bilateral perisylvian polymicrogyria (PMG) | t(1;6)(p12;p12.2) |
| Bilateral renal adysplasia | t(2;8)(q11;q24) |
| Bilateral renal adysplasia | t(1;2)(q32;p25) |
| Bilateral split foot malformation (SFM) or Ectrodactyly | t(2;11)(q14.2;q14.2) |
| Bilateral ulnar aplasia with postaxial oligodactyly | t(6;7)(q21;q31.2) |
| Biploar Disorder | t(8;15)(p21;q24)pat |
| Bipolar affective disorder | t(11;15)(q24.2;q26.3) |

TABLE 1-continued

Translocations and Associated Disorders

| Disease or Disorder | Translocation |
| --- | --- |
| Bipolar Disorder | t(4;12)(p15.3;q22) |
| Bipolar Disorder | t(9;17)(q33;q25.3) |
| Bipolar Disorder | inv(18)(p11.31q21.1) |
| Bipolar disorder and X-linked mental retardation | t(X;12)(q24;q15) |
| Bladder exstrophy | t(8;9)(p11.2;q13) |
| Blepharophimosis, ptosis, and epicanthus inversus (BPES) | t(3;7)(q23;q32) |
| Blepharophimosis, ptosis, and epicanthus inversus (BPES) | t(3;4)(q23;p15.2) |
| Blepharophimosis, ptosis, and epicanthus inversus (BPES) | t(3;8)(q23;p21.1) |
| Blepharophimosis, ptosis, and epicanthus inversus (BPES) | t(3;21)(q23;q22.1) |
| Blepharophimosis, ptosis, and epicanthus inversus (BPES) | t(X;3)(p22;q21) |
| Blepharophimosis, ptosis, and epicanthus inversus (BPES) | t(3;11)(q21;q23)pat |
| Blepharophimosis-ptosis-epicanthus inversus syndrome | t(2;3)(q33;q23) |
| Borderline mental retardation | t(7;13)(q11.2;q22) |
| Brachydactyly-syndactyly | 46, XY, t(4;6)(q12;p23) |
| Brachydactyly-syndactyly | 46, XY, t(4;6)(q12;p23) |
| Brachydactyly-syndactyly | t(4;6)(q12;p23) |
| Breast cancer | t(17;19)(q21;q13) |
| Breast cancer, 11-22 translocation associated | t(11;22)(q23;q11) |
| Brittle bones, blue sclera | t(13;14)(q;q) |
| Brody Myopathy (exercise-induced impairment in muscle relaxation) | t(2;7)(p11.2;p12.1) |
| Burkitt's lymphoma | t(8;14)(q24;q32) |
| Campomelic dysplasia | t(5;8)(q33.1;q21.4)pat |
| Campomelic dysplasia | t(2;17)(q35;q23-q24) |
| Campomelic dysplasia | t(12;17)(q21.32;q24.3-q25.1) |
| Campomelic dysplasia | t(5;17)(q14;q25.1) |
| Campomelic dysplasia | t(7;17)(q34;q25.1) |
| Campomelic dysplasia | t(9;17)(p13;q23.3-q24.1) |
| Campomelic dysplasia | t(13;17)(q22;q25.1) |
| Campomelic dysplasia | t(1;17)(q24.13;q24.3-q25.1) |
| Campomelic dysplasia | t(6;17)(q14;q24) |
| Campomelic dysplasia | t(10;17)(q24;q23) |
| Campomelic dysplasia | t(5;17)(q13.3;q24.2) |
| Campomelic dysplasia | inv(17)(q11.2;q24.3-q25.1) |
| Campomelic dysplasia | t(17;22)(q25.1;p11.2) |
| Campomelic dysplasia | inv(17)(q12;q25) |
| Campomelic dysplasia | t(4;17)(q21.3;q23.3) |
| Cataract | t(7;9)(p15;q22) |
| Cataract, anterior polar 1 | t(2;14)(p25;q24) |
| Cataract, congenital | t(3;4)(p26;p15)pat |
| Cataract, congenital | t(X;22)(q13;q11) |
| Cataracts, microcephaly | t(9;20)(p13.3;p13) |
| Cenani syndactylism | t(12;22)(p11.2;q13.3)pat |
| Cerebellar vermis aplasia | t(8;20)(p22;q13) |
| Cerebral atrophy, macrocephaly seizures, and developmental delay | t(1;3)(q32.1;q25.1) |
| Cerebral cavernous malformations (CCM) and premature ovarian failure (POF) | t(X;3)(q22.3;q12.3) |
| Cerebral ventriculomegaly, atrial septal defect, abnormal segmentation of the lungs, high-arched palate, and small low-set ears | t(3;10)(p13;q21.1), inv(6)(p23q12) |
| Cerebro-oculo-facio-skeletal syndrome (COFS) | t(1;16)(q23;q13)mat |
| Ceroid lipofuscinosis, neuronal 3, juvenile (CLN3) | t(10;18)(q22.1;q21.1) |
| Cervical Vertebral Fusion | t(5;17)(q11.2;q23) |
| CHARGE syndrome | t(8;13)(q11.2;q22) |
| CHARGE syndrome | t(2;7)(p14;q21.11) |
| CHARGE syndrome | t(6;8)(p10;p10) |
| Child onset Schizophrenia | t(1;7)(p22;q21)pat |
| Chondrodysplasia punctata 1, X-linked recessive (CDPX1) | t(X;Y)(p22.3;q11.23)mat |
| Choroideremia | t(X;13)(q21.2;p12) |
| Choroideremia | t(X;7)(q21;p12) |
| Choroideremia, sensorineural deafness and primary ovarian failure | t(X;4)(q21.2;p16.3) |
| Chronic myelogenous leukemia (CML), acute lymphoblastic leukemia (ALL) | t(9;22)(q34;q11) Philadelphia chromosome |

TABLE 1-continued

Translocations and Associated Disorders

| Disease or Disorder | Translocation |
|---|---|
| Clear cell Renal cell carcinoma | t(3;8)(p14;q24.1) |
| Cleft lip and palate, Isolated | t(2;8)(q33.1;q24.2) |
| Cleft lip and palate, other dysmorphism | t(6;9)(p24.3;q22.33) |
| Cleft lip and ventricular septal defect | t(2;10)(q53;p13) |
| Cleft lip and ventricular septal defect | t(10;14)(p13;q24)pat |
| Cleft palate, isolated | t(2;7)(q33.1;p21.1) |
| Cleft palate, isolated | t(2;11)(q33.1;p13) |
| Cleft palate, Isolated | t(6;7)(p25;q31) |
| Cleft palate, prominent ears, small chin, tapering fingers | t(11;13)(p15.4;q22.1) |
| Cleft palate, severe learning disabilities | inv(12)(p11.21q24.31) |
| Cleidocranial dysplasia (CCD) | t(2;6)(q36;q16) |
| Cleidocranial dysplasia (CCD) | inv(6)(p21q16) |
| Cleidocranial dysplasia (CCD) | t(6;18)(p12;q23) |
| Cleidocranial dysplasia (CCD) | t(8;10)(q22.3;p12.3)mat |
| Cleidocranial dysplasia (CCD) | t(4;6;21)(p16;p21.1;q21) |
| Club hands, club feet, pectus excavatum | t(2;10)(q21.1;q24.3) |
| CML, ALL | t(9;12)(p24;p13) |
| Cohen syndrome | t(5;7)(q33.1;p15.1) |
| Coloboma (bilateral), cleft lip and palate, micropthalmia, mental retardation | inv(4)(q21.22q35) |
| Coloboma (choroidal), bilateral optic-pit coloboma | t(4;10)(q12;p13) |
| Coloboma (iris), ptosis, hypertelorism, and mental retardation | inv(2)(p12q14)mat |
| Coloboma (iris), ptosis, hypertelorism, and mental retardation | inv(2)(p12q14)mat |
| Coloboma (iris), ptosis, hypertelorism, and mental retardation | t(9;13)(q32;q22) |
| Combined methylmalonic aciduria and homocystinuria (cblC type) | t(8;19)(q23.2;q13.3)pat |
| Combined pituitary hormone deficiency | t(10;11)(q26;q13)pat |
| Complete gonadal failure, abnormal external genitalia and multiple congenital abnormalities. Bilateral undescended testes, glandular hypospadias and hypoplastic penis were noted at birth. | t(6;8)(q27;q13.2) |
| Compley congenital heart disease, asplenia, malrotation | t(3;6)(q21.3;p21.1) |
| Congenital absence of uterine and vagina | t(3;16)(p23;p13.3) |
| Congenital adrenal hyperplasia due to 21-hydroxylase deficiency | t(13;18)(q31;p11) |
| Congenital agammaglobulinemia and minor facial abnormalities | t(9;20)(q33.2;q12) |
| Congenital anomalies | t(6;17)(q27;q24.3) |
| Congenital arhinia, microphthalmia, hypertelorism, high arched palate, hypoplasia of auditory canal, mastoid and facial bones, absence of olfactory bulbs/tracts, coloboma of the iris | t(3;12)(q13.2;p11.2) |
| Congenital Cataract | t(3;5)(p22.3;p15.1) |
| Congenital glaucoma, cleft lip and palate and mental retardation | t(1;6)(q23;q27) |
| Congenital glaucoma, mental retardation and dysmorphic features | t(2;10)(q33;q26)pat, t(8;12)(q24;q21) |
| Congenital hydrocephalus, thin corpus callosum, Chiari I malformation, tethered spinal cord, low vertebral deformity and congenital bilateral dysplastic kidneys | t(1;20)(p31.3;q13.31) |
| Congenital lamellar cataract | t(16;22)(p13.3;q11.2) |
| Congenital microcephaly, corpus callosum agenesis, bilateral polymicrogyria, ventricular dilatation and a small cerebellum | t(3;10)(p24;q23)mat, t(3;10)(p24;q23)pat |
| Congenital ptosis | t(1;8)(p34.3;q21.12) |
| Congenital scoliosis (hemivertebra) | t(13;17)(q34;p11.2) |
| Congenital secundum-type atrial septal defect and gonadal dysgenesis | t(8;10)(q24.1;q21.1) |
| Congenital sensorineural hearing loss (SNHL) | t(10;11)(q24.3;q23.3), t(10;11)(q24.3;q23.3) |
| Cornelia de Lange syndrome | t(14;21)(q32;q11) |
| Cornelia de Lange syndrome | t(3;17)(q26.3;q23.1) |
| Cornelia de Lange syndrome | t(5;13)(p13.1;q12.1) |
| Cornelia de Lange syndrome | t(3;5)(q21;p13) |
| Coronary heart disease | t(6;14)(q13;q32) |
| Coronary heart disease | t(7;16)(q11.2;p13.1) |

TABLE 1-continued

Translocations and Associated Disorders

| Disease or Disorder | Translocation |
|---|---|
| Cortical lissencephaly with cerebellar hypoplasia, severe epilepsy, and mental retardation | t(7;12)(q22;p13)mat, t(7;12)(q22;p13)pat |
| Costello syndrome | t(1;22)(q25;q13.1) |
| Craniofacial and acallosal central nervous system midline defects | t(4;14)(q25;q13) |
| Craniostenosis and retardation | t(7;13)(p;p13) |
| Craniosynostosis | t(6;7)(q16.2;p15.3) |
| Craniosynostosis | t(9;11)(q33.1;p15.3) |
| Craniosynostosis, brachycephaly, proptosis, midfacial hypoplasia and low set ears | t(9;11)(q33.1;p15.3) |
| Crouzon dysostosis | t(2;3)(p12;p26)pat |
| Cryptorchidism | t(1;4)(p31;q35) |
| Cryptorchidism | t(1;7)(p32;q35), inv(12)(q15q24) |
| Cryptorchidism (bilateral) | inv(Y)(p11q11) |
| Cryptorchidism (bilateral) | t(4;16)(p14;q24) |
| Cryptorchidism (left intracanalicular) | inv(9)(p11q13) |
| Cryptorchidism (left intracanalicular) | inv(9)(p11q13) |
| Cryptorchidism (left intracanalicular) | inv(9)(p11q13) |
| Cutis marmorata telangiectatica congenita (CMTC) with premature ovarian failure | t(8;9)(q22.1;p24.1) |
| Cystinuria (with mental retardation) | t(14;20)(q22;p13) |
| Dandy-Walker syndrome (DWS) | t(1;2)(p36;p12)/t(2;5)(p12;q35)/t(2;6)(p12;q27)/ t(2;12)(p12;q24) |
| Decreased ovarian reserve (DOR) | rob(13;21)(q10;q10) |
| Depressor anguli oris muscle hypoplasia and imperforate anus | inv(15) |
| Developmental delay | t(2;10)(p;q) |
| Developmental delay | inv(19)(p13.2p13.3)mat |
| Developmental delay | dic(10;22)(q26.3;p13) |
| Developmental delay, autistic behaviour, ptosis, epicanthal folds | t(3;18;8)(3pter-->3q13.1::18q22.2-->18q23::8q21.2--> 8qter; 18pter-->18q22.2::3q13.1-->3q23::18q23--> 18qter; 8pter-->8q21.2::3q23-->3qter) |
| Developmental delay, especially in language, split coronal sutures, fused sagittal suture, minor dysmorphic features | inv(1)(inv ins(1;3)(q32;p14p24)q44) |
| Developmental delay, mental retardation, short stature and microcephaly, seizures and hypotonia of the trunk and limbs. | t(X;9)(q28;q12) |
| Developmental delay, mild microcephaly, epicanthus tarsalis, tapering fingers | t(2;12)(q13;p11.23), ins(5;12)(p14.2;q12q13.13) |
| Developmental delay, particularly speech, distinct face, antineutrophil cytoplasmic antibodies, recurrent infections | t(1;6)(q32.3;q22.3) |
| Developmental delay, polycystic kidneys, ventricular septal defect, pulmonary stenosis | t(16;17;20)(p13.3;p13.3;q13.33), inv ins(4;16)(p16.3;p13.13p12.2), ins(16;4)(p;p16.3p16.3) |
| Developmental delay, seizures | t(5;20)(q15;p12) |
| Developmental delay, ventricular septal defect, aorta coarctation, minor anomalies | t(8;10)(q12.3;p11.22) |
| Developmental retardation, secundum type atrial septal defect, bicornuate uterus with double cervix, septate upper 3rd of vagina | t(2;4)(p25;q21), t(10;18)(p15;q12.2) |
| Dextro-looped transposition of the great arteries (DTGA), perimembranous ventricular septal defect and an open foramen ovale, as well as mild coarctation of the aorta. | t(12, 17)(q24.1;q21) |
| DFSP | t(17;22) |
| Di George syndrome (DGS) | t(2;22)(q14;q11.21)mat |
| Di George syndrome (DGS) | t(21;22)(p12;q11) |
| Diabetes Mellitus, Insulin Dependent (Type 1 diabetes, IDDM) | t(2;12)(q31;q24.1) |
| Diabetes Mellitus, Insulin Dependent (Type 1 diabetes, IDDM) | t(10;17)(p11.21;q25.1) |
| Diamond-Blackfan anaemia (DBA) | t(X;19)(p21;q13) |
| Diamond-Blackfan anaemia (DBA) | t(8;19)(q35;q13) |
| Diaphragmatic hernia | t(8;15)(q22.3;q15) |
| Diaphragmatic hernia | t(8;13)(q22.3;q22)mat |
| Dolichocephalic skull, low set abnormal ears, antimongoloid palpebral fissures, epicanthal folds, cleft of soft palate, partial cleft of hard palate, micrognathia and severe mental retardation | t(2;8;20)(q23;q22;q11.2) |
| Duane retraction syndrome | t(6;8)(q26;q13) |
| Duchenne muscular dystrophy (DMD) | t(X;11)(p21;q13) |
| Duchenne muscular dystrophy (DMD) | t(X;3)(p21;q13) |
| Duchenne muscular dystrophy (DMD) | t(X;5)(p21.2;q31.2) |

TABLE 1-continued

Translocations and Associated Disorders

| Disease or Disorder | Translocation |
|---|---|
| Duchenne muscular dystrophy (DMD) | t(X;21)(p21;p12) |
| Duchenne muscular dystrophy (DMD) | t(X;4)(p21.1;q26) |
| Duchenne muscular dystrophy (DMD) | t(X;6)(p21;q21) |
| Duchenne muscular dystrophy (DMD) | t(X;5)(p21;q35) |
| Duchenne muscular dystrophy (DMD) | t(X;9)(p21;p22) |
| Duchenne muscular dystrophy (DMD) | t(X;2)(p21;q36) |
| Duchenne muscular dystrophy (DMD) | der(X;1)t(X;1)(p21;p34) inv(X)(p11p21) |
| Duchenne muscular dystrophy (DMD) | t(X;4)(p21;q35) |
| Duchenne muscular dystrophy (DMD) | t(X;15)(p21;q26) |
| Duchenne muscular dystrophy (DMD) | t(X;12)(p21.2;q24.33) |
| Duchenne muscular dystrophy (DMD), Turner's syndrome, epilepsy and mental retardation | t(X;9)(p21;p21) |
| Dysgerminoma | t(8;22)(q24.13;q11.21) |
| Dyslexia | t(1;2)(p22;q31)pat |
| Dyslexia | t(2;15)(q11;q21)pat |
| Dyslexia | t(6;15)(q22;q21) |
| Dyslexia and Colon tumour | t(1;18)(p36.1;q21) |
| Dysmorphic features, inc facial stigmata, ulnar deviation, hypoplastic fifth toe. Hypoplastic corpus callosum, variant Dandy-Walker cyst, poorly differentiated liver, epilepsy | t(X;15)(p11.3;q26) |
| Dysmorphic syndrome | t(2;6)(p13;p25) |
| Dystrophic epidermolysis bullosa (DEB). | t(5;13)(q13;q32) |
| Dystrophy of the retinal pigment epithelium and facial dysmorphisms | t(3;5)(q25;q11.2) |
| Early onset Alzheimers | inv(14)(q24q24) |
| Early onset obesity | t(1;6)(p22.1;q16.2) |
| Ectodermal dysplasia 1, anhidrotic | t(X;12)(q13.1;q24.2) |
| Ectodermal dysplasia 1, anhidrotic | t(X;1)(q13.1;p36.3) |
| Ectodermal dysplasia 1, anhidrotic | t(X;9)(q12;q12) |
| Ectodermal dysplasia 1, anhidrotic, and mental retardation | t(X;9)(q13.1;p24) |
| Ectodermal dysplasia, hypodontia and developmental delay | t(1;6)(p22.1;p22.2) |
| Ectrodactyly, Ectodermal Dysplasia and cleft lip/palate syndrome 1 (EEC1) | t(7;9)(q21.3;p12)pat |
| Ectrodactyly, Ectodermal Dysplasia and cleft lip/palate syndrome 1 (EEC1) | t(2;7)(q21.1;q22.3) |
| Ectrodactyly, Ectodermal Dysplasia and cleft lip/palate syndrome 1 (EEC1) | t(7;12)(q21.3;q24.2) |
| Ectrodactyly, Ectodermal Dysplasia and cleft lip/palate syndrome 1 (EEC1) | t(6;13)(q21;q12) |
| Ectrodactyly, syndactyly | t(2;5)(q35;q23) |
| Ehlers-Danlos type I (and hypomelanosis of Ito) | t(X;9)(p21.1;q34.3) |
| Enlarged clitoris | t(11;17)(q14;p13)mat |
| Eosinophilia | inv(10)(p11.2q21.2) |
| Epicanthal folds, flat nasal bridge, small mouth, micrognathia, low set ears, cleft palate | t(9;11)(p21.2;p14.2) |
| Epilepsy and mental retardation | t(14;16)(q32;p13.3)inv |
| Epilepsy, congenital capillary abnormalities, infantile hypotonia, developmental delay and obesity | t(X;2)(p11.2;q37) |
| Epilepsy, disturbed sleep-wake cycle, increased anxiety, aggressive behavior, mental retardation but not hyperekplexia | t(X;18)(q11.1;q11.21) |
| Epileptic encephalopathy with spastic tetraparesis, severe psychomotor retardation, hypogonadism, micropenis, cryptorchidism, microcephaly, chorioretinal atrophy, hypopigmentation of the hair, minor facial and hand dysmorphism. | t(2;6)(q24.3;q22.31) |
| Ewing's sarcoma | t(11;22)(q24;q11.2-12) |
| Eye disease (possibly early Norrie's) | t(X;1)(p11.4;p36.3) |
| Facial dysmorphism and hydronephrosis. | t(16;20)(q23;p11.2) |
| Facial dysmorphology, poor psychomotor development | t(X;1)(p21;p34) |
| Faciogenital Dysplasia (Aarskog-Scott syndrome) | t(X;8)(p11.2;q11.21)mat |
| Factor VII deficiency | t(Y;13)(q11;q34) |
| Factor X deficiency | t(Y;13)(q11;q34) |
| Failure to thrive, dysmorphic, clinodactyly | t(5;7)(p10;p10) |
| Failure to thrive, moderate mental retardation, facial features suggestive of WBS, and chronic constipation | t(7;12)(q11.22;q14.2) |

TABLE 1-continued

Translocations and Associated Disorders

| Disease or Disorder | Translocation |
|---|---|
| Familial adenomatous polyposis (FAP) | inv(5)(q22q31.3) |
| Familial adenomatous polyposis (FAP) | t(5;10)(q22;q25) |
| Familial intestinal neurofibromatosis (NF3B) | t(12;14)(q13;q13) |
| Familial myelodysplastic syndrome (MDS) and Acute Lymphoblastic Leukemia (ALL) | inv(1)(p31.1q25.1) |
| Fatal generalised amyoplasia with lower limb arthrogryposis | ins(2;5)(q14.1;q14.1q23.2) |
| Fatal generalized amyoplasia with lower limb arthrogryposis and dysmorphic features | ins(2;5)(q14.1;q14.1q23.2) |
| Features similar to 9q34 subtelomeric deletion syndrome | t(X;9)(p11.23;q34.3) |
| Female sterility | t(6;14)(p12;q12) |
| FG syndrome/Keller syndrome | inv(X)(q12q28) |
| Fibrosis of extraocular muscles, congenital, type 3; CFEOM3 | t(2;13)(q37.3;q12.11) |
| Fifth Digit syndrome (Coffin-Siris) | t(1;7)(q21.3;q34) |
| Fifth Digit syndrome (Coffin-Siris) | t(7;22)(q32;q11.2) |
| Fifth Digit syndrome (Coffin-Siris) | t(12;14)(q24;q32) |
| First brachial arch defect | t(2;10)(q;p) |
| First brachial arch defect | t(4;14)(p15.3;q11) |
| Follicular lymphoma | t(14;18)(q32;q21) |
| Follicular thyroid cancer | t(2;3)(q13;p25) |
| Fragile 16(q22) | t(1;16)(q32;q22) |
| Fraser syndrome | inv(9)(p11q21)pat |
| Frontofacionasal dysplasia (FFND) | t(8;12)(q22;q21) |
| Frontonasal dysplasia | t(7;3)(3;11)(7pter-->7q21.3::3q27-->3qter;3pter--> 3q23::11q21-->11qter; 11pter-->11q21::3q23--> 3q27::7q21.3-->7qter) |
| Frontonasal dysplasia | t(15;22)(q22;q13)mat |
| Genital malformations, including very small penis with chordee, bifid scrotum, hypospadias | t(X;5)(q13;p15)mat |
| Genitourinary malformations | t(1;18)(q32.1;q22.1) |
| Gilles de la tourette syndrome (GTS) | t(7;18)(q22;q22.1) |
| Gilles de la tourette syndrome (GTS) | t(3;8)(p21.3;q24.1)mat |
| Gilles de la tourette syndrome (GTS) | t(1;8)(q21.1;q22.1)pat |
| Gilles de la tourette syndrome (GTS) | t(6;8)(p23;q13)mat |
| Gilles de la tourette syndrome (GTS) | t(6;8)(q24;q13) |
| Gilles de la tourette syndrome (GTS) | inv(13)(q31.1q33.1) |
| Gilles de la tourette syndrome (GTS) and Obsessive compulsive disorder, mental retardation, speech abnormalities and growth retardation | inv(2)(p23q22), ins(7;2)(q35;p21p23) |
| Gillespie syndrome | t(X;11)(p22.22;p11.2) |
| Gingival hyperplasia | t(7;10)(q35;q22) |
| Global developmental delay | t(5;11)(q15;p15.5) |
| Global developmental delay and seizure disorder | dir ins(2;4)(p24;p15.3p13) |
| Global developmental delay, IUGR, dysmorphic features, brachydactyly | t(13;18)(q31.1;q22.2) |
| Global developmental delay, leftward deviation of occiput and eyes, hypertonia, head lag | t(2;8)(q23.2;q23.3) |
| Glycogen storage disease type Ia and Sanfilippo syndrome type B | t(12;20)(q15;q13.1) |
| Gonadal dysgenesis | t(X;12)(q22;q24) |
| Greig cephalo-polysyndactyly syndrome (GCPS) | t(3;7)(p21.1;p13) |
| Greig cephalo-polysyndactyly syndrome (GCPS) | t(6;7)(q27;p13)mat |
| Gross congenital abnormalities, including microcephaly, abnormal facies, severe mental retardation, epilepsy, anemia, thrombocytopenia, peculiar fragility of the skin, inability to experience pain | t(9;17)(q34;q11) |
| Growth and psychomotor retardation, feeding problems, microcephaly, low set ears, short neck and brachydactyly | t(7;15)(q32;q15) |
| Haemolytic anaemia, Turner syndrome, prenatal onset short stature, ?developmental delay | t(5;7)(q14.3;q22.1) |
| Haemophilia B | t(X;1)(q27;q23) |
| Haemophilia B | t(X;15)(q27.1;p11.2) |
| Hamartoma of the retinal pigment epithelium | t(11;18)(p13;p11.31) |
| Hereditary cyclic neutropenia | inv(Y)(p11.2q11.23)pat |
| Hereditary hemochromatosis (HFE) | inv(6)(p21.1p23) |

TABLE 1-continued

Translocations and Associated Disorders

| Disease or Disorder | Translocation |
|---|---|
| Hereditary neuropathy with liability to pressure palsies (HNPP) | t(16;17)(q12;p11.2)mat |
| Hereditary orotic aciduria | inv(4)(p12q25) |
| Heterotaxy | t(6;18)(q21;q21) |
| Heterotaxy | t(6;20)(q21;p13) |
| Heterotaxy | inv(12)(q12q24.3) |
| Heterotaxy | t(12;13)(q13.1;p13)mat |
| Heterotaxy | t(7;16)(p22;q24) |
| Heterotaxy and several other malformations including peculiar facies, micropthalmia, ectrodactyly, syndactyly, slight mental retardation | ins(7;8)(q22;q12q24) |
| Hirschsprung disease | t(2;11)(q22.2;q21) |
| Hirschsprung disease, hydrocephalus, and vesico-ureteral reflux | t(3;17)(p12.11;q11.21) |
| Hirschsprung disease, severe mental retardation and dysmorphic facial features including hypertelorism, prominent forehead and dysmorphic ears | t(2;11)(q22.2;q21) |
| Hodgkin disease | t(Y;1)(q21;p13) |
| Holoprosencephaly (HPE) and cleidocranial dysplasia (CCD) | t(6;7)(p21.1;q36) |
| Holoprosencephaly 1, Alobar (HPE1) | t(3;7)(p23;q36) |
| Holoprosencephaly 2, HPE2 | t(5;12)(p14.1;q24.4) |
| Holoprosencephaly 2, HPE2 | inv ins(2)(p21q24q13) |
| Holoprosencephaly 2, HPE2 | t(1;2)(p21;p21) |
| Holoprosencephaly 2, HPE2 | t(1;2)(p22.3;p21) |
| Holoprosencephaly 3 (HPE3) | t(7;13)(q21.2;q33) |
| Holoprosencephaly 3 (HPE3) | t(3;19)(p14.1;p13.1) |
| Holoprosencephaly 3 (HPE3) | t(7;9)(q36;q34)mat |
| Holoprosencephaly, hypertelorism and ectrodactyly | t(2;4)(q14.2;q35) |
| Holt-Oram syndrome | t(5;12)(q15;q24) |
| Holt-Oram syndrome | t(2;8;12)(2qter-->2q22.2::8p23.1-->8p11.1::12q15--> 12q23::8p11.1-->8qter;8pter-->8p23.1::12q23--> 12q24.31::2p15-->2q22.2::12q24.31-->12qter), t(2;10)(p15;q11.2), t(10;12)(q11.2;12q15) |
| Holt-Oram syndrome with lung hypolasia and cardiomyopathy | t(1;11)(p13;q13) |
| Huntington disease (HD) | t(4;5)(q21;p15.3)mat |
| Hypergonadotropic hypogonadism, azoospermia and minor dysmorphic features | inv ins(2;4)(2pter->2p24::4q28.3->4q31.2::2p24->2qter; 4pter->4q28.3::4q31.2->4qter) |
| Hyper-IgM syndrome (HIGM) | t(X;14)(q26.3;q13.1) |
| Hypermetropia | t(11;13)(q25;q22) |
| Hypertelorism with esophageal abnrmality and hypospadias/Opitz-G/GBBB syndrome | inv(X)(p22.3q26) |
| Hypertelorism, ambiguous external genitalia, hypospadias | t(8;20)(q22.3-q23;p13) |
| Hypertelorism, epicanthus, simian crease, pes calcaneus, dilation of ureter, incomplete lobation of lung | t(5;6)(q13;p23) |
| Hypertelorism, microtia, and facial clefting syndrome (HMC) | t(1;7)(q31.2;p15.1-p15.3) |
| Hypertelorism, short palpebral fissures, small coloboma on inner eye lid, deep philtrum, micrognathia | mos t(8;12)(p23.2;q13.3) |
| Hypertension, essential | t(1;6)(q42;q21) |
| Hypertension, essential | t(4;8)(p16;p23) |
| Hypertension, essential | t(4;18)(p12;q22) |
| Hypertension, essential | t(11;21)(q23;q21)mat |
| Hyperthyroidism | t(10;18)(p11.2;q21) |
| Hypertrichosis universalis congenita, Ambras type | inv(8)(p11.2q23.1) |
| Hypofibrinogenemia | t(7;12)(p;q) |
| Hypogonadism | t(4;12)(q25;q24.2) |
| Hypogonadism | t(Y;16)(q12;q12) |
| Hypogonadism | t(1;12)(p32;q24) |
| Hypogonadism and dorsal spine stenosis | t(3;9)(q21;p13) |
| Hypogonadotropic hypogonadism (infantile testes), azoospermia, and cleft lip and palate, | t(7;8)(p12.3;p11.2) |
| Hypomagnesia with secondary hypocalcemia (HOMG) | t(X;9)(p22;q12) |
| Hypophosphatemic rickets, autosomal dominant (ADHR) | t(9;13)(q22;q14) |
| Hypoplastic external genitalia | t(X;9)(q22.3;q11.2)mat |
| Hypoplastic left heart syndrome | t(2;18;21)(q22;q21;q21)mat |

TABLE 1-continued

Translocations and Associated Disorders

| Disease or Disorder | Translocation |
| --- | --- |
| Hypoplastic left heart syndrome | t(10;11)(q24;q23) |
| Hypoplastic left heart, low-set ears, redundant neck folds, hypotelorism, epicanthus | t(6;7)(q13;p14) |
| Hypospadias | t(4;8)(p16;q22)pat |
| Hypospadias | t(13;14)(q;q) |
| Hypospadias and gynecomastia | t(13;14)(q;q) |
| Hypotonia and developmental delay | t(X;13)(q13;p11) |
| Hypotonia, seizures, strabismus, severe mental retardation | t(2;7)(q31;q36) |
| Idiopathic generalised epilepsy, IGE | t(4;6)(q35;p21)mat |
| Idiopathic hypogonadotropic hypogonadism | t(13;16)(q14.11;q24)pat |
| Idiopathic Partial Epilepsy | t(13;22)(q22.3;q11.23) |
| Idiopathic scoliosis (IS) | inv(8)(p23.2q11.21) |
| Impaired speech development, mild mental retardation and mild dysmorphic features | t(2;12)(2pter->2p25.3::2p23.3->2p25.2::2p23.3->2p14::2q14.3->2p14::2q14.3->2q14.3::12q12->12qter;12pter->12q12::2p25.3->2p25.2::2q14.3->2qter) |
| Infantile seizures, myopia, ptosis | t(11;13)(p15.4;q32.1) |
| Infantile spasm syndrome (West syndrome) | t(X;7)(p22.3;p15) |
| Infantile spasm syndrome (West syndrome) | t(X;6)(p22.3;q14) |
| Infantile spasm syndrome (West syndrome) | t(X;18)(p22;p11.2) |
| Infantile spasms | t(6;14)(q27;q13.3) |
| Infertility (female) | t(6;14)(p10;p10) |
| Infertility (female) | t(7;12)(q11.3;q14) |
| Inflammatory bowel disease | t(5;12)(q13.2;q21.2) |
| Inflammatory bowel disease | t(9;19)(q21.1;p13.1)mat |
| Inflammatory bowel disease | t(10;12)(q24;q13)pat |
| Intellectual disability, affective disorder, autism | t(4;12)(q21.3;q15)mat |
| Interventricular septal defect, facial deformities, marked psychomotor retardation | t(6;17)(p22;q22)mat |
| Intrauterine growth retardation and oligohydramnios | inv(X)(q22q28) |
| Iridogoniodys-genesis, type 1 (IRID1) (glaucoma) | t(6;13)(p25.3;q22.3) |
| Isolated growth hormone deficiency and ectopic posterior pituitary and primary amenorrhea | t(X;18)(q22.3;q23), inv (9)(p11q13) |
| IUGR, right clubfoot and microretrognathy | inv(12)(p12q22)t(12;16)(p13;q22) |
| Jacobsen syndrome (JBS) | t(6;11)(p21;q25) |
| Jejunal atresia | t(2;3)(q31.3;p24.2)mat |
| Kabuki syndrome | t(15;17)(q15;q21)mat |
| Kallmann syndrome | t(7;12)(q22;q24) |
| Kallmann syndrome with bone anomalies | t(7;9)(p14.1;q31.1) |
| Keratoconus | t(7;11)(q34;q13.3), inv(9)(p11q12) |
| Klippel-Feil anomaly and type A1 brachydactyly | t(5;17)(q11.2;q23) |
| Klippel-Trenaunay-Weber syndrome | t(5;11)(q13.3;p15.1) |
| Klippel-Trenaunay-Weber syndrome | t(8;14)(q22.3;q13) |
| Klippel-Trenaunay-Weber syndrome | inv(8)(q22.2q23.3) |
| Learning difficulties, emotionally immature, obesity, transient hypertension, possible seizure disorder, narrow palate with broad palatine ridges | t(X;10)(p22.3;q11) |
| Learning difficulties, mild bilateral hearing loss | t(9;22)(q34.13;q11.21) |
| Learning difficulties, spelling difficulties | t(14;18)(q24.2;p11.32) |
| Learning disability, celiac disease | t(1;7)(q23.2;q34) |
| Leri-Weill dyschondrosteosis | t(2;8)(q31;p21)pat |
| Lissencephaly | t(8;17)(p11.23;p13.3) |
| Lissencephaly | t(17;19)(p13.3;q13.13) |
| Lissencephaly, X-linked | t(X;2)(q22.3;p25.1) |
| Low birth weight, hypotonia, learning difficulties, pulmonary hypertension, delayed visual maturation | t(2;16)(p14;q22) |
| Low sperm motility | t(5;22)(q15;q11) |
| Lowe Oculocerebrorenal Syndrome (OCRL) | t(X;3)(q25;q27), t(14;17)(q24;q23)pat |
| Lowe Oculocerebrorenal Syndrome (OCRL) | t(X;20)(q26.1;q11.2) |
| Low-grade fibromyxoid sarcoma | t(7, 16) (q32-34;p11) or t(11, 16) (p11;p11) |
| Low-set, posteriorly rotated ears, macrostomy, coarse facial features, postaxial hexadactyly of the feet, clinodactyly of the fingers, bilateral inguinal hernia, funnel chest, bell-shaped thorax and developmental delay | t(12;17)(p13.3;q21.3) |
| Lymphedema-distichiasis syndrome | t(Y;16)(q11.2;q24.3) |
| Macrocephaly and developmental delay | t(7;10)(q33;q23) |
| Macrocephaly, multiple lipomas, and hemangiomata | t(Y;19)(q11;q13) |

TABLE 1-continued

Translocations and Associated Disorders

| Disease or Disorder | Translocation |
|---|---|
| Macrocephaly, multiple lipomas, and hemangiomata | t(10;13)(q23.2;q33) |
| Macromastia | t(1;9)(q41;q31.3) |
| Major affective disorder, MAFD1 | t(9;11)(p24;q23) |
| Major affective disorder, MAFD1 | t(14;18)(q11.2;q21.1)mat |
| Male Infertility | t(11;22)(q23.1;q11.1) |
| Male Infertility | inv(9)(p11;q12), inv(9)(pter;q12)mat |
| Male Infertility | t(6;21)(p21.1;p13)mat |
| Male infertility | t(13;16)(q14;q22) |
| Male infertility | inv(9)(p11p12) |
| Male infertility | inv(9)(p11q13) |
| Male infertility | t(1;8)(p22;q21) |
| Male infertility | inv(5)(p13q15) |
| Male infertility | t(1;14)(p11;q11) |
| Male infertility | t(5;22)(q35;q11) |
| Male infertility | inv(9)(p11q21) |
| Male infertility | t(6;9)(q21;p24) |
| Male infertility | t(1;4)(p21;q35) |
| Male infertility | t(2;3)(q23;q27) |
| Male infertility | t(2;18)(p13;q21) |
| Male infertility | t(3;13)(q27;q21) |
| Male infertility | t(4;13)(q35;q22) |
| Male infertility | inv(1)(p36q21) |
| Male infertility | t(1;22)(q11;p11)mat |
| Male Infertility | t(8;15)(q22;p11)mat |
| Male Infertility | t(1;4)(q21;q33)mat |
| Male infertility due to tail stump syndrome failure of flagella assembly) | t(5;12)(p15.1;q21.2) |
| Male subfertility and reduced testicular size | t(2;4;9)(p13;q25;p12) |
| Male Turner phenotype and heart malformations | t(5;7)(p15;q22)pat |
| Malformed ear | t(5;7)(p15.3;p11) |
| MALT lymphoma | t(11;18)(q21;q21) |
| Mantle cell lymphoma | t(11;14)(q13;q32) |
| Marfanoid habitus with skeletal anomalies | t(2;7)(q37.1;q21.3) |
| Marfanoid habitus with skeletal anomalies and generalized cartilage dysplasia | t(2;8)(q37.1;q21.2) |
| Marfanoid habitus with skeletal anomalies and generalized cartilage dysplasia | t(2;13)(q37.1;q22) |
| Marfanoid habitus, learning difficulty | t(7;8)(q22.1;q22.1) |
| Maturity onset diabetes of the young (MODY)-like diabetes | t(7;10)(q22;p12) |
| McDonough syndrome (mental retardation, peculiar facies, kyphoscoliosis, diastasis recti, cryptorchidism, and congenital heart defect) | t(X;20)(p22;q21)mat |
| Median cleft of upper lip/pedunculated skin masses | t(X;16)(q28;q11.2) |
| Megalocornea, corneal clouding, aplastic skin lesions | t(3;9)(q24;p22) |
| Melkersson-Rosenthal syndrome | t(9;21)(p11;p11) |
| Membranous cranial ossification, delayed | t(2;3)(p15;q12)mat |
| Meningioma, familial | t(14;22)(14qter-cen;22qter) |
| Menkes Disease | t(X;16)(q13.3;p11.2) |
| Menkes syndrome | t(X;2)(q13.1;q32.2) |
| Menkes syndrome | t(X;1)(q13;q12) |
| Menkes syndrome | t(X;21)(q13.3;p11.1) |
| Menkes syndrome | t(X;13)(q13.3;q14.3) |
| Mental and growth retardation with amblyopia | t(8;11)(q24.3;p15.1)pat |
| Mental and motor retardation, seizure disorder, bilateral aniridia, microcephaly | t(2;6)(q33.1;p12.2) |
| Mental Retardation | t(4;18)(q28.2;q21.3)t(18;21)(q11.2;q11.2) |
| Mental Retardation | t(2;5)(q37;q14) |
| Mental Retardation | t(1;2)(p32;q11) |
| Mental Retardation | t(1;3)(q42;q13) |
| Mental retardation and progressive ocular abnormalities | t(17;18)(q25;q21) |
| Mental Retardation and Skeletal abnormalities | t(3;13)(p23;q34), t(4;8;18)(4pter-->4q35::8q21--> qter;4qter-->4q35::8p21-->8q21::18q23--> 18qter;18pter-->18q23::8p21-->8qter) |
| Mental retardation without gross dysmorphic stigmata | der(1)(5pter->5p14::1p31->1qter), der(3)(3pter-> 3p26::1pter->1p31::3p22->3qter), der(5)(5p14-> 5q23::3p26->3p22::5q23->5qter) |
| Mental retardation, bilateral radioulnar stynostosis, agenesis of corpus callosum and several minor congenital malformations | t(12;19)(q15;q13) |
| Mental retardation, congenital malformations | t(1;13)(q24;q32) |

TABLE 1-continued

Translocations and Associated Disorders

| Disease or Disorder | Translocation |
|---|---|
| Mental retardation, delay in receptive and expressive language, bilateral hearing impairment, facial abnormalities | t(3;15)(p27;q22)pat |
| Mental retardation, developmental delay, short stature, microcephaly, dysmorphic features | inv(7)(q22.1q32.1) |
| Mental retardation, dysmorphic | t(4;10)(p15.2;q11) |
| Mental retardation, dysmorphic | t(4;9)(q22;p24)pat |
| Mental retardation, dysmorphic | t(1;4)(q43;q22) |
| Mental retardation, dysmorphic | t(1;10)(q44;q21) |
| Mental retardation, dysmorphic facies, clinodactyly | t(4;13)(q31;q14) |
| Mental retardation, facial deformity | t(2;10)(q14;q22)mat |
| Mental retardation, Microcephaly, brachycephaly, Large fontanelle, Hypertelorism, Short stature-postnatal, Clinodactyly of 5th finger, syndactyly | t(1;15)(p22;q26) |
| Mental retardation, micropthalmia | t(10;12)(q24;q13.2)mat |
| Mental retardation, scoliosis, skin pigmentation distrbance | t(X;13)(q13;q31) |
| Mental retardation, seizures and tall stature | t(X;9)(q12;p13.3) |
| Mental retardation, short stature, facial dysmorphism and hydronephrosis | t(5;16;20)(5pter->5q11.2::16q12.1->16q23::20p11.2->20pter;16pter->16q12.1::5q11.2->5qter;16qter->16q23::20p11.2->20qter) |
| Mental retardation, X-linked 60 (MRX60) | t(X;12)(q11;q15) |
| Mental retardation/developmental delay, microcephaly, ear malformations, flat/broad nose, bulbous nasal tip | t(7;9)(q36;q34)mat |
| Mesomelic dysplasia, Kantaputra type | t(2;8)(q31;p21)pat |
| Mesomelic form of chondrodysplasia and congenial glaucoma | t(13;18)(q14;q23) |
| Michelin tyre syndrome with distinctive facial dysmorphia, submucous cleft palate, lateral clefting of the mouth, genital and dental anomalies and moderate developmental delay | inv(7)(q22q31.3)mat |
| Microbrachycephaly, deformed ears, hypoplasia of hands and feet, dysplastic nails, clinodactyly, hypertelorism, high palate, profound mental deficiency, motor retardation | t(1;17)(q12;q25) |
| Microcephaly and retardation | t(1;2)(p10;p10), t(5;7)(q21;q31) |
| Microcephaly, backward sloping forehead, hypertonia, continuous choriform movements, spastic tetraparesis, severe mental retardation | (2pter->2p25.2::2p21->2q11.2::2p21->2p23.1::2q11.2->2qter) (3pter->3p21.1::3p12.2->3q29::2p23.1->2p15.2::3p12.2->3p21.1::3q29->3qter) |
| microcephaly, microphthalmia, microcornea and prognathism (MMEP) | t(6;13)(q21;q12) |
| Microcephaly, short stature, peculiar facies and mental retardation | t(2;7)(2pter-->2q23::7p15-->7pter; 2qter-->2q23::7q112-->7p15::7q112-->7qter), t(5;20)(5pter-->5q11::20q11-->20qter; 20-pter-->20q11::5q11-->5qter)mat |
| Microphthalmia (bilateral) with cataracts | inv(2)(p21q31) |
| Microphthalmia (bilateral) with colobomatous orbital cyst | t(3;5)(q27;q11.2) |
| Microphthalmia (bilateral) with mental retardation and cerebral palsy | t(2;6)(q31;q24) |
| Microphthalmia, diaphragmatic hernia and tetralogy of fallot | t(1;15)(q41;q21.2) |
| Micropthalmia-Cataract | t(2;16)(p22.3;p13.3) |
| Migraine | t(1;8)(p36.3;p11.2)mat |
| Mild campomelic dysplasia with Robin sequence | t(4;17)(q28.3;q24.3) |
| Mild developmental delay, seizures | t(13;14)(q;q) |
| Mild intellectual disability, obesity, coarse facies, and apparent synophrys | t(3;12)(3qter->3q26.31::12q22->12q21?::12q23.1->12q23.1::3p22.3->3p24.1::12q23.1->12q22::12q21?->12q14.1::3q26.31->3p22.3::12q23.1->12qter;12pter->12q14.1::3p24.1->3pter), t(11;21)(p14.1;q22.11) |
| Mild learning disability | t(2;10)(q11.2;q22.3) |
| Mild mental impairment, compulsive and obsessive behaviour | t(2;10)(q24;q22) |
| Mild mental retardation | t(X;15)(q28;p11.2) |
| Mild mental retardation | t(X;5)(p11.1;q31.1)mat |
| Mild Mental Retardation and dysmorphic features | t(5;18)(q21.3;q21.32) |
| Mild mental retardation, bilateral enlargement of sternocleidomastoid muscles, hoarse vice, minor toe abnormalities, obesity | t(X;9)(q28;q21) |

TABLE 1-continued

Translocations and Associated Disorders

| Disease or Disorder | Translocation |
|---|---|
| Mild mental retardation, odd facies, bilateral epicanthal folds, bilateral clinodactyly, metatarsus varus deformity | t(2;4;7)(7;8)(q14;q31;q11q22;q13) |
| Mild MR (IQ 69), macrocephaly (OFC > 98th percentile) and aggressive behavior. | t(13;21)(q22;q22.1) |
| Mild retardation, convergence insufficiency | t(10q−;22p+) |
| Mild to moderate mental retardation (MR) and minor facial anomalies | t(18;20)(q21.1;q11.2) |
| Minor congenital malformations | t(6;8)(q13;q22) |
| Minor craniofacial dysmorphism, hypotonia, hearing loss, gustatory flushing syndrome, and severe developmental delays | inv(2)(p13q11.2) |
| Minor dysmorphic stigmata, moderate mental retardation and an expressive aphasia. | der(4)t(4;10)(q35;p14)inv(4)(p16q21), der(10)t(4;10), t(13;14)(q;q) |
| Minor multiple congenital anomalies | t(6;12)(p21.3;q24.31) |
| Minor multiple congenital anomalies | inv(11)(q21q23.3) |
| Minor multiple congenital anomalies and mental retardation | t(4;12)(q21.1;p11.2) |
| Minor multiple congenital anomalies and mental retardation | t(5;8)(p15.1;q21.2) |
| Minor multiple congenital anomalies and mental retardation | t(10;17)(q22.1;p13.1) |
| Minor multiple congenital anomalies and mental retardation | inv(3)(p11.2q26.1) |
| Moderate learning difficulties, numeracy problems | t(4;14)(q31.22;q11.2) |
| Moderate mental retardation | t(7;11)(q11.2;p11.2) |
| Moderate mental retardation, piebaldism | inv(4)(p16q12) |
| Moderate multiple congenital anomalies | t(3;14)(q26.2;q22) |
| Moderate multiple congenital anomalies and mental retardation | t(3;16)(q21;p13.1) |
| Moderate multiple congenital anomalies and mental retardation | t(5;9)(q11.2;q34.1) |
| Moderate multiple congenital anomalies and mental retardation | t(Y;9)(11.23;q34.3) |
| Moderate retardation | t(2q−;8q+)pat |
| Moderate retardation, autism | inv(5)(pq) |
| Moderate retardation, club foot | t(1p−;8q+) |
| Moderate retardation, height < 3rd percentile | inv(Y)(pq)pat |
| Moderate retardation, narrow palpebral fissures, narrow palate, club foot | t(9p−;17p+)pat |
| Moderate retardation, ptosis, facial asymmetry, short 4th metatarsals | t(6q−;17q+) |
| Moebius syndrome 1 (MBS1) | t(1;13)(p34;q13) |
| Moebius syndrome 1 (MBS1) | t(1;11)(p22;p13)pat |
| Moebius syndrome 1 (MBS1) | t(1;2)(p22.3;q21.1) |
| Mowat-Wilson syndrome | t(2;12;18)(q22.3;q22;q21.33) |
| Mowat-Wilson syndrome | t(1;2)(q24.1;q31.1) |
| Mucopolysaccharidosis II (Hunter's disease) | t(X;5)(q26-q27;q31-q32) |
| Mucopolysaccharidosis type IIIA (Sanfilippo syndrome A) | t(1;21)(p31;q22) |
| Mucopolysaccharidosis type IIIC (Sanfilippo syndrome C) | t(14;21)mat |
| Mullerian aplasia | t(12;14)(q;q) |
| Multiple anomalies (large head, vision defect, omphalocele, heart defect, enlarged kidneys, moderate MR, speech defect, mild transient homocysteinemia) | t(17;20)(p13.3;q13.33) |
| Multiple anomalies including: open metopic suture, midline cleft palate, micrognathia, tetralogy of Fallot variant with high ventricular septal defect, atretic pulmonic valve, hypoplastic pulmonary artery, duplication of vagina and uterus. | t(X;17)(q11;q11) |
| Multiple anomalies, precocious puberty, mild to moderate mental retardation, exostoses | der(6)t(6;10)(q21;q26.13)inv(6)(p24.2q21), der(10)t(6;10) |
| Multiple congenital abnormalities | t(X;9)(p;q) |
| Multiple congenital abnormalities (mental retardation, athetotic tetraplegia, microcephaly, peculiar facies, clinodactyly of the fifth fingers and overlapping toes) | t(5;14)(q21;q32) |
| Multiple congenital abnormalities, including macrocephaly, facial dysmorphism and agenesis of corpus callosum | mos, t(7;11)(q36;p11) |
| Multiple congenital anomalies and mental retardation (MCA/MR) | t(1;2)(p22;q22) |

TABLE 1-continued

Translocations and Associated Disorders

| Disease or Disorder | Translocation |
|---|---|
| Multiple congenital anomalies and mental retardation (MCA/MR) | t(X;15)(p11;q11) |
| Multiple congenital anomalies and mental retardation (MCA/MR) | t(X;21)(p11;p11) |
| Multiple congenital anomalies and mental retardation (MCA/MR) | t(X;9)(p22;q12) |
| Multiple congenital anomalies and mental retardation (MCA/MR) | t(X;18)(p;q) |
| Multiple congenital anomalies and mental retardation (MCA/MR) | t(2;12)(p25;q21) |
| Multiple congenital malformations and minor abnormalities characteristic of 13q- and 21q- syndromes | t(13;21)(q22;q22) |
| Multiple Exostoses | t(8;13)(q23;q31) |
| Multiple Exostoses | t(8;11)(q24.11;p15.5) |
| Multiple Exostoses | inv(8)(p23q24) |
| Multiple Exostoses | t(8;19)(q24.11;q13.13) |
| Multiple exostoses, autism, mental retardation, epilepsy | t(X;8)(p22.13;q22.1) |
| Multiple sclerosis | t(12;13)(p12.1;q21) |
| Multiple congenital anomalies syndrome of microcephaly, unilateral corneal staphyloma, hypoplastic thumbs, ectrodactyly, brachydactyly, syndactyly | t(1;6;7;3;11)(11;22;21) (1qter->1p22::11p15->11pter;6qter->6p21::1p22->1pter;7qter->7p15::6p21->6pter;3pter->3q27::7p15->7pter;3qter->3q27::11p15->11q11::21q11->21qter;22qter->22p11::11q11->11qter;21pter->21q11::22p11->22pter) |
| Myasthenic syndrome, slow-channel congenital (SCCMS) | t(2;9)(q31;p27) |
| Myelodysplastic syndrome with erythroid hypoplasia | t(3;14)(p21.1;q24.1) |
| Myoclonic epilepsy | t(5;11)(p11;p15) |
| Myopathy, congenital, with fiber-type disproportion | t(10;17)(p11.2;q25)mat |
| Myopia | t(12;18)(q21;p11.2) |
| Myopia | t(17;19)(q21;q13)mat |
| Myopia | t(9;18)(p24;q12) |
| Myopia and cataracts | t(18;20)(p11.2;p11.2) |
| Myotonic dystrophy | t(2;20)(p21;q11) |
| Myotonic dystrophy | t(5;8) |
| Nager acrofacial dysostosis | t(X;9)(p22.1;q32)mat |
| Nail dysplasia (twenty-nail dystrophy) | t(6;10)(q13;p13)mat |
| Nail-Patella syndrome (NPS) | t(9;17)(q34.1;q25) |
| Nail-Patella syndrome (NPS) | t(1;9)(q32.1;q34) |
| Neuroblastoma | t(1;17)(p36.2;q11.2) |
| Neurofibromatosis type 1 (NF1) | t(17;22)(q11.2; q11.2) |
| Neurofibromatosis type 1 (NF1) | t(14;17)(q32;q11.2) |
| Neurofibromatosis type 2(NF2) | t(X;22)(p11.2;q11.2) |
| Neurofibromatosis type 2(NF2) | t(4;22)(q12;q12.2)pat |
| Neurofibromatosis type 2(NF2) | t(1;22)(p36.1;q12)pat |
| No fetal limbs, no evidence of spine, cystic area in caudal region, abnormal head shape | t(9;18)(q22.3;q11) |
| Noninsulin-dependent diabetes mellitus (NIDDM, Type 2) | t(3;9)(p21.31;q33.1)mat |
| Noninsulin-dependent diabetes mellitus (NIDDM, Type 2) | t(3;20)(p21.2;q12)mat |
| Noninsulin-dependent diabetes mellitus (NIDDM, Type 2) | t(X;1)(q27;q24) |
| Non-specific dysmorhism, small hands, bilateral hernias, tremor, delayed puberty | t(5;6)(q14.3;q25.1) |
| Non-specific dysmorphism, slim hands and feet, high arched palate, clinodactyly | t(1;20)(q31.3;q13.32) |
| Nonsyndromic mental retardation | t(2;7)(q24.1;q36.1) |
| Non-syndromic mental retardation | t(1;17)(p36.3;p11.2) |
| Non-syndromic X-linked mental retardation (MRX) | t(X;21)(p11.2;q22.3) |
| Non-syndromic X-linked mental retardation (MRX) | t(X;2)(p11.4;p21.3) |
| Non-syndromic X-linked mental retardation (MRX) | t(X;7)(q24;q22) |
| Non-syndromic X-linked mental retardation (MRX) | t(X;21)(q26;p11)mat |
| Non-syndromic X-linked mental retardation (MRX) | t(X;8)(q28;q12)mat |
| Non-syndromic X-linked mental retardation (MRX) | t(X;7)(p11.3;p11.21) |
| Non-syndromic X-linked mental retardation (MRX) | inv(X)(p11.1q13.1)mat |

TABLE 1-continued

Translocations and Associated Disorders

| Disease or Disorder | Translocation |
|---|---|
| Non-syndromic X-linked mental retardation (MRX) | inv(X)(q13.1q28)mat |
| Non-syndromic X-linked mental retardation (MRX) | inv(X)(p21.3q27.1)mat |
| Non-syndromic X-linked mental retardation (MRX) | t(X;17)(p11.3;p13.3) |
| Non-syndromic X-linked mental retardation (MRX) | t(X;20)(p11;q13.3) |
| Non-syndromic X-linked mental retardation (MRX) | inv(X)(p11.2q21.3)mat |
| Non-syndromic X-linked mental retardation (MRX) | t(X;15)(q13.3;cen) |
| Norrie disease | t(X;10)(p11;p14) |
| Norrie disease | t(X;6)(p11.2;q13) |
| Nystagmus 2, Congenital (NYS2) | t(5;16)(q31.3;p13.5) |
| Nystagmus 2, Congenital (NYS2) | t(7;15)(p11.2;q11.2)mat |
| Obesity | t(4;15)(q22.3;q21.3) |
| Obesity | t(7;20)(q11.2;q13.2) |
| Obesity | t(11;18)(q23.3;q21) |
| Obesity | t(12;17)(q24.1;q25) |
| Oblique facial clefts (bilateral), calcaneovarus foot deformity, severe bilateral ocular hypoplasia | t(1;22)(q21;q12) |
| Oculoauriculovertebral spectrum (OAVS) | t(9;18)(p23;q12.2) |
| Oculocutaneous albinism, type II (OCA2) | t(2;4)(q31.2;q31.22) |
| Oesophageal atresia and psychomotor retardation | t(6;15)(p11.2;p12) |
| Oligodendroglioma and oligoastrocytoma | t(1;19)(q10;p10) |
| Oligomenorrhoea/ovarian dysfunction | t(X;9)(q24;q34) |
| Oligomenorrhoea/ovarian dysfunction | t(X;8)(q21;p23) |
| Omphalocele | t(3;4)(q28;p14) |
| Omphalocele | inv(5)(p13q15) |
| Opitz trigonocephaly C syndrome | t(3;18)(q13.13;q12.1) |
| Ornithine transcarbamylase deficiency | t(X;5)(p21.1;q11) |
| Orofacial Cleft 1 | t(6;7)(p23;q36.1) |
| Orofacial Cleft 1 | t(6;9)(p23;q22.3)mat |
| Orofacial Cleft 1 | t(2;19)(q11.2;q13.3) |
| Orofacial Cleft 1 | inv(8)(p23q11) |
| Orofacial Cleft 1 | t(6;9)(p24;p23) |
| Orofacial Cleft 1 | t(9;17)(q32;q12) |
| Orofacial Cleft 1 with hypospadias | inv(4)(p13q21.1)pat |
| Osteoporosis | t(4;12)(p15.3;q22) |
| Osteosclerotic chondrodysplasia, lethal, with intracellular inclusions | t(4;11)(q23;q13) |
| Osteosclerotic chondrodysplasia, lethal, with intracellular inclusions | inv(4)(p16q13)mat |
| Ovarian dysgenesis and amenorrhoea | t(X;5)(q21;q11) |
| Ovarian dysgenesis and amenorrhoea | t(X;17)(p10;q10) |
| Ovarian dysgenesis and primary amenorrhoea | t(X;9)(q22;q22) |
| Ovarian dysgenesis and primary amenorrhoea | t(X;2)(q21;p25) |
| Ovarian dysgenesis and primary amenorrhoea | t(6;15)(p21.3;q15) |
| Ovarian dysgenesis and primary amenorrhoea | t(1;11)(q31;q25) |
| Ovarian dysgenesis and primary amenorrhoea | t(X;3)(q13;p25) |
| Ovarian dysgenesis and primary amenorrhoea | t(X;11)(q22;q13) |
| Ovarian dysgenesis and primary amenorrhoea | t(X;15)(q21;q23) |
| Ovarian dysgenesis and primary amenorrhoea | t(X;4)(q21;q13) |
| Ovarian dysgenesis and primary amenorrhoea | t(X;15)(q;p) |
| Ovarian dysgenesis and primary amenorrhoea | t(X;12)(q;q) |
| Ovarian dysgenesis and primary amenorrhoea | t(X;1)(q24;p36) |
| Ovarian dysgenesis and primary amenorrhoea | t(X;3)(q22;p11) |
| Ovarian dysgenesis and primary amenorrhoea | t(X;6)(q21;q27) |
| Ovarian dysgenesis and primary amenorrhoea | t(X;12)(q21;q24) |
| Ovarian dysgenesis and primary amenorrhoea | t(X;2)(q21;p25) |
| Ovarian dysgenesis and primary amenorrhoea | t(X;22)(q22;q13) |
| Ovarian dysgenesis and primary amenorrhoea | t(X;C)(q;q) |
| Ovarian dysgenesis and primary amenorrhoea | t(X;21)(q;q) |
| Ovarian dysgenesis and primary amenorrhoea | t(X;5)(q;q) |
| Ovarian dysgenesis and primary amenorrhoea | t(X;19)(q;q) |
| Ovarian dysgenesis and secondary amenorrhoea | t(X;4)(q26;q21) |
| Ovarian dysgenesis and secondary amenorrhoea | t(X;12)(q21;p13) |
| Ovarian dysgenesis and secondary amenorrhoea | t(X;15)(q21;q26) |
| Ovarian dysgenesis and secondary amenorrhoea | t(X;9)(q21;q33) |

TABLE 1-continued

Translocations and Associated Disorders

| Disease or Disorder | Translocation |
|---|---|
| Ovarian dysgenesis and secondary amenorrhoea | t(8;9)(p11.2;q12) |
| Ovarian dysgenesis and secondary amenorrhoea | t(X;12)(q21;pter) |
| Ovarian dysgenesis and secondary amenorrhoea | t(X;1)(q13;p13) |
| Ovarian dysgenesis and secondary amenorrhoea | t(X;9)(q21;p24) |
| Ovarian dysgenesis and secondary amenorrhoea | t(X;7)(q21;p22) |
| Ovarian dysgenesis and secondary amenorrhoea | t(X;1)(q13;p13) |
| Ovarian dysgenesis and secondary amenorrhoea | t(X;19)(q13;q13) |
| Overgrowth and acromegaloidism with normal growth hormone secretion | inv(11)(p15.3q23.3) |
| Panhypopituitarism | t(11;22)(q24;q13) |
| Papillary thyroid cancer | t(10;(various))(q11;(various)) |
| Papillorenal syndrome | t(10;13)(q24.3;q12.3) |
| Parkinson disease | t(1;18)(p36.2;q21.2) |
| Partial DiGeorge syndrome (facial dysmorphism, hypoparathyroidism, renal agenesis, mental retardation), single kidney, bilateral cataracts and multiple exostoses | ins(8;10)(8pter->8q13::10p14->10p13::8q24.1->8qter)ins(10;8)(10pter->10p14::8q24.1->8q13::10p13->10qter) |
| Partial frontal lobe epilepsy and cognitive impairment | t(2;13)(q24;q31) |
| Peculiar sperm defects | t(10;15)(q26;q12) |
| Pelizaeus-Merzbacher disease (PMD) moderate mental retardation and cerebellar ataxia associated with dysmyelination. | inv(X)(p22.3q22)mat |
| Penoscrotal hypospadias, anal atresia with a recto-urethral fistula and a hypoplastic kidney | t(6;17)(p21.31;q11.2) |
| Pernicious puberty | t(1;9)(p31.1;q31.3) |
| Pervasive developmental disorder and abnormal facial features | t(X;4)(p11;q13) |
| Pervasive developmental disorder, distinctive facies, bifid uvula, strabismus, and joint laxity. | der(8)(10pter->10p12.32::8p12->8qter), der(10)(8pter->8p21.3::10p12.32->10p11.23::8p21.3->8p12::10p11.23->10qter) |
| Peters anomaly | t(1;7)(q41;p21)mat |
| Peters anomaly | t(8;9)(q22.1;q21.13) |
| Peters Anomaly associated with multiple midline defects (cranial meningocele, cardiac defects and cleft lip and palate) | inv(4)(q12q13.3) |
| Peters-plus syndrome | t(2;15)(q21;q26.1) |
| Pharmacoresistant epileptic encephalopathy | t(Y;4)(q11.2;q21) |
| Phenotypically normal at birth. Growth and motor delay at age 30 months. Delayed speech and development at age 2 years | t(6;11)(p21;q21), t(11;21) (q21;p13), inv(6)(p21q11) |
| Phenylketonuria | t(3;12)(p21;q24.1)mat |
| Pierre Robin Sequence | t(5;17)(q15;q23)pat |
| Pierre Robin sequence (PRS) | t(3;15)(p25;q22)pat |
| Pierre Robin sequence (PRS) | t(2;17)(q24.1;q24.3) |
| Pierre Robin sequence (PRS) | t(2;17)(q32.1;q24.3) |
| Pierre Robin Sequence (PRS) | t(2;17)(q23.3;q24.3) |
| Pierre Robin sequence with pectus excavatum and rib and scapular anomalies | t(13;17)(q22.1;q23.3) |
| Pierre-Robin sequence, hypoplasia of right ventricle with muscular hypertrophy, endocardial fibroelastosishypoplastic lungs, dysplastic left kidney, bilateral pelvicalyceal dilatation, central nervous system periventricular heterotopias and club foot | t(17;20)(q21.1;p11.21)mat, t(17;20)(q21.1;p11.21)pat |
| Polycystic kidneys | t(16;22)(p13.3;q11.21)mat |
| Polyhydramnios, severe hypotonia, poor respiratory effect, mild syndactyly, clinodactyly | t(X;16)(q11.2;p13.11) |
| Polymicrogyria | t(2;7)(q35;p22) |
| Poor growth, gastroesophageal reflux disease, peripheral pulmonic stenosis, omphalocele, high myopia, severe mental retardation, microcephaly, abnormal facies, kyphosis, brachydactyly and hypertonia | t(1;12)(p22.3;q21.3), der(6)(pter->p23::q21->q22.3::q21->p23::q22.3->qter), t(7;18)(q11.2;q21.2) |
| Postaxial polydactyly, Type A | inv(7)(p15q36) |
| Prader-willi syndrome | t(15;19)(q12;q13.41) |
| Prader-willi syndrome | t(4;15)(q27;q11.2)pat |
| Prader-willi syndrome | t(3;15)(q29;q11) |
| Prader-willi syndrome | t(14;15)(p11;q11)mat |

TABLE 1-continued

Translocations and Associated Disorders

| Disease or Disorder | Translocation |
| --- | --- |
| Prader-willi syndrome | t(5;15)(p15.3;q12)/t(8;15)(q24.3;q12)/<br>t(12;15)(q24.3;q12) |
| Prader-Willi syndrome | t(4;15)(q27;q11) |
| Prader-Willi syndrome | t(9;15)(q21;q12-q13) |
| Prader-Willi syndrome | t(X;15)(q28;q12) |
| Prader-Willi syndrome | t(8;15)(q24.1;q21.2)mat |
| Prader-Willi syndrome | t(2;15)(p11;q11.2)mat |
| Prader-Willi syndrome (atypical) | t(2;15)(q37.2;q11.2) |
| Premature baby with left renal agenesis, right low functional kidney, altered chemical-clinical parameters, neutropenia, recurrent pulmonary infections, long bone diaphysis broadening, growth and developmental delay. | t(2;7)(p13;p12) |
| Premature Menopause | t(X;11)(q21.31;q14.1) |
| Premature ovarian failure | t(X;1)(q21;p34) |
| Premature ovarian failure | t(X;2)(q21;q23) |
| Premature ovarian failure | t(X;2;8)(q21.2;q14.2;p11.1) |
| Premature ovarian failure | t(X;12)(q21;p13) |
| Premature ovarian failure | t(X;19)(q21;p22) |
| Premature ovarian failure | t(X;9)(q21;q22) |
| Premature ovarian failure | t(X;9)(q21;q34) |
| Premature ovarian failure | t(X;12)(q21;p13) |
| Premature ovarian failure | t(X;15)(q21;q26) |
| Premature ovarian failure | t(X;9)(q21;q33) |
| Premature ovarian failure | t(X;2)(q21;p25) |
| Premature ovarian failure | t(X;5)(q22;q11.2)mat |
| Premature ovarian failure | t(2;15)(q32.3;q13;3)pat |
| Premature ovarian failure | t(2;11) |
| Premature ovarian failure | t(13;14) |
| Premature ovarian failure | t(X;1)(q24;q43) |
| Premature ovarian failure | t(X;7)(q21.3;p22) |
| Premature ovarian failure | t(X;19)(q21.3;p13.3) |
| Premature ovarian failure | t(X;11)(q25;q23) |
| Premature ovarian failure | t(X;15)(q25;q21) |
| Premature ovarian failure | t(X;20)(q24;q12) |
| Premature ovarian failure | t(X;6)(q13-q21;p12) |
| Premature ovarian failure | t(X;22)(q24;q13) |
| Premature ovarian failure | t(X;1)(q21.1;q32) |
| Premature ovarian failure | t(X;9)(q21.3;q21.2) |
| Prenatal ultrasound revealed IUGR, hectic abnormal movements and retrognathia | t(4;11;12, 13)(4pter->4q25::11p14->11p14::4q25-><br>4q27::13p13->13pter; 11qter->11p14::4q33->4qter;<br>12pter->12q13::4q27->4q32::12q13->12qter; 13qter-><br>13p12::4q33->4q32::11p14->11pter) |
| Primary amenorrhoea | t(X;4)(p21.1;p16.2) |
| Primary amenorrhoea | t(X;9)(q22;q12) |
| Primary amenorrhoea | t(X;15)(q13;p12) |
| Primary amenorrhoea | t(X;22)(q23;q23) |
| Primary amenorrhoea and primary hyperparathyroidism | t(X;2)(q22;p13) |
| Primary amenorrhoea, ovarian dysgenesis and hypothalmic dysfunction | t(X;9)(p22;q11) |
| Primary microcephaly | t(1;4)(q31;p15.3) |
| Profound retardation, convulsive disorder, strabismus, scoliosis | t(2;11)(p;p) |
| Profound retardation, microcephaly, overbite malocclusion, epicanthal fold, midline ventral hernia, simian line | t(3;18)(p;q) |
| Psoriasis | t(4;11)(q21.3;q25)pat |
| Psoriasis | t(7;11)(q11.23;q13.5) |
| Psoriasis | t(1;11)(p36.3;q12.2)mat |
| Psoriasis vulgaris | t(2;4)(p25;q31.1) |
| Psychomotor delay, esotropia, simian creases, high arched palate, hallux valgus, plantar valgus abnormalities, abnormally shaped head, hyperreflexia, athetoid movements | t(3;9)(3;18) (p27;q29;p22;q21) |
| Psychomotor retardation, ataxic gait, strabismus and mild myopia. | t(10;13)(q22.3;p13) |
| Psychomotor retardation, dysmorphia and hydronephrosis | t(6;15)(p24;q21), t(13;14)(q31;q21) |
| Pterygium syndrome | t(6;7)(q15;q32) |
| Ptosis, epicanthal folds, depressed nasal bridge, carp-shaped mouth, low set ears, hirsutism, pectus excavatum, developmental and language delay | t(1;21;10;7)(7qter->7q31::1p21->1qter;21pter-><br>21q11.2::1p21->1pter;10pter->10q11.2::7q21-><br>7q31::21q21->21qter;7pter->7q21::10q11.2->10qter) |

TABLE 1-continued

Translocations and Associated Disorders

| Disease or Disorder | Translocation |
|---|---|
| Radioulnar synostosis and vertebral fusions without any carpal, digital or tarsal involvement and broad ribs and clavicles | t(10;20)(p12;p13) |
| Red cell dimorphism | t(11;22)(p15.5;q11.21) |
| Regression of milestones | t(11;21)(p13;q22)pat |
| Renal cancer | t(6;16)(q16.1;q21) |
| Renal cell carcinoma 1 (RCC1) | t(3;8)(p14.2;q24.1) |
| Renal cell carcinoma 1 (RCC1) | t(3;12)(q13.2;q24.1) |
| Retinal cone dystrophy | t(1;6)(q44;q27) |
| Retinoblastoma | t(2;13)(p24.3;q14.2) |
| Retinoblastoma | t(5;13)(q22;q14) |
| Retinoblastoma | t(2;9)(q11;p11) |
| Retinoblastoma | t(1;13)(p22;q12) |
| Retinoblastoma | t(X;13)(q12;q31) |
| Retinoblastoma | t(13;18)(q141;q122) |
| Retinoblastoma | t(X;13)(q23;q13) |
| Retinoblastoma | t(X;13)(p22;q12) |
| Retinoblastoma | t(X;13)(p22;q12) |
| Rett syndrome | t(X;22)(p11.22;p11)mat |
| Rett syndrome | t(X;3)(p21.3;q13.31) |
| Rett syndrome | inv(2)(p25.3q21.3) |
| Rett syndrome | t(16;17)(p13;q21) |
| Rett-like syndrome | t(1;7)(p13.3;q31.3) |
| Rieger syndrome | t(4;12)(q25;q15) |
| Rieger syndrome | t(1;4)(q23.1;q25) |
| Rieger syndrome | t(4;11)(q27;q21) |
| Rieger syndrome | t(4;16)(q26;q22)mat |
| Rubinstein-Taybi syndrome | t(2;16)(p13.3;p13.3) |
| Rubinstein-Taybi syndrome | t(7;16)(q34;p13.3) |
| Rubinstein-Taybi syndrome | t(2;16)(q36.3;p13.3) |
| Rubinstein-Taybi syndrome | inv(16)(p13.3q13) |
| Rubinstein-Taybi syndrome (RTS) | t(2;16)(q36.3;p13.3) |
| Saethre-Chotzen syndrome | t(7;10)(p21;q21.2)pat |
| Saethre-Chotzen syndrome | t(2;7)(p23;p22)mat |
| Saethre-Chotzen syndrome | t(7;18)(p21.2;q23) |
| Saethre-Chotzen syndrome | t(2;7)(q21.1;p21.2)pat |
| Saethre-Chotzen syndrome | t(5;7)(p15.3;p21.2) |
| Saethre-Chotzen syndrome | t(6;7)(q16.2;p15.3) |
| Saethre-Chotzen syndrome | t(7;8)(p21;q13) |
| Saethre-Chotzen syndrome | inv(7)(p21.3q34) |
| Schizophrenia | t(1;11)(q42.1;q14.3) |
| Schizophrenia | t(6;11)(q14.2;q25) |
| Schizophrenia | t(9;14)(q34;q13)mat |
| Schizophrenia | t(2;18)(p11.2;p11.2)pat |
| Schizophrenia | t(18;21)(p11.1;p11.1) |
| Schizophrenia | t(2;18)(q21;q23)mat |
| Schizophrenia | inv(18)(p11.3q21.1) |
| Schizophrenia | t(4;13)(p16.1;q21.31) |
| Schizophrenia | inv(18)(p11.31q21.2) |
| Schizophrenia | t(1;11)(q42.1;q14.3) |
| Scoliosis, hirsutism, learning problems, and developmental delay | t(X;15)(p22.2;q26.1) |
| Severe brachydactyly and syndactyly, mental retardation, hypoplasia of the cerebellum, scoliosis, and ectopic anus | t(2;10)(q31.1;q26.3) |
| Severe cognitive disability associated with complete agenesis of the corpus callosum and microcephaly | der(2)t(2;14)(p22;q12), der(14)t(2;14)(p22;q12) inv(14)(q12q12) |
| Severe developmental delay, mental retardation, profound hearing loss, partial blindness, gynecomastia, nystagmus | t(3;7)(q27;p21.2) |
| Severe epilepsy, developmental delay, mild dysmorphism | t(2;18)(q21;q22) |
| Severe intellectual and developmental retardation with no dysmorphic features other than strabismus and down-turned angles of the mouth. | t(1;16)(q12;p13.3) |
| Severe lower eyelid colobomas, malar and mandibular hypoplasia, bilateral microtia with external auditory canal atreasia, dysplastic ossicles, hearing loss, bilateral choanal stenosis, cleft palate, several oral frenula of the upper lip and micrognathia | t(2;17)(q24.3;q23) |
| Severe mental handicap | t(5;6)(q14.3;q25.1) |
| Severe mental retardation and multiple congenital anomalies | t(3;7)(p21.3;q11.2) |

TABLE 1-continued

Translocations and Associated Disorders

| Disease or Disorder | Translocation |
|---|---|
| Severe mental retardation | inv(X)(p22.3q13.2) |
| Severe mental retardation and microcephaly with neurologic manifestations of hypertonic quadriplegia | der(2, 14, 21)t(2;14)(p11;q13)ins(21;14)(q11;q11q13) |
| Severe mental retardation and multiple congenital abnormalities, including congenital heart disease, cryptorchidism and infantilism, rocker bottom feet and eye abnormalities | der(3)(3pter->3p14::3q12->3q26::5q14->5q34::3p14->3q12::5q34->5qter), der(5)(5pter->5q14::3q26->3qter) |
| Severe mental retardation and osteosclerosis | t(4;15)(p15;q15), t(5;12)(q35;q15) |
| Severe mental retardation, muscular hypotonia, seizures, bilateral sensorineural hearing loss, submucous cleft palate, persistent ductus Botalli, unilateral cystic kidney dysplasia and frequent infections. | t(11;20)(p15.4;q13.2) |
| Severe multiple congenital anomalies and mental retardation | t(3;15)(p25;q15) |
| Severe multiple congenital anomalies and mental retardation | t(7;16)(p11.2;p11.2) |
| Severe multiple congenital anomalies and mental retardation | t(2;16)(q23;q24) OR t(2;16)(q22;q23.2) |
| Severe myoclonic epilepsy of infancy | t(2;5)(q24.3;q34) |
| Severe psychomotor retardation | t(5;12)(q15;p13) |
| Severe retardation, autism | t(4p+;9q-) |
| Severe retardation, macrocephaly, bilateral overfolded pinnae, elbow contractures, clinodactyly, seizures | t(X;20)(p10;q10) |
| Severe retardation, microcephaly, overbite malocclusion, strabismus, kyphosis | t(2;6)(p10;q10) |
| Severe short stature, haemolytic anaemia, recurrent hypoglycemia | t(3;4)(q23;q31.22) |
| Short adult stature, severe intrauterine growth retardation (IUGR) at birth, atypical diabetes | t(1;11)(p36.22;p15.5) |
| Short palpebral fissures, hypertelorism, microgenia, hydrocephalus internus, hypoplasia of the cerebellum and bulbi olfactorii, bilateral hypoplastic lungs, cardiac abnormalities, right proximal ureterostenosis, hypoplastic gall bladder | inv(2)(p21q11) |
| Short stature, short neck, cubitus valgus | t(X;15)(p22;p1) |
| Short stature/features of Turner's | t(X;Y)(p22.3;q11) |
| Short stature/features of Turner's | t(X;Y)(p22;q11)mat |
| Short-limb dwarfism and hypertrophic cardiomyopathy | idic(14)(p11) |
| Short-rib polydactyly syndrome (Majewski syndrome) | inv(4)(p16q13)mat |
| Shwachman-Diamond syndrome | t(6;12)(q16.2;q21.2) |
| Silver-Russell syndrome | t(17;20)(q25;q13)pat |
| Silver-Russell syndrome | t(1;17)(q24;q23-q24) |
| Silver-Russell syndrome | inv(7)(p11.2q22) |
| Silver-Russell syndrome | inv(7)(p11.2q11.21) |
| Silver-Russell syndrome | inv(7)(p11.2q36) |
| Silver-Russell syndrome | inv(7)(p14p21) |
| Silver-Russell syndrome | t(7;16)(q21;q24)mat |
| Silver-Russell syndrome | t(11;16)(p13;q24.3)pat |
| Simpson-Golabi-Behmel syndrome, type 1 (SGBS1) | t(X;1)(q26;q12) |
| Sirenomelia | t(2;6)(p22.3;q12) |
| Situs Ambiguus | t(X;1)(q26;p13.1) |
| Situs ambiguus, asplenia and corrected transposition of the great arteries | t(X;21)(q26;p13) |
| Small stature, prognathism, quadrantanopsia with abnormal carotid arteriography and uretero-renal reflux | t(5;19)(q12;p or q11)pat |
| Smith-Lemli-Opitz syndrome (SLOS) | t(7;20)(q32.1;q13.2) |
| Sotos syndrome | t(3;6)(p21;p21) |
| Sotos syndrome | t(5;15)(q35;q22) |
| Sotos syndrome | t(5;8)(q35;q24.1) |
| Sotos syndrome | t(2;12)(q33.3;q15)mat |
| Spastic paraparesis | t(5;9)(p12;q21.11) |
| Specific language impairment (SLI) | t(2;7)(p23;q31.3) |
| Specific language impairment (SLI) | t(5;7)(q22;q31.2) |
| Specific Language Impairment (SLI) | t(7;13)(q31.2;q13.2) |
| Specific language impairment and verbal apraxia | t(1;2)(q;q) |
| Specific Language Impairment (SLI) (spastic dysarthria and apraxia of speech) | t(7;13)(q31.1;q13.2) |

TABLE 1-continued

Translocations and Associated Disorders

| Disease or Disorder | Translocation |
|---|---|
| Spherocytosis, hereditary (HS) | t(8;12)(p11;p13) |
| Spherocytosis, hereditary (HS) | inv(8)(p22q21)mat |
| Spherocytosis, hereditary (HS) | t(3;8) |
| Spina Bifida, X-linked | t(X;22)(q27;q12) |
| Spinal muscular atrophy | t(4;10)(qter;q24.1)mat |
| Spinocerebellar ataxia (SCA)27 | t(5;13)(q31.2;q33.1) |
| Split hand/foot malformation with long bone deficiency (SHFLD) | t(2;18)(q14.2;p11.2) |
| Split hand/split foot malformation, deafness and mental retardation | inv(1)(q21q32), t(4;7)(q31.1;q21.3), inv(11)(p15.1q23) |
| Split-hand/foot malformation 1 (SHFM1) | t(2;7)(q21.1;q22.1) |
| Split-hand/foot malformation 1 (SHFM1) | inv(7)(q22q21.3) |
| Spondylocostal dysostosis | t(7;22)(q32;q11) |
| Spondylocostal dysostosis with anal atresia and urogenital anomalies | t(6;9)(p12;q12)mat |
| Sporadic Incontinentia pigmenti (IP1)/Hypomelanosis of Ito | t(X;17)(p11.2;p11.2) |
| Sporadic Incontinentia pigmenti (IP1)/Hypomelanosis of Ito | t(X;9)(p11.21;q33.2) |
| Sporadic Incontinentia pigmenti (IP1)/Hypomelanosis of Ito | t(X;13)(p11.21;q12.3) |
| Sporadic Incontinentia pigmenti (IP1)/Hypomelanosis of Ito | t(X;10)(p11.2;q22) |
| Sporadic Incontinentia pigmenti (IP1)/Hypomelanosis of Ito | t(X;18)(p11;q23) |
| Sporadic Incontinentia pigmenti (IP1)/Hypomelanosis of Ito | t(X;10)(p11.2;q11)mat |
| Sporadic Incontinentia pigmenti (IP1)/Hypomelanosis of Ito | t(X;5)(p11.2;q35.2) |
| Sporadic Incontinentia pigmenti (IP1)/Hypomelanosis of Ito | t(X;13)(q10;q10) |
| Sporadic incontinentia pigmenti and bilateral retinoblastoma | t(X;13)(p11.21;q12.3) |
| Stickler syndrome | t(5;17)(q15;q23) |
| Supravalvular aortic stenosis/William's syndrome | t(6;7)(q27;q11.23) |
| Symmetrical upper limb peromelia and lower limb phocomelia | t(2;12)(p25.1;q24.1) |
| Synovial sarcoma | t(X;18)(p11.2;q11.2) |
| Tachycardia, paroxysmal | t(3;22)(p21;q13) |
| Tachycardia, paroxysmal | t(1;21)(q42;q22) |
| Temtamy-like syndrome | t(2;9)(p24;q32) |
| Test | t(1;9)(q31;p13) |
| Testicular atrophy | t(5;12)(q11.1;q11) |
| Testicular dysgenesis | t(2;7)(p21;q11) |
| Testicular dysgenesis | t(7;8)(p11;q21) |
| Tetralogy of Fallot, coronal hypospadias, dysmorphic facies | t(2;6)(p22.2;q23.1) |
| Tetramelic mirror-image polydactyly | t(2;14)(p23.3;q13) |
| Thanatophoric dysplasia (TD) | t(1;10)(q42;q11.2) |
| Thyroid dysgenesis | t(1;17)(q25;q21)mat |
| Toriello-Carey syndrome (TCS) | t(2;14)(q33;q22) |
| Torticollis, keloids, cryptorchidism and renal dysplasia (TKCR) | t(X;3)(q28;q21) |
| Torticollis, keloids, cryptorchidism and renal dysplasia (TKCR) | t(X;10)(q28;q11) |
| Total anomalous pulmonary venous return (TAPVR) | t(10;21)(q23.1;q11.2) |
| Townes-Brocks syndrome (TBS) | t(5;16)(p15.3;q12.1) |
| Townes-Brocks syndrome (TBS) | inv(16)(p11.2q12.1)pat |
| Treacher Collins syndrome | t(5;13)(q11;p11) |
| Treacher Collins syndrome | t(6;16)(p21.31;p13.11)mat |
| Triangular face, epicanthus, midface hypoplasia, small mouth with thin vermillion border, low-set ears, hypermobile joints, unsteady gait, dystonic movement disorder, speech defect | t(5;10)(q35.2;q11.2) |
| Trichiasis, entropion with corneal abrasions, strabismus, progressive thinning of the scalp hair, sensorineural hearing impairment, mild learning difficulties and inguinal hernias | t(11;18)(p13;q21)mat |
| Tricho-rhino-phalangeal syndrome, type 1 (TRPS1) | t(9;11)(p22;q21) |
| Tricho-rhino-phalangeal syndrome, type 1 (TRPS1) | t(8;18)(q24.11;q23) |

TABLE 1-continued

Translocations and Associated Disorders

| Disease or Disorder | Translocation |
|---|---|
| Tricho-rhino-phalangeal syndrome, type 1 (TRPS1) | t(8;9)(q24.11;q33.3) |
| Tricho-rhino-phalangeal syndrome, type 1 (TRPS1) | t(3;8;11)(q13;p22q13;p12q21) |
| Tricho-rhino-phalangeal syndrome, type 1 (TRPS1) | inv(8)(p21q24.1) |
| Two-chambered heart and other abnormalities | t(14;22)(q24;q11.2) |
| Ulnar ray defect | t(6;7)(q21;q31.2) |
| Unilateral cryptorchidism | t(8;9)(q21;q23) |
| Unilateral cryptorchidism | t(10;11)(p13;p11) |
| Unilateral cryptorchidism | t(1;2)(q25;q22) |
| Unilateral cryptorchidism, bilateral hallux valgus feet | t(2;4)(q21;p12) |
| Unilateral cryptorchidism, pyloric stenosis | inv(2)(p11q13) |
| Vaginal uterine agenesis with amastia | t(8;13)(q22.1;q32.1) |
| Various congenital anomalies including sensorineural hearing loss, Mondini defect, mild subcutaneous atrophy, avascular necrosis of left femoral head, a telangiectatic skin condition with recurrent ulceration, and juvenile rheumatoid arthritis | t(8;9)(q12.1;p21.3)de novo, t(9;11)(q33;q13)mat |
| Ventricular septal defect (VSD), cleft palate, XY sex reversal, hydronephrosis | t(10;11)(q24.2;p12) |
| Ventricular septal defect, hydronephrosis, diaphragmatic hernia | t(5;6)(q33;q25) |
| Waardenburg syndrome, type I | inv(2)(q35q37.3) |
| Waardenburg syndrome, type I | t(1;8)(q32.3;q24.1), t(4;7)(7pter-->p13::7q34-->q31.2::4p15.2-->qter);(7qter-->q34::7p13-->q31.2::4p15.2-->pter) |
| Waardenburg syndrome, type IIC | t(4;8)(p16;p23) |
| Walker-Warburg syndrome | t(5;6)(q35;q21) |
| Williams-Beuren syndrome (WBS) | t(7;16)(q11.23;q13) |
| Williams-Beuren syndrome (WBS) | t(6;7)(p21.1;q11.23) |
| Wilms tumour | t(5;11)(q11;p13) |
| Wilms tumour | t(9;12)(q22.3;q15) |
| Wilms Tumour | t(5;6)(q21;q21) |
| Wilms Tumour, facial dysmorphism and a thick corpus callosum | t(7;19)(q11.2;q13.3) |
| Wilms Tumour, malformative syndrome, mental retardation | t(7;13)(q36;q13) |
| Wilms tumour, skeletal abnormalities similar to thrombocytopenia and absent radii (TAR) syndrome | t(1;7)(q42.13;p14.3) |
| X linked mental retardation | t(X;19)(p11.2;p13.3) |
| X-linked mental retardation | t(X;8)(p11.2;p22.3) |
| X-linked mental retardation and sensory hyperarousal | inv(X)(q11.1q27.3) |
| Zellweger syndrome | inv(7)(p12q11.23) |
| Zimmermann-Laband syndrome | t(3;8)(p21.2;q24.3)mat |

A chromosome alteration sometimes is associated with medical condition (e.g., Table 1). An outcome determinative of a chromosome alteration is sometimes an outcome determinative of the presence or absence of a condition (e.g., a medical condition), disease, syndrome or abnormality, or includes, detection of a condition, disease, syndrome or abnormality (e.g., non-limiting examples listed in Table 1). In certain embodiments a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis). Analysis and processing of data can provide one or more outcomes. The term "outcome" as used herein can refer to a result of data processing that facilitates determining the presence or absence of a chromosome alteration (e.g., a translocation, a deletion). In certain embodiments the term "outcome" as used herein refers to a conclusion that predicts and/or determines the presence or absence of a chromosome alteration (e.g., a translocation, a deletion). In certain embodiments the term "outcome" as used herein refers to a conclusion that predicts and/or determines a risk or probability of the presence or absence of a chromosome alteration (e.g., a translocation) in a subject (e.g., a fetus). A diagnosis sometimes comprises use of an outcome. For example, a health practitioner may analyze an outcome and provide a diagnosis bases on, or based in part on, the outcome. In some embodiments, determination, detection or diagnosis of a condition, syndrome or abnormality (e.g., listed in Table 1) comprises use of an outcome determinative of the presence or absence of a chromosome alteration. In some embodiments, an outcome based on discordant read pairs, mapping characteristics and identification of breakpoints is determinative of the presence or absence of a chromosome alteration. In certain embodiments, an outcome generated utilizing one or more methods or a system described herein is determinative of the presence or absence of one or more conditions, syndromes or abnormalities listed in Table 1. In certain embodiments a diagnosis comprises a determination of a presence or absence of a condition, syndrome or abnormality. Often a diagnosis comprises a determination of a chromosome alteration as the nature and/or cause of a condition, syndrome or abnormality. In certain embodiments an outcome is not a diagnosis. An outcome often comprises one or more numerical values generated using a processing method described herein in the context of one or more considerations of probability. A consideration of risk or probability can include, but is not limited to: an uncertainty value, a measure of variability, confidence level, sensitivity, specificity, standard deviation, coefficient of variation (CV) and/or confidence level, Z-scores, Chi values, Phi values, ploidy values, fitted fetal fraction, area ratios, median level, the like or combinations thereof. A consideration of probability can facilitate determining whether a subject is at risk of having, or has, a chromosome alteration, and an outcome determinative of a presence or absence of a genetic disorder often includes such a consideration.

An outcome sometimes is a phenotype. An outcome sometimes is a phenotype with an associated level of confidence (e.g., an uncertainty value, e.g., a fetus is positive for Autism with a confidence level of 99%; a pregnant female is carrying a male fetus with a confidence level of 95%; a test subject is negative for a cancer associated with a chromosome alteration at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular chromosome alteration is present or absent in a subject/sample. The value of a score may be used to determine, for example, a variation, difference, or ratio of mapped sequence reads that may correspond to a chromosome alteration. For example, calculating a positive score for a selected chromosome alteration or portion from a data set, with respect to a reference genome can lead to an identification of the presence or absence of a chromosome alteration, which chromosome alteration sometimes is associated with a medical condition (e.g., cancer, autism and the like). In some embodiments, an outcome comprises a level, a profile and/or a plot (e.g., a profile plot). In those embodiments in which an outcome comprises a profile, a suitable profile or combination of profiles can be used for an outcome. Non-limiting examples of profiles that can be used for an outcome include z-score profiles, p-value profiles, chi value profiles, phi value profiles, the like, and combinations thereof A health care professional, or other qualified individual, receiving a report comprising one or more outcomes determinative of the presence or absence of a chromosome alteration can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the chromosome alteration based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by a communication means, a written and/or graphical representation comprising an outcome, which upon review allows a healthcare professional or other qualified individual to make a determination as to the presence or absence of a chromosome alteration in a test subject or patient. The report may be generated by a computer or by human data entry, and can be communicated using electronic means (e.g., over the internet, via computer, via fax, from one network location to another location at the same or different physical sites), or by a other method of sending or receiving data (e.g., mail service, courier service and the like). In some embodiments the outcome is transmitted to a health care professional in a suitable medium, including, without limitation, by a non-transitory computer readable storage medium and/or in verbal, document, or file form. The file may be, for example, but not limited to, an auditory file, a non-transitory computer readable file, a paper file, a laboratory file or a medical record file.

The term "providing an outcome" and grammatical equivalents thereof, as used herein also can refer to a method for obtaining such information, including, without limitation, obtaining the information from a laboratory (e.g., a laboratory file). A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

In some embodiments, an outcome can be provided to a health care professional, physician or qualified individual from a laboratory and the health care professional, physician or qualified individual can make a diagnosis based on the outcome. In some embodiments, an outcome can be provided to a health care professional, physician or qualified individual from a laboratory and the health care professional, physician or qualified individual can make a diagnosis based, in part, on the outcome along with additional data and/or information and other outcomes.

A healthcare professional or qualified individual, can provide a suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing.

Laboratory personnel (e.g., a laboratory manager) can analyze values (e.g., a number of reads of a test sample, a number of reads of a reference, level of deviation) underlying a determination of the presence or absence of a chromosome alteration. For calls pertaining to presence or absence of a chromosome alteration that are close or questionable, laboratory personnel can re-order the same test, and/or order a different test (e.g., karyotyping and/or amniocentesis in the case of some fetal chromosome alterations), that makes use of the same or different sample nucleic acid from a test subject.

An outcome typically is provided to a health care professional (e.g., laboratory technician or manager; physician or assistant). Often an outcome is provided by an outcome module. An outcome module may comprise a suitable statistical software package. In certain embodiments an outcome is provided by a plotting module. Often a suitable statistical software comprises a suitable plotting module. In some embodiments an outcome module generates and/or compares Z-scores.

In some embodiments a plotting module processes and/or transforms data and/or information into a suitable visual medium, non-limiting examples of which include a chart, plot, graph, the like or combinations thereof. In some embodiments a plotting module processes, transforms and/or transfers data and/or information for presentation on a suitable display (e.g., a monitor, LED, LCD, CRT, the like or combinations thereof), a printer (e.g., a printed paper display), a suitable peripheral or device. In certain embodiments a plotting module provides a visual display of a relationship and/or an outcome.

In certain embodiments an outcome is provided on a peripheral or component of a machine or machine. For example, sometimes an outcome is provided by a printer or display. In some embodiments, an outcome determinative of the presence or absence of a chromosome alteration and/or an associated disease or disorder is provided to a healthcare professional in the form of a report, and in certain embodiments the report comprises a display of an outcome value and an associated confidence parameter. Generally, an outcome can be displayed in a suitable format that facilitates determination of the presence or absence of a chromosome alteration and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described herein.

Data Filtering and Processing

In some embodiments, one or more processing steps can comprise one or more filtering steps. The term "filtering" as used herein refers to removing a portion of data or a set of data from consideration and retaining a subset of data. Sequence reads can be selected for removal based on any suitable criteria, including but not limited to redundant data (e.g., redundant or overlapping mapped reads), non-informative data, over represented or underrepresented sequences, noisy data, the like, or combinations of the foregoing. A filtering process often involves removing one or more reads and/or read pairs (e.g., discordant read pairs) from consideration. Reducing the number of read, pairs of reads and/or reads comprising candidate breakpoints from a data set analyzed for the presence or absence of a chromosome alteration often reduces the complexity and/or dimensionality of a data set, and sometimes increases the speed of searching for and/or identifying chromosome alterations by two or more orders of magnitude.

In some embodiments a system or method described herein comprises filtering reads, discordant read mates and/or discordant reads pairs. Filtering can be performed before or after identifying discordant read mates, characterizing the mappability of a plurality of sequence read subsequences, providing a change in mappability, selecting a subset of the discordant read mates, identifying candidate breakpoints, comparing subsets of reads, comparing candidate breakpoints, identifying breakpoints, or comparing a number of discordant read mates from the sample to a reference. Filtering often is performed prior to determining the presence or absence of one or more chromosome alterations.

Filtering is often performed by a system or module. A system or module that performs filtering is referred to herein as a filter or a filtering module. In some embodiments a filtering module comprises code (e.g., script) written in S or R that utilizes a suitable package (e.g., an S package, an R package). For example a filter module may comprise and utilize one or more SAMtools (SAMtools [online], [retrieved on 2013 Sep. 25], retrieved from the internet at world wide web uniform resource locator: samtools.sourceforge.net). For example, the sum of all applicable flags can be used to identify concordant reads where a selection of concordant or PCR duplicate reads is "if (bitwiseA==83|| bitwiseA==163|| bitwiseA==99|| bitwiseA==147|| bitwiseA>=1024)" where bitwiseA is the sum of all applicable flags in a SAM formatted file.

A filter often accepts a set of data (e.g., a set of reads) as input and outputs a subset of filtered data (e.g., a subset of reads, e.g., filtered reads). In certain embodiments reads that are removed in a filtering process are often discarded and/or removed from further analysis (e.g., statistical analysis). Filtering often comprises removing reads from a set of reads. In some embodiments filtering comprises removing one or both read mates of a discordant read pair. In some embodiments filtering comprises removing a plurality of reads from a set of reads. Sometimes no reads are removed in a filtering step.

Filtering often removes, discards or rejects certain reads from a data set according to a predetermined conditional query. For example, sometimes a filter receives input reads from a system or another module, performs a filtering function on the received reads and accepts only those input reads that satisfy a condition. In some embodiments a filter receives input reads from a system or another module, performs a filtering function and removes, discards or rejects only those input reads that satisfy a condition. In some embodiments a conditional query comprises a Yes/No or a True/False determination. For example, a "True" or "Yes" value is sometimes assigned to one or more reads where a condition of a query is met and a "False" or "No" value is assigned to reads where a condition of a query is not met.

In some embodiments filtering comprises removing, rejecting and/or discarding non-discordant reads (e.g., concordant reads). In some embodiments a conditional query of a filter (e.g., 20) comprises a determination of the presence or absence of a discordant paired read. In some embodiments paired reads that are not discordant are removed, rejected and/or discarded. In some embodiments paired reads that are not discordant are assigned a "False" or "No" value and are removed, rejected by a module and/or discarded. In some embodiments non-discordant reads are not allowed to pass through a filter 20. In some embodiments non-discordant reads are deleted, moved to a trash file or temporary file (e.g., 10), or retained in their original data location and/or format. In certain embodiments discordant paired reads are identified and/or are retained in an output subset of filtered reads. In certain embodiments discordant paired reads are identified and are forwarded to another module or filter. In some embodiments discordant paired reads are identified, assigned a "True" or "Yes" value, and are retained in an output subset of filtered reads (e.g., discordant read pairs). In some embodiments discordant reads are accepted and passed through a filter 20. Reads can be filtered according to the presence or absence of discordant and/or non-discordant reads by a discordant read identifying module (e.g., filter 20). A discordant read identifying module sometimes comprises a filter configured to remove, reject and/or discarding non-discordant reads.

In some embodiments filtering comprises removing, rejecting and/or discarding reads that are exact duplicates. Duplicate reads are referred to herein as PCR duplicates. In some embodiments a conditional query of a filter (e.g., 30) comprises a determination of the presence or absence of PCR duplicates. In some embodiments PCR duplicates are assigned a "True" or "Yes" value and are removed, rejected by a module and/or discarded. In some embodiments PCR duplicates are not allowed to pass through a filter 30. In some embodiments PCR duplicates are deleted, moved to a trash file or temporary file (e.g., 10), or retained in their original data location and/or format. A representative read of a set of duplicate reads is herein referred to as a "representative read". In some embodiments representative reads and unique reads are retained in an output subset of filtered reads. Representative reads and unique reads are often identified and/or are forwarded to another module or filter. In some embodiments representative reads and unique reads are identified, assigned a "False" or "No" value, and are retained in an output subset of filtered reads. In some embodiments representative reads and unique reads are accepted into a filter (e.g., 30) and/or are passed through a filter (e.g., 30). Reads can be filtered according to PCR duplicates by a PCR duplicate filter (e.g., filter 30). A filter module sometimes comprises a PCR duplicate filter.

In some embodiments filtering comprises removing, rejecting and/or discarding reads of low sequencing quality. Reads of low sequencing quality are often reads with a PHRED score equal to or less than about 40, about 35, about 30, about 25, about 20, about 15, about 10, or about 5. In some embodiments a conditional query of a filter (e.g., 40) comprises a determination of the presence or absence of reads of low sequencing quality. In some embodiments reads of low sequencing quality are assigned a "True" or "Yes" value and are removed, rejected by a module and/or discarded. In some embodiments reads of low sequencing quality are not allowed to pass through a filter 40. In some embodiments reads of low sequencing quality are deleted, moved to a trash file or temporary file (e.g., 10), or retained in their original data location and/or format. Reads that are not of low quality (e.g., high quality reads) are sometimes retained in an output subset of filtered reads. Reads that are not of low quality are often identified and/or are forwarded to another module or filter. In some embodiments reads that are not of low quality are identified, assigned a "False" or "No" value, and are retained in an output subset of filtered reads. In some embodiments reads that are not of low quality are accepted into a filter (e.g., 40) and/or are passed through a filter (e.g., 40). Reads can be filtered according to sequencing quality by a sequencing quality filter (e.g., filter 40). A filter module sometimes comprises a sequencing quality filter.

In some embodiments filtering comprises removing, rejecting and/or discarding a read where sequence read subsequences of a read comprise a mapping discontinuity. A mapping discontinuity often refers to sequence read subsequences of a read where 3 or more (e.g., >2) fragments map to different (e.g., unexpected) locations on a reference genome (e.g., reads comprising step-wise multiple alignments). A mapping discontinuity sometimes refers to 3 or more in silica fragment of a read that map to (i) different chromosomes (e.g., 3 or more different chromosomes), (ii) different locations where each location is separated by more than a predetermined fragment size (e.g., more than 300 bp, more than 500 bp, more than 1000 bp, more than 5000 bp, or more than 10,000 bp), (iii) different and/or opposite orientation, the like or a combination thereof. For example a mapping discontinuity can refer to sequence read subsequences where two fragments map to opposite orientations and a third fragment maps to a different chromosome. In some embodiments a conditional query of a filter (e.g., 60) comprises a determination of the presence or absence of a read comprising a mapping discontinuity. In some embodiments reads comprising a mapping discontinuity are assigned a "True" or "Yes" value and are removed, rejected by a module and/or discarded. In some embodiments reads comprising a mapping discontinuity are not allowed to pass through a filter 60. In some embodiments reads comprising a mapping discontinuity are deleted, moved to a trash file or temporary file (e.g., 10), or retained in their original data location and/or format. Reads that do not comprise a mapping discontinuity are sometimes retained in an output subset of filtered reads. Reads that do not comprise a mapping discontinuity are often identified and/or are forwarded to another module or filter. In some embodiments reads that do not comprise a mapping discontinuity are identified, assigned a "False" or "No" value, and are retained in an output subset of filtered reads. In some embodiments reads that do not comprise a mapping discontinuity are accepted into a filter (e.g., 60) and/or are passed through a filter (e.g., 60). Reads can be filtered according to a mapping discontinuity by a mapping discontinuity filter (e.g., filter 60). A filter module sometimes comprises a mapping discontinuity filter.

In some embodiments filtering comprises removing, rejecting and/or discarding a reads comprising sequence read subsequences that are unmappable. In some embodiments filtering comprises removing, rejecting and or discarding a read comprising one or more, greater than 2, greater than 3, greater than 4, greater than 5, greater than 6, greater than 7, greater than 8, greater than 9, greater than 10, greater than 11, greater than 12, greater than 13, greater than 14, or greater than 15 sequence read subsequences that are unmappable. Unmappable refers to an inability to unambiguously map a polynucleotide to a location of a reference genome (e.g., a human reference genome). In some embodiments a conditional query of a filter (e.g., 70) comprises a determination of the presence or absence of a read comprising sequence read subsequences that are unmappable. In some embodiments reads comprising sequence read subsequences that are unmappable are assigned a "True" or "Yes" value and are removed, rejected by a module and/or discarded. In some embodiments reads comprising sequence read subsequences that are unmappable are not allowed to pass through a filter 70. In some embodiments reads comprising sequence read subsequences that are unmappable are deleted, moved to a trash file or temporary file (e.g., 10), or retained in their original data location and/or format. Reads that do not comprise sequence read subsequences that are unmappable are sometimes retained in an output subset of filtered reads. Reads that do not comprise sequence read subsequences that are unmappable are often identified and/or are forwarded to another module or filter. In some embodiments reads that do not comprise sequence read subsequences that are unmappable are identified, assigned a "False" or "No" value, and are retained in an output subset of filtered reads. In some embodiments reads that do not comprise sequence read subsequences that are unmappable are accepted into a filter (e.g., 70) and/or are passed through a filter (e.g., 70). Reads can be filtered according to sequence read subsequences that are unmappable by a mapping filter (e.g., filter 70). A filter module sometimes comprises a mapping filter.

In some embodiments filtering comprises removing, rejecting and/or discarding reads comprising sequence read subsequences that map to mitochondrial DNA. In some embodiments filtering comprises removing, rejecting and or discarding a read comprising one or more, greater than 2, greater than 3, greater than 4, greater than 5, greater than 6, greater than 7, greater than 8, greater than 9, greater than 10, greater than 11, greater than 12, greater than 13, greater than 14, or greater than 15 sequence read subsequences that map to mitochondrial DNA. In some embodiments a conditional query of a filter (e.g., 80) comprises a determination of the presence or absence of a read comprising sequence read subsequences that map to mitochondrial DNA. In some embodiments reads comprising sequence read subsequences that map to mitochondrial DNA are assigned a "True" or "Yes" value and are removed, rejected by a module and/or discarded. In some embodiments reads comprising sequence read subsequences that map to mitochondrial DNA are not allowed to pass through a filter 80. In some embodiments reads comprising sequence read subsequences that map to mitochondrial DNA are deleted, moved to a trash file or temporary file (e.g., 10), or retained in their original data location and/or format. Reads that do not comprise sequence read subsequences that map to mitochondrial DNA are sometimes retained in an output subset of filtered reads. Reads that do not comprise sequence read subsequences that map to mitochondrial DNA are often identified and/or are forwarded to another module or filter. In some embodiments reads that do not comprise sequence read subsequences that map to mitochondrial DNA are identified, assigned a "False" or "No" value, and are retained in an output subset of filtered reads. In some embodiments reads that do not comprise sequence read subsequences that map to mitochondrial DNA are accepted into a filter (e.g., 80) and/or are passed through a filter (e.g., 80). Reads can be filtered according to sequence read subsequences that map to mitochondrial DNA by a mitochondrial filter (e.g., filter 80). A filter module sometimes comprises a mitochondrial filter.

In some embodiments filtering comprises removing, rejecting and/or discarding reads comprising sequence read subsequences that map to centromere DNA. In some embodiments filtering comprises removing, rejecting and or discarding a read comprising one or more, greater than 2, greater than 3, greater than 4, greater than 5, greater than 6, greater than 7, greater than 8, greater than 9, greater than 10, greater than 11, greater than 12, greater than 13, greater than 14, or greater than 15 sequence read subsequences that map to centromere DNA. In some embodiments a conditional query of a filter comprises a determination of the presence or absence of a read comprising sequence read subsequences that map to centromere DNA. In some embodiments reads comprising sequence read subsequences that map to centromere DNA are assigned a "True" or "Yes" value and are removed, rejected by a module and/or discarded. In some embodiments reads comprising sequence read subsequences that map to centromere DNA are not allowed to pass through a filter. In some embodiments reads comprising sequence read subsequences that map to centromere DNA are deleted, moved to a trash file or temporary file (e.g., 10), or retained in their original data location and/or format. Reads that do not comprise sequence read subsequences that map to centromere DNA are sometimes retained in an output subset of filtered reads. Reads that do not comprise sequence read subsequences that map to centromere DNA are often identified and/or are forwarded to another module or filter. In some embodiments reads that do not comprise sequence read subsequences that map to centromere DNA are identified, assigned a "False" or "No" value, and are retained in an output subset of filtered reads. In some embodiments reads that do not comprise sequence read subsequences that map to centromere DNA are accepted into a filter and/or are passed through a filter. Reads can be filtered according to sequence read subsequences that map to centromere DNA by a centromere DNA filter. A filter module sometimes comprises a centromere DNA filter.

In some embodiments filtering comprises removing, rejecting and/or discarding reads comprising sequence read subsequences that map to repetitive elements. In some embodiments filtering comprises removing, rejecting and or discarding a read comprising one or more, greater than 2, greater than 3, greater than 4, greater than 5, greater than 6, greater than 7, greater than 8, greater than 9, greater than 10, greater than 11, greater than 12, greater than 13, greater than 14, or greater than 15 sequence read subsequences that map to repetitive elements. In some embodiments a conditional query of a filter (e.g., 110) comprises a determination of the presence or absence of a read comprising sequence read subsequences that map to repetitive elements. In some embodiments reads comprising sequence read subsequences that map to repetitive elements are assigned a "True" or "Yes" value and are removed, rejected by a module and/or discarded. In some embodiments reads comprising sequence read subsequences that map to repetitive elements are not allowed to pass through a filter 110. In some embodiments reads comprising sequence read subsequences that map to repetitive elements are deleted, moved to a trash file or temporary file (e.g., 10), or retained in their original data location and/or format. Reads that do not comprise sequence read subsequences that map to repetitive elements are sometimes retained in an output subset of filtered reads. Reads that do not comprise sequence read subsequences that map to repetitive elements are often identified and/or are forwarded to another module or filter. In some embodiments reads that do not comprise sequence read subsequences that map to repetitive elements are identified, assigned a "False" or "No" value, and are retained in an output subset of filtered reads. In some embodiments reads that do not comprise sequence read subsequences that map to repetitive elements are accepted into a filter (e.g., 110) and/or are passed through a filter (e.g., 110). Reads can be filtered according to sequence read subsequences that map to repetitive elements by a repetitive element filter (e.g., filter 110). A filter module sometimes comprises a repetitive element filter.

In some embodiments filtering comprises removing, rejecting and/or discarding reads comprising a singleton event. In some embodiments a conditional query of a filter (e.g., 100) comprises a determination of the presence or absence of a singleton event. A "singleton event" as used herein refers to a read or a pair of discordant reads comprising a first candidate breakpoint, where a substantially similar candidate breakpoint (e.g., a candidate breakpoint that is substantially similar to the first candidate breakpoint) is not identified and/or is not present in any other read obtained from a sample. In some embodiments a singleton event is assigned a "True" or "Yes" value and is removed, rejected and/or discarded. In some embodiments singleton events are not allowed to pass through a filter 100. In some embodiments singleton events are deleted, moved to a trash file or temporary file (e.g., 10), or retained in their original data location and/or format. Reads that are not singleton events are sometimes retained in an output subset (e.g., a selected subset) of filtered reads. Reads that are not singleton events are often identified and/or forwarded to another module or filter. Reads that are not singleton events are identified, assigned a "False" or "No" value, and are retained in an output subset (e.g., a selected subset) of filtered reads. In some embodiments reads that are not singleton events are accepted into a filter (e.g., 100) and/or are passed through a filter (e.g., 100). Reads can be filtered according to the presence or absence of a singleton event by a singleton event filter (e.g., filter 100). A filter module sometimes comprises a singleton event filter.

In some embodiments filtering comprises removing, rejecting and/or discarding a subset of reads of a sample comprising a substantially similar breakpoint or a substantially similar candidate breakpoint as found in a subset of reads from a reference. In some embodiments a subset of reads of a sample comprising a substantially similar breakpoint or a substantially similar candidate breakpoint as found in a subset of reads from a reference is assigned a "True" or "Yes" value and is removed, rejected and/or discarded. In some embodiments a subset of reads of a sample comprising a substantially similar breakpoint or a substantially similar candidate breakpoint as found in a subset of reads from a reference are not allowed to pass through a filter. In some embodiments a subset of reads of a sample comprising a substantially similar breakpoint or a substantially similar candidate breakpoint as found in a subset of reads from a reference are deleted, moved to a trash file or temporary file (e.g., 10), or retained in their original data location and/or format. A subset of reads of a sample comprising a candidate breakpoint or a breakpoint not found and/or not present in a subset of reads from a reference are sometimes retained in an output subset (e.g., a selected subset). A subset of reads of a sample comprising a candidate breakpoint or a breakpoint not found and/or not present in a subset of reads from a reference are often identified and/or forwarded to another module or filter. A subset of reads of a sample comprising a candidate breakpoint or a breakpoint not found and/or not present in a subset of reads from a reference are often identified, assigned a "False" or "No" value, and are retained in an output subset (e.g., a selected subset). In some embodiments a subset of reads of a sample comprising a candidate breakpoint or a breakpoint not found and/or not present in a subset of reads from a reference are accepted into a filter and/or are passed through a filter. A subset of reads of a sample can be filtered according to the presence or absence of a subset of reads comprising a candidate breakpoint or a breakpoint found in a subset of reads from a reference by breakpoint filter. A filter module sometimes comprises a breakpoint filter.

Figure 6:
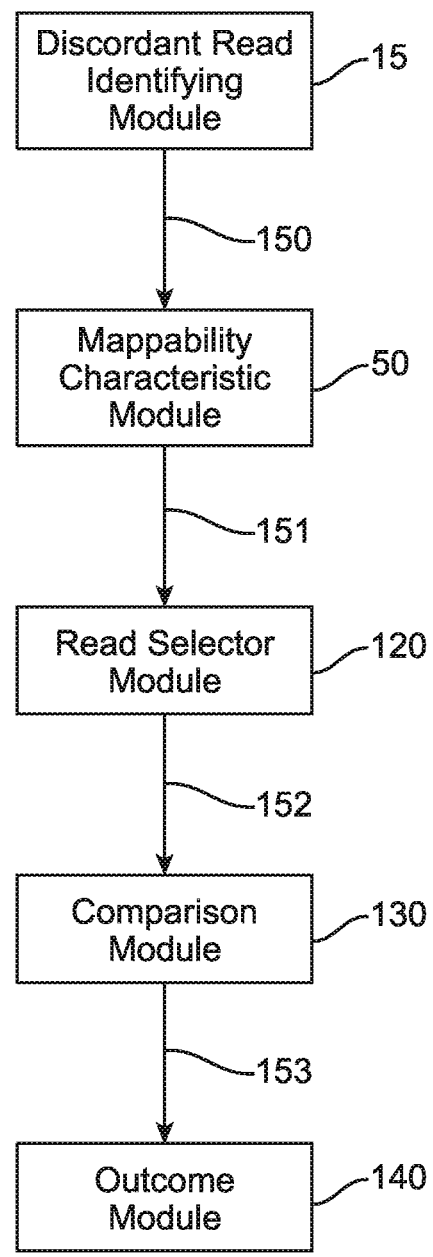
FIG. 6 shows an illustrative embodiment of a system in which certain embodiments of the technology may be implemented.
Figure 7:
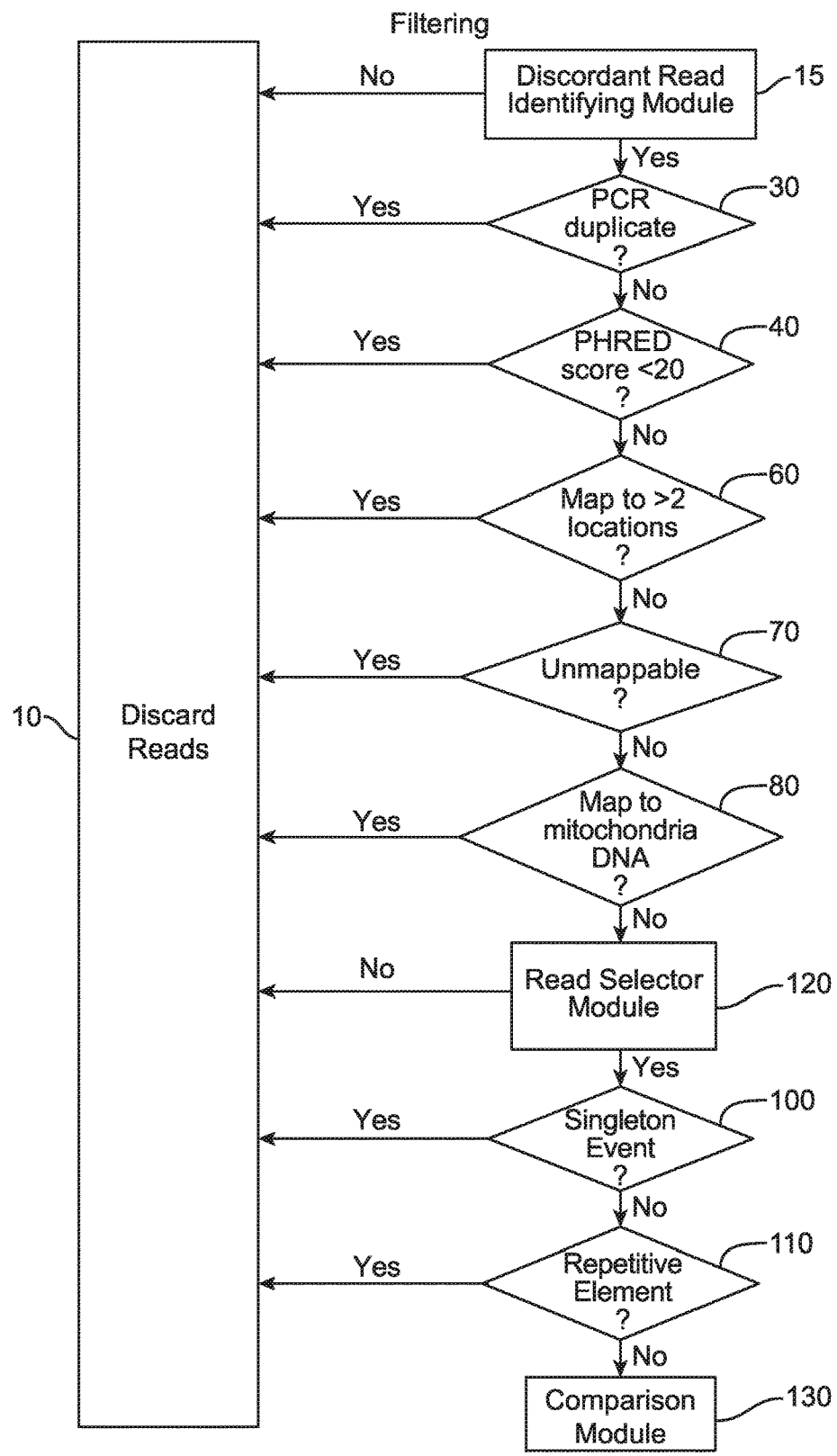
FIG. 7 shows an illustrative embodiment of filters.

A system or method for determining the presence or absence of one or more chromosome alterations for a sample may comprise one or more filtering steps and/or filters. A system or method for determining the presence or absence of one or more chromosome alterations for a sample may comprise 1 or more, 2 or more, 3 or more, 4, or more, 5 or more, 6 or more, 7 or more, 8 or more, 9 or more, 10 or more, 11 or more, 12 or more, 13 or more, 14 or more, 15 or more, 20 or more, 30 or more, 40 or more, or 50 or more filtering steps and/or filters. A filtering step can be performed before and/or after any method, or part, or step thereof as described herein. A system described herein may comprises a suitable filter before and/or after any suitable process or module described herein. For example, in an exemplary system as shown in FIG. 6, one or more filters and/or a filtering step can be introduced before or after 15, at 150, at 151, at 152, at 153 and/or after 140. One or more filtering processes and/or filters can occur in any suitable order or arrangement. For example, as shown in FIG. 7, a discordant read identifying module sends discordant reads to a PCR duplicate filter 30; filter 30 sends filtered reads to a sequence quality filter 40; filter 40 sends filtered reads to a mapping discontinuity filter 60; filter 60 sends filtered reads to a mapping filter 70; filter 70 sends filtered reads to a read selector module 120; module 120 sends selected reads to a singleton event filter 100; filter 100 sends filtered reads to a repetitive element filter 110; and filter 110 sends filtered reads to a comparison module 130. In some embodiments reads can be filtered one or more times by the same filter. Any suitable filter can be added to a method or system described herein. A filter and/or a filtering process is sometimes optional and may or may not be used with a method or system described herein. For example, filters 30, 40, 60, 70, 80, 90, 100 and/or 110 can be included or excluded from a method or system described herein.

Any suitable procedure can be utilized for processing data sets described herein. Non-limiting examples of procedures suitable for use for processing data sets include filtering, normalizing, weighting, mathematical processing of data, statistical processing of data, application of statistical algorithms, plotting data to identify patterns or trends for additional processing, the like and combinations of the foregoing. In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counter nulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta-analysis, simple linear regression, robust linear regression, the like or combinations of the foregoing.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set.

After data sets of sequence reads have been filtered, normalized, clustered, counted and/or weighted, the processed data sets can be analyzed and/or compared mathematically and/or statistically (e.g., by using statistical functions or statistical algorithm), in some embodiments. In certain embodiments, processed data sets can be further analyzed and/or compared by calculating Z-scores for one or more selected chromosomes or portions thereof. In some embodiments, processed data sets can be further analyzed and/or compared by calculating P-values. One embodiment of an equation for calculating a Z-score is presented in Equation A (Example 1).

Determining Fetal Nucleic Acid Content

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction". In some embodiments "fetal fraction" refers to the fraction of fetal nucleic acid in circulating cell-free nucleic acid in a sample (e.g., a blood sample, a serum sample, a plasma sample) obtained from a pregnant female. In some embodiments, a method in which a chromosome alteration is determined also can comprise determining fetal fraction. In some embodiments the presence or absence of a chromosome alteration is determined according to a fetal fraction (e.g., a fetal fraction determination for a sample). Determining fetal fraction can be performed by a suitable method, non-limiting examples of which include methods described below.

Fetal fraction can be determined, in some embodiments, using methods described herein for determining fragment length. Cell-free fetal nucleic acid fragments generally are shorter than maternally-derived nucleic acid fragments (see e.g., Chan et al. (2004) Clin. Chem. 50:88-92; Lo et al. (2010) Sci. Transl. Med. 2:61ra91). Thus, fetal fraction can be determined, in some embodiments, by counting fragments under a particular length threshold and comparing the counts to the amount of total nucleic acid in the sample. Methods for counting nucleic acid fragments of a particular length are described in further detail below.

In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. In certain embodiments, the amount of fetal nucleic acid from a maternal sample can be determined relative to the total amount of nucleic acid present, thereby providing the percentage of fetal nucleic acid in the sample. In certain embodiments, the copy number of fetal nucleic acid can be determined in a maternal sample. In certain embodiments, the amount of fetal nucleic acid can be determined in a sequence-specific (or portion-specific) manner and sometimes with sufficient sensitivity to allow for accurate chromosomal dosage analysis (for example, to detect the presence or absence of a fetal chromosome alteration).

A fetal quantifier assay (FQA) can be performed in conjunction with any of the methods described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In certain embodiments, the restriction efficiency can be determined and the efficiency rate is used to further determine the amount of fetal DNA.

In certain embodiments, a fetal quantifier assay (FQA) can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. In certain embodiments, the absolute copy number of fetal nucleic acid in a maternal sample can be determined, for example, using mass spectrometry and/or a system that uses a competitive PCR approach for absolute copy number measurements. See for example, Ding and Cantor (2003) PNAS USA 100:3059-3064, and U.S. Patent Application Publication No. 2004/0081993, both of which are hereby incorporated by reference.

In certain embodiments, fetal fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In certain embodiments, fetal alleles are identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting data, removing samples, making a call or not making a call).

A determination step (e.g., determining the presence or absence of a chromosome alteration) can be performed before, during, at any one point in a method described herein, or after certain methods described herein. For example, to achieve a determination (e.g., determination of a chromosome alteration in a fetus) with a given sensitivity or specificity, a fetal nucleic acid quantification method may be implemented prior to, during or after a chromosome alteration determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for fetal gender or the presence or absence of a chromosome alteration, for example. In certain embodiments, a determination of the presence or absence of a chromosome alteration is selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome alteration. In some embodiments, identifying the presence or absence of a chromosome alteration does not require the sequence differentiation of fetal versus maternal DNA. In certain embodiments this is because the summed contribution of both maternal and fetal sequences in a particular chromosome, chromosome portion or segment thereof is analyzed. In some embodiments, identifying the presence or absence of a chromosome alteration does not rely on a priori sequence information that would distinguish fetal DNA from maternal DNA.

Fetal Gender

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder.

In some embodiments, the prediction of a fetal gender or gender related disorder can be determined by a method, system, machine, apparatus or non-transitory computer readable storage medium described herein. Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production.

In some embodiments, a method in which fetal gender is determined can also comprise determining fetal fraction and/or presence or absence of a fetal chromosome alteration. Determining presence or absence of a fetal gender can be performed in a suitable manner, non-limiting examples of which include karyotype analysis, amniocentesis, circulating cell-free nucleic acid analysis, cell-free fetal DNA analysis, nucleotide sequence analysis, sequence read quantification, targeted approaches, amplification-based approaches, mass spectrometry-based approaches, differential methylation-based approaches, differential digestion-based approaches, polymorphism-based approaches, hybridization-based approaches (e.g., using probes), and the like.

Medical Disorders and Medical Conditions

Methods described herein can be applicable to any suitable medical disorder or medical condition. Non-limiting examples of medical disorders and medical conditions include cell proliferative disorders and conditions, wasting disorders and conditions, degenerative disorders and conditions, autoimmune disorders and conditions, pre-eclampsia, chemical or environmental toxicity, liver damage or disease, kidney damage or disease, vascular disease, high blood pressure, and myocardial infarction.

In some embodiments, a cell proliferative disorder or condition is a cancer of the liver, lung, spleen, pancreas, colon, skin, bladder, eye, brain, esophagus, head, neck, ovary, testes, prostate, the like or combination thereof. Non-limiting examples of cancers include hematopoietic neoplastic disorders, which are diseases involving hyperplastic/neoplastic cells of hematopoietic origin (e.g., arising from myeloid, lymphoid or erythroid lineages, or precursor cells thereof), and can arise from poorly differentiated acute leukemias (e.g., erythroblastic leukemia and acute megakaryoblastic leukemia). Certain myeloid disorders include, but are not limited to, acute promyeloid leukemia (APML), acute myelogenous leukemia (AML) and chronic myelogenous leukemia (CML). Certain lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Certain forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. A cell proliferative disorder sometimes is a non-endocrine tumor or endocrine tumor. Illustrative examples of non-endocrine tumors include, but are not limited to, adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor sometimes is an islet cell tumor.

In some embodiments, a wasting disorder or condition, or degenerative disorder or condition, is cirrhosis, amyotrophic lateral sclerosis (ALS), Alzheimer's disease, Parkinson's disease, multiple system atrophy, atherosclerosis, progressive supranuclear palsy, Tay-Sachs disease, diabetes, heart disease, keratoconus, inflammatory bowel disease (IBD), prostatitis, osteoarthritis, osteoporosis, rheumatoid arthritis, Huntington's disease, chronic traumatic encephalopathy, chronic obstructive pulmonary disease (COPD), tuberculosis, chronic diarrhea, acquired immune deficiency syndrome (AIDS), superior mesenteric artery syndrome, the like or combination thereof.

In some embodiments, an autoimmune disorder or condition is acute disseminated encephalomyelitis (ADEM), Addison's disease, alopecia areata, ankylosing spondylitis, antiphospholipid antibody syndrome (APS), autoimmune hemolytic anemia, autoimmune hepatitis, autoimmune inner ear disease, bullous pemphigoid, celiac disease, Chagas disease, chronic obstructive pulmonary disease, Crohns Disease (a type of idiopathic inflammatory bowel disease "IBD"), dermatomyositis, diabetes mellitus type 1, endometriosis, Goodpasture's syndrome, Graves' disease, Guillain-Barré syndrome (GBS), Hashimoto's disease, hidradenitis suppurativa, idiopathic thrombocytopenic purpura, interstitial cystitis, Lupus erythematosus, mixed connective tissue disease, morphea, multiple sclerosis (MS), myasthenia gravis, narcolepsy, euromyotonia, pemphigus vulgaris, pernicious anaemia, polymyositis, primary biliary cirrhosis, rheumatoid arthritis, schizophrenia, scleroderma, Sjögren's syndrome, temporal arteritis (also known as "giant cell arteritis"), ulcerative colitis (a type of idiopathic inflammatory bowel disease "IBD"), vasculitis, vitiligo, Wegener's granulomatosis, the like or combination thereof.

Systems, Machines, Storage Mediums and Interfaces

Certain processes and methods described herein often cannot be performed without a computer, microprocessor, software, module or other machine. Methods described herein typically are computer-implemented methods, and one or more portions of a method sometimes are performed by one or more processors (e.g., microprocessors), computers, or microprocessor controlled machines. Embodiments pertaining to methods described in this document generally are applicable to the same or related processes implemented by instructions in systems, machines and computer program products described herein. Embodiments pertaining to methods described in this document generally can be applicable to the same or related processes implemented by a non-transitory computer-readable storage medium with an executable program stored thereon, where the program instructs a microprocessor to perform the method, or a part thereof. The descriptive term "non-transitory" as used herein is expressly limiting and excludes transitory, propagating signals (e.g., transmission signals, electronic transmissions, waves (e.g., carrier waves)). The terms "non-transitory computer-readable media" and/or "non-transitory computer-readable medium" as used herein comprise all computer-readable mediums except for transitory, propagating signals. In some embodiments, processes and methods described herein are performed by automated methods. In some embodiments one or more steps and a method described herein is carried out by a microprocessor and/or computer, and/or carried out in conjunction with memory. In some embodiments, an automated method is embodied in software, modules, microprocessors, peripherals and/or a machine comprising the like, that (i) identify discordant reads, (ii) generate change in mappability, (iii) select subsets of reads according to change in mappability, (iv) determine candidate breakpoints, (v) filter reads, (vi) compare reads with substantially similar candidate breakpoints, (vii) determine the presence or absence of a chromosome alteration or (viii) perform a combination thereof.

Sequence reads, discordant reads, change in mappability of reads, select subsets of reads selected according to change in mappability, subsets of filtered reads, subsets of reads comprising similar candidate breakpoints, reads from a reference and/or reads from a test subject can be further analyzed and processed to determine the presence or absence of a chromosome alteration. Reads, selected reads, subsets of reads and quantitated reads are sometimes referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific], the like and combinations thereof). In certain embodiments, data or data sets can be organized into a matrix having two or more dimensions based on one or more features or variables. Data organized into matrices can be organized using any suitable features or variables. A non-limiting example of data in a matrix includes data that is organized by candidate breakpoints of a reference, candidate breakpoints of a test sample, Z-scores of a reference, Z-scores of a sample and breakpoint positions.

Machines, software and interfaces may be used to conduct methods described herein. Using machines, software and interfaces, a user may enter, request, query or determine options for using particular information, programs or processes (e.g., mapping sequence reads, generating sequence read subsequences, mapping sequence read subsequences, generating a relationship, generating change in mappability, selecting subsets of reads, comparing reads and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing apparatus or a sequencing apparatus, or a computing apparatus and a sequencing apparatus (i.e., sequencing machine and/or computing machine). Apparatus, as referred to herein, is sometimes a machine. A sequencing apparatus generally is configured to receive physical nucleic acid and generate signals corresponding to nucleotide bases of the nucleic acid. A sequencing apparatus is often "loaded" with a sample comprising nucleic acid and the nucleic acid of the sample loaded in the sequencing apparatus generally is subjected to a nucleic acid sequencing process. The term "loading a sequence apparatus" as used herein refers to contacting a portion of a sequencing apparatus (e.g., a flow cell) with a nucleic acid sample, which portion of the sequencing apparatus is configured to receive a sample for conducting a nucleic acid sequencing process. In some embodiments a sequencing apparatus is loaded with a variant of a sample nucleic acid. A variant sometimes is produced by a process that modifies the sample nucleic acid to a form suitable for sequencing the nucleic acid (e.g., by ligation (e.g., adding adaptors to ends of sample nucleic acid by ligation), amplification, restriction digest, the like or combinations thereof). A sequencing apparatus is often configured, in part, to perform a suitable DNA sequencing method that generates signals (e.g., electronic signals, detector signals, images, the like, or combinations thereof) corresponding to nucleotide bases of the loaded nucleic acid.

One or more signals corresponding to each base of a DNA sequence are often processed and/or transformed into base calls (e.g., a specific nucleotide base, e.g., guanine, cytosine, thymine, uracil, adenine, and the like) by a suitable process. A collection of base calls derived from a loaded nucleic acid often are processed and/or assembled into one or more sequence reads. In embodiments in which multiple sample nucleic acids are sequenced at one time (i.e., multiplexing), a suitable de-multiplexing process can be utilized to associated particular reads with the sample nucleic acid from which they originated. Sequence reads can be aligned by a suitable process to a reference genome and reads aligned to portions of the reference genome can be counted, as described herein.

A sequencing apparatus sometimes is associated with and/or comprises one or more computing apparatus in a system. The one or more computing apparatus sometimes are configured to perform one or more of the following processes: generating base calls from sequencing apparatus signals, assembling reads (e.g., generating reads), de-multiplexing reads, aligning reads to a reference genome, counting reads aligned to genomic portions in the reference genome, and the like. The one or more computing apparatus sometimes are configured to perform one or more of the following additional processes: normalize read counts (e.g., reduce or remove bias), generate one or more determinations (e.g., determine fetal fraction, fetal ploidy, fetal sex, fetal chromosome count, outcome, presence or absence of a genetic variation (e.g., presence or absence of a fetal chromosome aneuploidy (e.g., chromosome 13, 18 and/or 21 trisomy)), and the like.

In some embodiments, one computing apparatus is associated with a sequencing apparatus, and in certain embodiments, the one computing apparatus performs the majority or all of the following processes: generate base calls from sequencing apparatus signals, assemble reads, de-multiplex reads, align reads and count the reads aligned to genomic portions of a reference genome, normalize read counts and generate one or more outcomes (e.g., fetal fraction, presence or absence of a particular genetic variation). In the latter embodiments, in which one computing apparatus is associated with a sequencing apparatus, the computing apparatus often includes one or more processors (e.g., microprocessors) and memory having instructions that are carried out by the one or more processors to perform the processes. In some embodiments, the one computing apparatus can be a single or multi-core computing device local to the sequencing apparatus (e.g., located in the same location (e.g., the same address, the same building, same floor, same room or the like)). In some embodiments the one computing apparatus is integrated with the sequencing apparatus.

In some embodiments, multiple computing apparatus in a system are associated with a sequencing apparatus, and a subset of the total processes performed by the system may be allocated to or divided among particular computing apparatus in the system. Subsets of the total number of processes can be divided among two or more computing apparatus, or groups thereof, in any suitable combination. In certain embodiments, generating base calls from sequencing apparatus signals, assembling reads and de-multiplexing reads are performed by a first computing apparatus or group thereof, aligning and counting reads mapped to portions of a reference genome are performed by a second computing apparatus or group thereof, and normalizing read counts and providing one or more outcomes are performed by a third computing apparatus or group thereof. In systems comprising two or more computing apparatus or groups thereof, each particular computing apparatus may include memory, one or more processors or a combination thereof. A multi-computing apparatus system sometimes includes one or more suitable servers local to a sequencing apparatus, and sometimes includes one or more suitable servers not local to the sequencing apparatus (e.g., web servers, on-line servers, application servers, remote file servers, cloud servers (e.g., cloud environment, cloud computing)).

Apparatus in different system configurations can generate different types of output data. For example, a sequencing apparatus can output base signals and the base signal output data can be transferred to a computing apparatus that converts the base signal data to base calls. In some embodiments, the base calls are output data from one computing apparatus and are transferred to another computing apparatus for generating sequence reads. In certain embodiments, base calls are not output data from a particular apparatus, and instead, are utilized in the same apparatus that received sequencing apparatus base signals to generate sequence reads. In some embodiments, one apparatus receives sequencing apparatus base signals, generates base calls, sequence reads and de-multiplexes sequence reads, and outputs de-multiplexed sequence reads for a sample that can be transferred to another apparatus or group thereof that aligns the sequence reads to a reference genome. In some embodiments, one apparatus or group thereof can output aligned sequence reads mapped to portions of a reference genome (e.g., SAM or BAM files), and such output data can be transferred to a second computing apparatus or group thereof that normalizes the sequence reads (e.g., normalizes the counts of the sequence reads) and generates an outcome (e.g., fetal fraction and/or presence or absence of a fetal trisomy). Output data from one apparatus can be transferred to a second apparatus in any suitable manner. For example, output data from one apparatus sometimes is placed on a physical storage device and the storage device is transported and connected to a second apparatus to which the output data is transferred. Output data sometimes is stored by one apparatus in a database, and a second apparatus accesses the output data from the same database.

In some embodiments a user interacts with an apparatus (e.g., a computing apparatus, a sequencing apparatus). A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses (multiple apparatuses, also referred to herein in plural as apparatus), computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to data (e.g., sequence read subsequences), a manipulation of data, research and experiments that are performed using a computer. In silico processes include, but are not limited to, mapping sequence reads, generating sequence read subsequences, mapping reads and read subsequences, and processing mapped sequence reads according to processes described herein.

A system may include software useful for performing a process described herein, and software can include one or more modules for performing such processes (e.g., sequence module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein.

A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module by one or more microprocessors. Instructions of a module can be implemented in a computing environment by use of a suitable programming language, suitable software, and/or code written in a suitable language (e.g., a computer programming language known in the art) and/or operating system, non-limiting examples of which include UNIX, Linux, oracle, windows, Ubuntu, ActionScript, C, C++, C#, Haskell, Java, JavaScript, Objective-C, Perl, Python, Ruby, Smalltalk, SQL, Visual Basic, COBOL, Fortran, UML, HTML (e.g., with PHP), PGP, G, R, S, the like or combinations thereof. In some embodiments a module described herein comprises code (e.g., script) written in S or R that utilizes a suitable package (e.g., an S package, an R package). R, R source code, R programs, R packages and R documentation are available for download from a CRAN or CRAN mirror site (The Comprehensive R Archive Network (CRAN)[online], [retrieved on 2013 Apr. 24], retrieved from the internet at world wide web uniform resource locator: cran.us.r-project.org). CRAN is a network of ftp and web servers around the world that store identical, up-to-date, versions of code and documentation for R.

A module can transform data and/or information. One or more modules can be utilized in a method described herein, non-limiting examples of which include a sequence module, a mapping module, a discordant read identifying module, a fragmentation module, a read selector module, a mapping characterization module, a breakpoint module, a comparison module, a filter module, a plotting module, an outcome module, the like or combination thereof. For example, as exemplified in one embodiment shown in FIG. 6, a discordant read identifying module 15 sends discordant reads to a mapping characterization module 50 configured to receive discordant reads from a discordant read identifying module 15. A mapping characterization module 50 can send mapping characterizations to a read selector module 120 configured to receive mapping characterizations from a mapping characterization module 50. A read selector module 120 can send a selected subset of reads (e.g., discordant read pairs) to a comparison module 130 configured to receive a selected subset of reads from a read selector module 120. A comparison module 130 can generate a comparison (e.g., comparing (i) the number of discordant read mates from the sample associated with a candidate breakpoint and optionally one or more substantially similar breakpoints, to (ii) a number of discordant read mates from a reference associated with the candidate breakpoint and optionally the one or more substantially similar breakpoints) and send the comparison to an outcome module 140 configured to receive a comparison. An outcome module 140 can then determine the presence or absence of a translocation in a test subject and provide an outcome to an end user or send the outcome to another module (e.g., a plotting module). Modules are sometimes controlled by a microprocessor. In certain embodiments a module or a machine comprising one or more modules, gather, assemble, receive, obtain, access, recover provide and/or transfer data and/or information to or from another module, machine, component, peripheral or operator of a machine. In some embodiments, data and/or information (e.g., sequencing reads) are provided to a module by a machine comprising one or more of the following: one or more flow cells, a camera, a detector (e.g., a photo detector, a photo cell, an electrical detector (e.g., an amplitude modulation detector, a frequency and phase modulation detector, a phase-locked loop detector), a counter, a sensor (e.g., a sensor of pressure, temperature, volume, flow, weight), a fluid handling device, a data input device (e.g., a keyboard, mouse, scanner, voice recognition software and a microphone, stylus, or the like), a printer, a display (e.g., an LED, LCT or CRT), the like or combinations thereof. For example, sometimes an operator of a machine or apparatus provides a constant, a threshold value, a formula or a predetermined value to a module. A module is often configured to transfer data and/or information to or from a microprocessor and/or memory. A module is often configured to transfer data and/or information to or receive data and/or information from another suitable module or machine. A module can manipulate and/or transform data and/or information. Data and/or information derived from or transformed by a module can be transferred to another suitable machine and/or module. A machine comprising a module can comprise at least one microprocessor. A machine comprising a module can include a microprocessor (e.g., one or more microprocessors) which microprocessor can perform and/or implement one or more instructions (e.g., processes, routines and/or subroutines) of a module. In some embodiments, a module operates with one or more external microprocessors (e.g., an internal or external network, server, storage device and/or storage network (e.g., a cloud)).

Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an machine, peripheral, component or another module. A module can perform one or more of the following non-limiting functions: mapping sequence reads, identifying discordant read pairs, generating sequence read subsequences, characterizing the mappability of a plurality of sequence read subsequences, generating change in mappability, generating mappability thresholds, filtering, selecting a subset of the discordant read mates according to change in mappability and/or mappability thresholds, identifying candidate breakpoints, identifying breakpoints, plotting, generating a comparison (e.g., comparing (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints) and/or determining an outcome (e.g., a determination of the presence or absence of a chromosome alteration), for example. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a non-transitory computer-readable medium, and sometimes is tangibly embodied on a non-transitory computer-readable medium. A module sometimes is stored on a non-transitory computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. Sequence reads mapped to a reference genome sometimes are accessed by a microprocessor that executes instructions configured to carry out a method described herein. Sequence reads that are accessed by a microprocessor can be within memory of a system, and the reads can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module. In certain embodiments a machine comprises one or more modules. A machine comprising a module often can receive and transfer one or more of data and/or information to and from other modules. In certain embodiments, a machine comprises peripherals and/or components. In certain embodiments a machine can comprise one or more peripherals or components that can transfer data and/or information to and from other modules, peripherals and/or components. In certain embodiments a machine interacts with a peripheral and/or component that provides data and/or information. In certain embodiments peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), fluid handling components, network interface controllers, read-only memory (ROM), random-access memory (RAM), wireless transfer devices (Bluetooth devices, WiFi devices, and the like), the world wide web (www), the internet, a computer and/or another module.

Software often is provided on a program product containing program instructions recorded on a non-transitory computer readable medium, including, but not limited to, magnetic media (e.g., floppy disks, hard disks, ROMs and magnetic tape), optical media (e.g., CD-ROMs, DVDs, and the like), magneto-optical discs, flash drives, RAM, the like, and other such media on which program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a non-transitory computer usable medium having a non-transitory computer readable program code embodied therein, the computer readable program code adapted to be executed to implement a method comprising: (a) identifying discordant read pairs from paired-end sequence reads, where the paired-end sequence reads are reads of circulating, cell-free nucleic acid from a test subject sample, thereby identifying discordant read mates, (b) characterizing the mappability of a plurality of sequence read subsequences of each discordant read mate aligned to a reference genome, each of which sequence read subsequences of each discordant read mate is of a different length, thereby providing change in mappability for the discordant read mates, (c) selecting a subset of the discordant read mates according to the change in mappability in (b), where the subset comprises reads comprising a candidate breakpoint, (d) comparing (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison, and (e) determining the presence or absence of one or more chromosome alterations for the sample according to the comparison in (d).

Software can be used to perform one or more, or all steps of the processes or methods described herein, including but not limited to; identifying discordant reads (e.g., 15), generating sequence read subsequences, characterizing the mappability of sequence read subsequences, generating change in mappability (e.g., 50), identifying candidate breakpoints and/or breakpoints, selecting subsets of read mates (e.g. 120), comparing subsets of reads comprising similar breakpoints (e.g., 130), filtering (e.g., 20, 30, 40, 50, 70, 80, 90, 100, and 110), data processing, determining the presence or absence of a chromosome alteration (e.g., 140), generating an outcome, and/or providing one or more recommendations based on generated outcomes, as described herein. The term "software" as used herein refers to a non-transitory computer-readable storage medium with an executable program stored thereon, where the program instructs a microprocessor to perform a function (e.g., a method). In some embodiments a non-transitory computer-readable storage medium with an executable program stored thereon, instructs a microprocessor to identify discordant read pairs from paired-end sequence reads, where the paired-end sequence reads are reads of circulating, cell-free nucleic acid from a test subject sample, thereby identifying discordant read mates. In certain embodiments a non-transitory computer-readable storage medium with an executable program stored thereon, instructs a microprocessor to characterize the mappability of a plurality of sequence read subsequences of each discordant read mate aligned to a reference genome, each of which sequence read subsequences of each discordant read mate is of a different length, thereby providing change in mappability and candidate breakpoints for the discordant read mates. In some embodiments a non-transitory computer-readable storage medium with an executable program stored thereon, instructs a microprocessor to select a subset of the discordant read mates according to a change in mappability and/or according to a mappability threshold. In some embodiments a non-transitory computer-readable storage medium with an executable program stored thereon, instructs a microprocessor to compare (i) the number of discordant read mates from a sample associated with a candidate breakpoint and optionally one or more substantially similar breakpoints, to (ii) the number of discordant read mates from a reference associated with the candidate breakpoint and optionally the one or more substantially similar breakpoints. In certain embodiments a non-transitory computer-readable storage medium with an executable program stored thereon, instructs a microprocessor to determine the presence or absence of one or more chromosome alterations for a sample. In some embodiments a non-transitory computer-readable storage medium with an executable program stored thereon, instructs a microprocessor to (a) identify discordant read pairs from paired-end sequence reads, where the paired-end sequence reads are reads of circulating, cell-free nucleic acid from a test subject sample, thereby identifying discordant read mates, (b) characterize the mappability of a plurality of sequence read subsequences of each discordant read mate aligned to a reference genome, each of which sequence read subsequences of each discordant read mate is of a different length, thereby providing change in mappability for the discordant read mates, (c) select a subset of the discordant read mates according to the change in mappability in (b), where the subset comprises reads comprising a candidate breakpoint, (d) compare (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison, and (e) determine the presence or absence of one or more chromosome alterations for the sample according to the comparison in (d).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational geometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, R, S, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a non-transitory computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining the presence or absence of a chromosome alteration.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

One entity can generate sequence reads, map the sequence reads, identify discordant read pairs, and utilize discordant read pairs in a method, system, machine, apparatus or computer program product described herein, in some embodiments. Sequence reads mapped to a reference genome sometimes are transferred by one entity to a second entity for use by the second entity in a method, system, machine, apparatus or computer program product described herein, in certain embodiments.

In some embodiments, one entity generates sequence reads and a second entity maps those sequence reads to a reference genome in some embodiments. The second entity sometimes identifies discordant reads and utilizes the discordant reads in a method, system, machine or computer program product described herein. In certain embodiments the second entity transfers the mapped reads to a third entity, and the third entity identifies discordant reads and utilizes the discordant reads in a method, system, machine or computer program product described herein. In certain embodiments the second entity identifies discordant reads and transfers the identifies discordant reads to a third entity, and the third entity utilizes the identifies discordant reads in a method, system, machine or computer program product described herein. In embodiments involving a third entity, the third entity sometimes is the same as the first entity. That is, the first entity sometimes transfers sequence reads to a second entity, which second entity can map sequence reads to a reference genome and/or identify discordant reads, and the second entity can transfer the mapped and/or discordant reads to a third entity. A third entity sometimes can utilize the mapped and/or discordant reads in a method, system, machine or computer program product described herein, where the third entity sometimes is the same as the first entity, and sometimes the third entity is different from the first or second entity.

In some embodiments, one entity obtains blood from a pregnant female, optionally isolates nucleic acid from the blood (e.g., from the plasma or serum), and transfers the blood or nucleic acid to a second entity that generates sequence reads from the nucleic acid.

Figure 8:
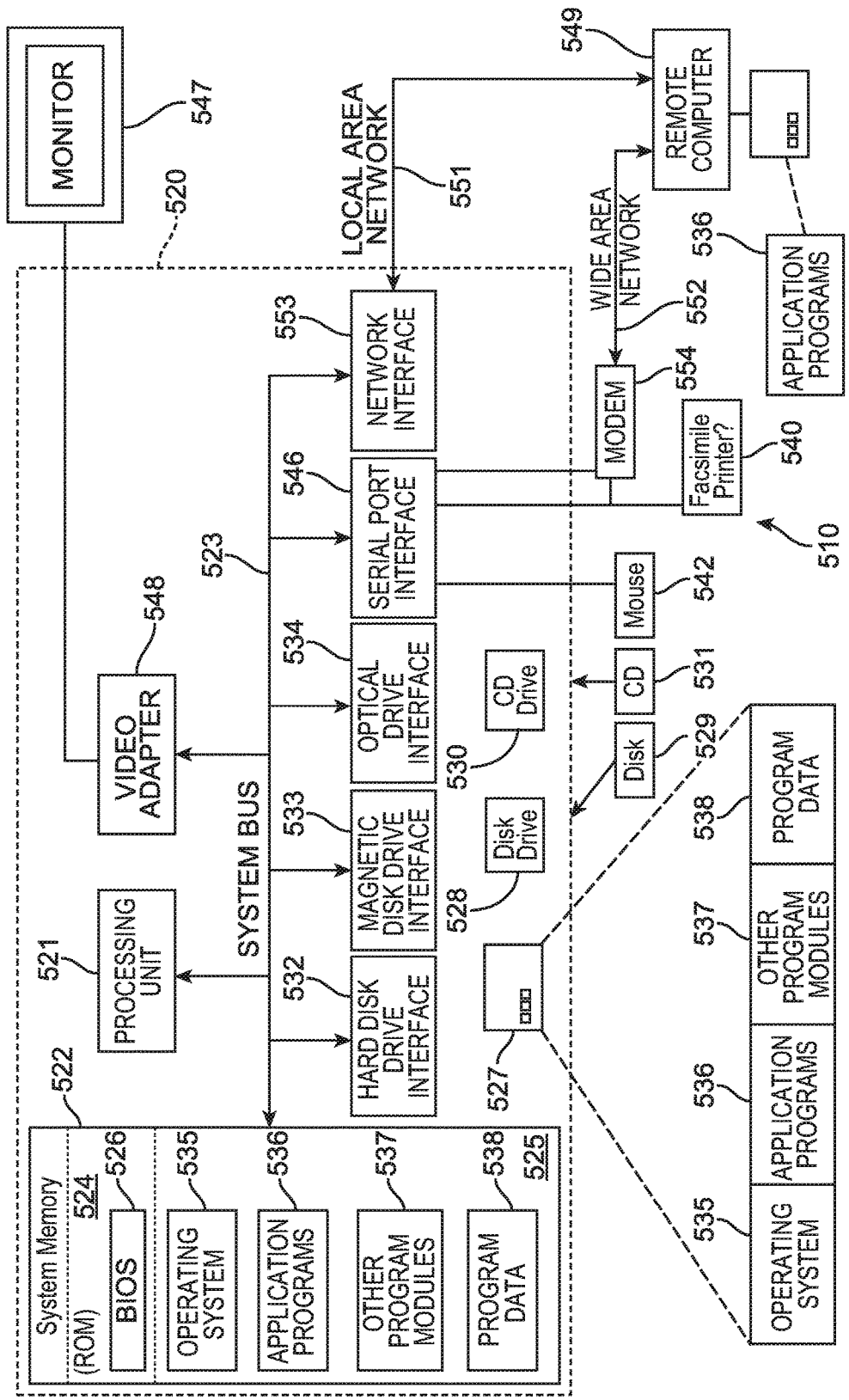
FIG. 8 shows an illustrative embodiment of a system in which certain embodiments of the technology may be implemented.

FIG. 8 illustrates a non-limiting example of a computing environment 510 in which various systems, methods, algorithms, and data structures described herein may be implemented. The computing environment 510 is only one example of a suitable computing environment and is not intended to suggest any limitation as to the scope of use or functionality of the systems, methods, and data structures described herein. Neither should computing environment 510 be interpreted as having any dependency or requirement relating to any one or combination of components illustrated in computing environment 510. A subset of systems, methods, and data structures shown in FIG. 8 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 510 of FIG. 8 includes a general purpose computing device in the form of a computer 520, including a processing unit 521, a system memory 522, and a system bus 523 that operatively couples various system components including the system memory 522 to the processing unit 521. There may be only one or there may be more than one processing unit 521, such that the microprocessor of computer 520 includes a single central-processing unit (CPU), or a plurality of processing units, commonly referred to as a parallel processing environment. The computer 520 may be a conventional computer, a distributed computer, or any other type of computer.

The system bus 523 may be any of several types of bus structures including a memory bus or memory controller, a peripheral bus, and a local bus using any of a variety of bus architectures. The system memory may also be referred to as simply the memory, and includes read only memory (ROM) 524 and random access memory (RAM). A basic input/output system (BIOS) 526, containing the basic routines that help to transfer information between elements within the computer 520, such as during start-up, is stored in ROM 524. The computer 520 may further include a hard disk drive interface 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 529, optical disk 531, ROM 524, or RAM, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections may be achieved by a communication device coupled to or a part of the computer 520, or in other manners. The remote computer 549 may be another computer, a server, a router, a network PC, a client, a peer device or other common network node, and typically includes many or all of the elements described above relative to the computer 520, although only a memory storage device 550 has been illustrated in FIG. 8. The logical connections depicted in FIG. 8 include a local-area network (LAN) 551 and a wide-area network (WAN) 552. Such networking environments are commonplace in office networks, enterprise-wide computer networks, intranets and the Internet, which all are types of networks.

When used in a LAN-networking environment, the computer 520 is connected to the local network 551 through a network interface or adapter 553, which is one type of communications device. When used in a WAN-networking environment, the computer 520 often includes a modem 554, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are non-limiting examples and other communications devices for establishing a communications link between computers may be used.

Certain System, Machine and Computer Program Product Embodiments

Provided herein, in certain aspects, is a system comprising memory and one or more microprocessors, which memory comprises instructions and which one or more microprocessors are configured to perform, according to the instructions, a process for determining the presence or absence of one or more chromosome alterations in sample nucleic acid, which process comprises (a) characterizing mappability of a plurality of sequence read subsequences for sequence reads, where there are multiple sequence read subsequences for each sequence read, the sequence read subsequences for each sequence read are of different lengths, and the sequence reads are of the sample nucleic acid, (b) identifying a subset of sequence reads for which there is a change in mappability of one or more subsequences, (c) comparing (i) the number of each of the sequence reads in the subset identified in (b) from the sample, to (ii) the number of each of the sequence reads in the subset identified in (b) from a reference, thereby generating a comparison; and (d) determining the presence or absence of one or more chromosome alterations for the sample according to the comparison in (c).

Also provided herein, in certain aspects, is a method comprising memory and one or more microprocessors, which memory comprises instructions and which one or more microprocessors are configured to perform, according to the instructions, a process for determining the presence or absence of one or more chromosome alterations in sample nucleic acid, which process comprises (a) characterizing mappability of a plurality of sequence read subsequences for sequence reads, where there are multiple sequence read subsequences for each sequence read, the sequence read subsequences for each sequence read are of different lengths, and the sequence reads are of the sample nucleic acid, (b) identifying a subset of sequence reads for which there is a change in mappability of one or more subsequences, (c) comparing (i) the number of each of the sequence reads in the subset identified in (b) from the sample, to (ii) the number of each of the sequence reads in the subset identified in (b) from a reference, thereby generating a comparison; and (d) determining the presence or absence of one or more chromosome alterations for the sample according to the comparison in (c).

Also provided herein, in certain aspects, is a non-transitory computer-readable storage medium with an executable program stored thereon, which program is configured to instruct a microprocessor to (a) characterize mappability of a plurality of sequence read subsequences for sequence reads, where there are multiple sequence read subsequences for each sequence read, the sequence read subsequences for each sequence read are of different lengths, and the sequence reads are of the sample nucleic acid, (b) identify a subset of sequence reads for which there is a change in mappability of one or more subsequences, (c) compare (i) the number of each of the sequence reads in the subset identified in (b) from the sample, to (ii) the number of each of the sequence reads in the subset identified in (b) from a reference, thereby generating a comparison and (d) determine the presence or absence of one or more chromosome alterations for the sample according to the comparison in (c).

In certain aspects provided is a computer implemented method for determining the presence or absence of a chromosome alteration, comprising (a) identifying discordant read pairs from paired-end sequence reads, where the paired-end sequence reads are reads of circulating, cell-free nucleic acid from a test subject sample, thereby identifying discordant read mates, (b) characterizing the mappability of a plurality of sequence read subsequences of each discordant read mate aligned to a reference genome, each of which sequence read subsequences of each discordant read mate is of a different length, thereby providing change in mappability for the discordant read mates, (c) selecting a subset of the discordant read mates according to the change in mappability in (b), where the subset comprises reads comprising a candidate breakpoint; (d) comparing (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison and (e) determining the presence or absence of one or more chromosome alterations for the sample according to the comparison in (d).

Provided also in certain aspects is a system comprising one or more microprocessors and memory, which memory comprises instructions executable by the one or more microprocessors and which memory comprises nucleotide sequence reads mapped to a reference genome, which sequence reads are reads of circulating, cell-free nucleic acid from a test subject sample and which instructions direct one or more microprocessors to (a) identify discordant read pairs from paired-end sequence reads, where the paired-end sequence reads are reads of circulating, cell-free nucleic acid from a test subject sample, thereby identifying discordant read mates, (b) characterize the mappability of a plurality of sequence read subsequences of each discordant read mate aligned to a reference genome, each of which sequence read subsequences of each discordant read mate is of a different length, thereby providing change in mappability for the discordant read mates, (c) select a subset of the discordant read mates according to the change in mappability in (b), where the subset comprises reads comprising a candidate breakpoint, (d) compare (i) the number of discordant read mates from the sample associated with the candidate breakpoints and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison and (e) determine the presence or absence of one or more chromosome alterations for the sample according to the comparison in (d).

A system comprising memory and one or more microprocessors, which memory comprises instructions and which one or more microprocessors are configured to perform, according to the instructions, a process for determining the presence or absence of one or more chromosome alterations in sample nucleic acid, which process comprises (a) identifying discordant read pairs from paired-end sequence reads, where the paired-end sequence reads are reads of circulating, cell-free nucleic acid from a test subject sample, thereby identifying discordant read mates, (b) characterizing the mappability of a plurality of sequence read subsequences of each discordant read mate aligned to a reference genome, each of which sequence read subsequences of each discordant read mate is of a different length, thereby providing change in mappability for the discordant read mates, (c) selecting a subset of the discordant read mates according to the change in mappability in (b), where the subset comprises reads comprising a candidate breakpoint, (d) comparing (i) the number of discordant read mates from the sample associated with the candidate breakpoints and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison and (e) determining the presence or absence of one or more chromosome alterations for the sample according to the comparison in (d). In some embodiments a system comprises one or more machines. In some embodiments a system comprises a sequencing machine configured to generate the sequence reads. In some embodiments a system as described herein is embodied in one machine.

Also provided in certain aspects is a machine comprising one or more microprocessors and memory, which memory comprises instructions executable by the one or more microprocessors and which memory comprises nucleotide sequence reads mapped to a reference genome, which sequence reads are reads of circulating, cell-free nucleic acid from a test subject sample and which instructions direct one or more microprocessors to (a) identify discordant read pairs from paired-end sequence reads, where the paired-end sequence reads are reads of circulating, cell-free nucleic acid from a test subject sample, thereby identifying discordant read mates, (b) characterize the mappability of a plurality of sequence read subsequences of each discordant read mate aligned to a reference genome, each of which sequence read subsequences of each discordant read mate is of a different length, thereby providing change in mappability for the discordant read mates, (c) select a subset of the discordant read mates according to the change in mappability in (b), where the subset comprises reads comprising a candidate breakpoint, (d) compare (i) the number of discordant read mates from the sample associated with the candidate breakpoints and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison and (e) determine the presence or absence of one or more chromosome alterations for the sample according to the comparison in (d).

Provided also in certain embodiments is an apparatus comprising one or more processors and memory, which memory comprises instructions executable by the one or more processors and which memory comprises nucleic acid sequence reads mapped to a reference genome; and which instructions executable by the one or more processors are configured to (a) identify discordant read pairs from paired-end sequence reads, where the paired-end sequence reads are reads of circulating, cell-free nucleic acid from a test subject sample, thereby identifying discordant read mates, (b) characterize the mappability of a plurality of sequence read subsequences of each discordant read mate aligned to a reference genome, each of which sequence read subsequences of each discordant read mate is of a different length, thereby providing change in mappability for the discordant read mates, (c) select a subset of the discordant read mates according to the change in mappability in (b), where the subset comprises reads comprising a candidate breakpoint (d) compare (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison and (e) determine the presence or absence of one or more chromosome alterations for the sample according to the comparison in (d).

Also provided also in certain embodiments is an apparatus comprising one or more processors and memory, which memory comprises (i) instructions executable by the one or more processors and (ii) discordant read pairs identified from paired-end sequence reads, where the paired-end sequence reads are reads of circulating, cell-free nucleic acid from a test subject sample, and which instructions executable by the one or more processors are configured to (a) characterize the mappability of a plurality of sequence read subsequences of each discordant read mate aligned to a reference genome, each of which sequence read subsequences of each discordant read mate is of a different length, thereby providing change in mappability and candidate breakpoints for the discordant read mates, (b) select a subset of the discordant read mates according to the change in mappability in (a), (c) compare (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (b), thereby generating a comparison and (d) determine the presence or absence of one or more chromosome alterations for the sample according to the comparison in (d).

Provided also in certain embodiments is a computer program product tangibly embodied on a non-transitory computer-readable medium, comprising instructions that when executed by one or more microprocessors are configured to (a) identify discordant read pairs from paired-end sequence reads, where the paired-end sequence reads are reads of circulating, cell-free nucleic acid from a test subject sample, thereby identifying discordant read mates, (b) characterize the mappability of a plurality of sequence read subsequences of each discordant read mate aligned to a reference genome, each of which sequence read subsequences of each discordant read mate is of a different length, thereby providing change in mappability for the discordant read mates, (c) select a subset of the discordant read mates according to the change in mappability in (b), where the subset comprises reads comprising a candidate breakpoint, (d) compare (i) the number of discordant read mates from the sample associated with the candidate breakpoints and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison and (e) determine the presence or absence of one or more chromosome alterations for the sample according to the comparison in (d).

Also provided herein is a non-transitory computer-readable storage medium with an executable program stored thereon, where the program instructs a microprocessor to (a) identify discordant read pairs from paired-end sequence reads, where the paired-end sequence reads are reads of circulating, cell-free nucleic acid from a test subject sample, thereby identifying discordant read mates, (b) characterize the mappability of a plurality of sequence read subsequences of each discordant read mate aligned to a reference genome, each of which sequence read subsequences of each discordant read mate is of a different length, thereby providing change in mappability for the discordant read mates, (c) select a subset of the discordant read mates according to the change in mappability in (b), where the subset comprises reads comprising a candidate breakpoint, (d) compare (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison and (e) determine the presence or absence of one or more chromosome alterations for the sample according to the comparison in (d).

Transformations

Determining the presence or absence of a chromosome alteration as described herein can be viewed as a transformation of nucleic acid sequence reads into a representation of a subject's cellular nucleic acid (e.g., cellular nucleic acid of a fetus), in certain embodiments. A representation of a subject's cellular nucleic acid often reflects a chromosome alteration for a particular chromosome or portion thereof, and the representation thereby often is a property of the subject's nucleic acid. Converting a multitude of relatively small sequence reads to a representation of one or more relatively large chromosomes, for example, can be viewed as a transformation. As an illustration, in a process for generating a representation of chromosome 21, which is about 47 million bases in length, using reads of approximately 36 base pairs in length, many thousands of reads that are at least 100,000 times smaller than the chromosome are transformed into a representation of the significantly larger chromosome. Generating such a representation of a chromosome typically involves several manipulations of reads (e.g., mapping, filtering, analyzing and/or normalizing) to arrive at a representation of the relatively large chromosome, as described herein. Multiple manipulations often are utilized, which can require the use of one or more computers, often multiple computers coordinated in parallel.

When providing a representation of a chromosome for a fetal chromosome using a sample from a pregnant female, such a transformation further is apparent given that the majority of reads often are from maternal nucleic acid and a minority of reads often are from fetal nucleic acid. Reads of maternal nucleic acid often dominate reads of fetal nucleic acid, and the majority of maternal nucleic acid reads often masks a representation of a fetal chromosome. A typically large background of maternal reads can obscure differences between fetal and maternal chromosome nucleic acid and obtaining a representation of a fetal chromosome against such a background involves a process that deconvolutes the contribution of maternal reads, as described herein.

In some embodiments, determining the presence or absence of a chromosome alteration results from a transformation of sequence reads from a subject (e.g., a pregnant female), into a representation of an existing structure (e.g., a genome, a chromosome or segment thereof) present in a subject (e.g., a mother and/or fetus). In some embodiments, determining the presence or absence of a chromosome alteration comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus). In some embodiments, determining the presence or absence of a chromosome alteration comprises a transformation of sequence reads from a first subject (e.g., a female subject, a pregnant female), into a representation of structures (e.g., a genome, a chromosome or segment thereof) present in a second subject (e.g., a fetus).

A transformative method herein sometimes comprises determining the presence or absence of a translocation in a fetus from nucleic acid reads in a sample obtained from a pregnant female subject carrying the fetus. In some embodiments, a transformative method herein may comprise preparing (e.g., determining, visualizing, displaying, providing) a representation of a chromosome (e.g., chromosome translocation) for a fetus from nucleic acid reads in a sample obtained from a pregnant female subject carrying the fetus.

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, discordant read pairs, change in mappability, candidate breakpoint determinations, counts of reads (e.g., counts of reads comprising substantially similar candidate breakpoints), breakpoint determinations, identification of a chromosomal alteration, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

Example 1: Method Development (Simulations)

Structural rearrangements were simulated in silico by connecting two independent regions from the human reference genome (hg19). The sequences were designed to be unique on both ends, unique on one end and derived from repetitive sequences on the other, or having both ends originating from repetitive elements. Since ccf DNA has a reported average length of about 166 bp, the fragment length of the simulated reads was restricted to a range of 140-180 bp. In addition, breakpoint positions were systematically generated along the fragment length. In the absence of sequencing error, 2×100 paired end sequence reads were generated, where each mate pair overlapped by up to 60 bases. MAPQ score characteristics were determined by Bowtie for each mate pair as a function of the breakpoint location and read length for simulated fragments of 140 bp (FIG. 2A-2D). When the breakpoint was near the edge of a fragment (FIG. 2A), shorter read lengths demonstrated lower mapping quality, whereas larger read lengths had higher mapping quality for mate 1. Mate 2 was unaffected by the breakpoint. As the breakpoint traverses along the fragment length, a reciprocal behavior was observed where both mate pairs exhibited a decrease in mapping quality as the read lengths are increased (FIG. 2).

Figure 3:
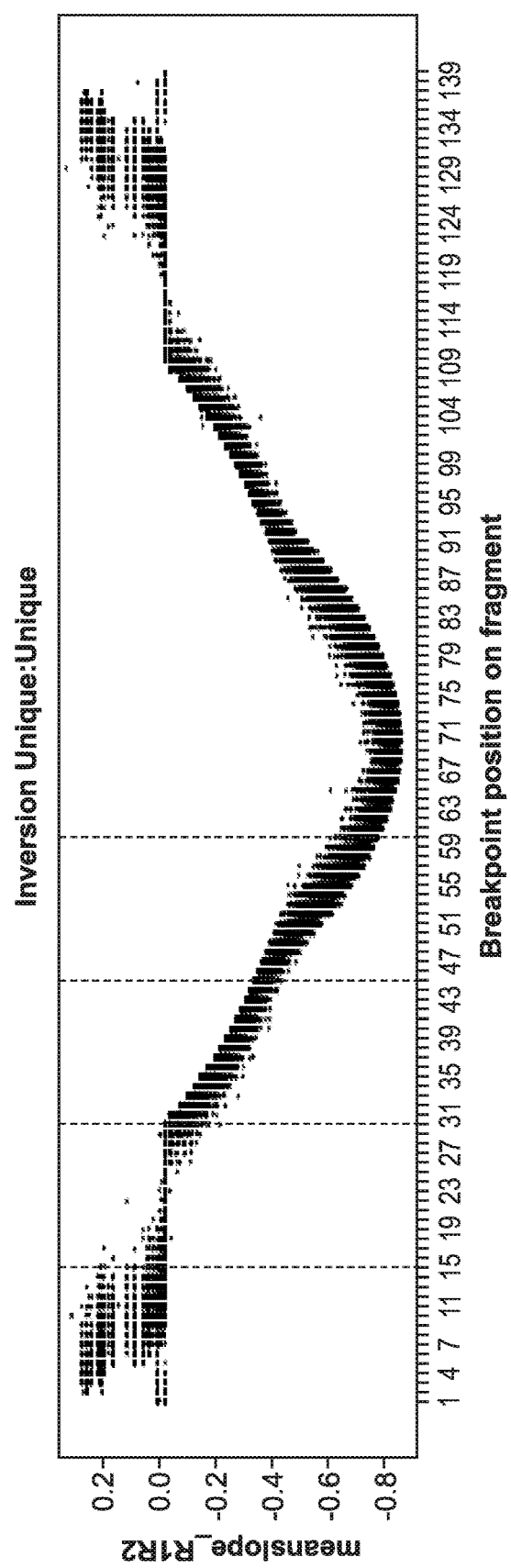
FIG. 3 shows simulated translocations with both regions comprising highly unique sequences. For each simulated translocation event, the mean slope of the mapping quality score (y-axis) is plotted at all simulated breakpoint positions (x-axis).
Figure 4:
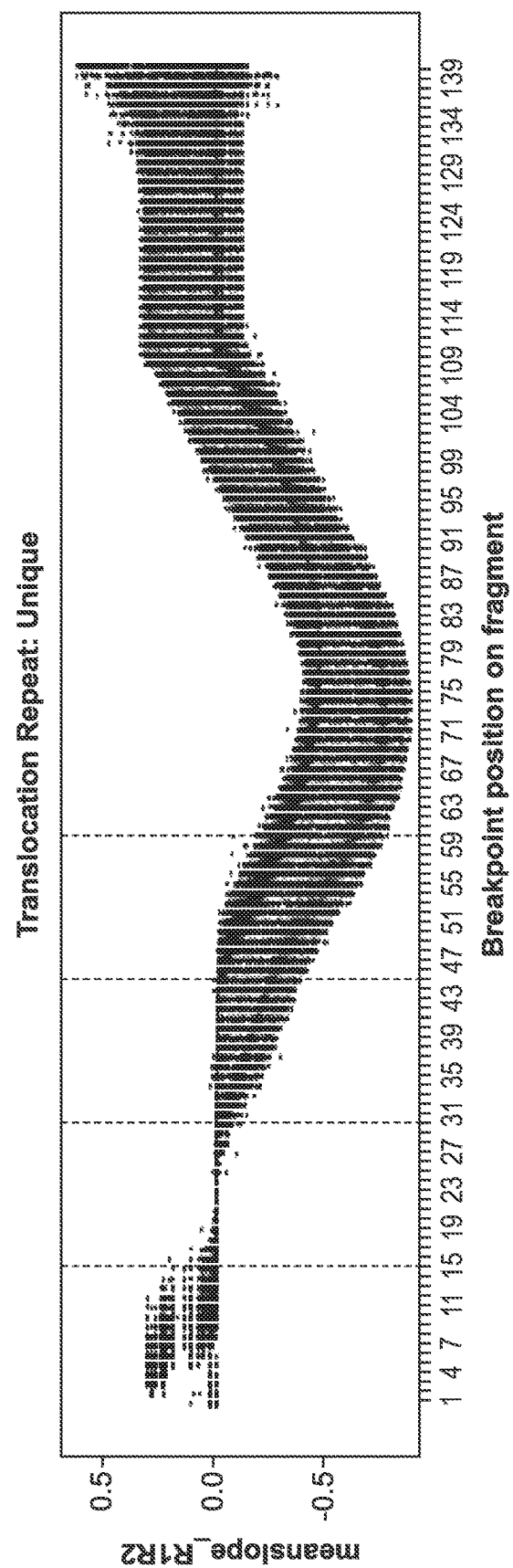
FIG. 4 shows simulated translocations with the left region comprising highly unique sequences and the right region comprising repetitive elements. For each simulated translocation event, the mean slope of the mapping quality score (y-axis) is plotted at all simulated breakpoint positions (x-axis).

Mapping characteristics were consistent regardless of simulated fragment length and provided a signature of discordant paired end reads containing fragment specific rearrangements relative to the human reference genome. Two metrics were used to describe the mapping/alignment characteristics for a given paired end read. The first was the average slope of the linear model of read length and MAPQ scores for each mate. The second was the average of the maximum difference in alignment scores for each mate. The overall distributions of the mean slope metric at all breakpoints for simulated fragment lengths of 140 bases was determined (FIG. 3). Simulated fragments containing centrally located breakpoints exhibited the most drastic changes in slope and differences in alignment scores. When repetitive elements were incorporated into the simulations, an increase in the variance of the metrics was observed (FIG. 4). However, despite low sequence complexity, the length of the read retained sufficient uniqueness to allow for correct alignment, which supports the feasibility of detecting structural rearrangements in repetitive regions of the genome.

Sample Acquisition and Blood Processing

Clinical samples were collected under Investigational Review Board (IRB) approved clinical protocols (Compass IRB 00508 or Western IRB 20080757). Subjects provided written informed consent prior to undergoing any study related procedures including venipuncture for the collection Of up to 20 ml of whole blood into EDTA-K2 spray-dried 10 ml Vacutainers (EDTA tubes; Becton Dickinson, Franklin Lakes, N.J.). Samples were refrigerated or stored on wet ice and processed to Plasma within 6 hours of the blood draw. Blood was processed and DNA isolated as previously Described (Palomaki et al., (2011) Genet Med 13:913-20). Sequencing libraries were prepared From extracted ccf DNA as previously described (Jensen T J, et al., (2013) Plos One 8:e57381). For genomic DNA, sequencing libraries were prepared according to the manufacturer's instructions (Truseq; Illumine). Paired end sequencing was performed for 100 cycles for all prepared libraries or library mixtures using an Illumina HiSeq2000 sequencer.

Data and Results

Four samples were used in this study (Table 2). Mixture B was a genomic DNA sample sheared to simulate ccf DNA fragment length distributions and mixed with ccf DNA derived from the plasma of a non-pregnant female donor with no known structural rearrangements at various concentrations. Genomic DNA was obtained from the Coriell Institute.

TABLE 2

Description and karyotype results of the 4 samples used in the study.

| Sample | Comments | Sample Information | Karyotype | Flow Cell Lanes |
|---|---|---|---|---|
| Mixtures B | Plasma A + 15% sheared genomic | NA20569 | | 9 |
| Mixtures B | Plasma A + 30% sheared genomic | NA20569 | | 6 |
| Mixtures B | Plasma A + 50% sheared genomic | NA20569 | | 3 |
| Mixtures B | 100% sheared genomic | NA20569 | 46, XY, t(2; 22)(q23; q13) | 11 |
| Plasma A | | NonPregnant Plasma | | 6 |
| Plasma B | | Pregnant Plasma | fetal 46, xx inv(9)(p12q13) | 12 |
| Plasma C | | Pregnant Plasma | fetal balanced translocation 46, XY, t(8; 11) (p11.2; p11.2) | 12 |

The data filtering steps illustrated in Table 3 shows paired end read selection based on disconcordance (i.e., discordancy), base score quality, mapping/alignment characteristic, and false positive consistency checks.

TABLE 3

Sequence read counts for each of the sequenced samples at each of the data processing steps.

| | Mixtures* B | Plasma A | Plasma B | Plasma C |
|---|---|---|---|---|
| Total Reads | 4.93E+09 | 1.43E+09 | 2.42E+09 | 2.732E+09 |
| Coverage | 264 | 77 | 130 | 146 |
| FILTER 1 | | | | |
| Discordant Paired End | 1.02E+09 | 2.13E+08 | 1.81E+08 | 5.76E+08 |
| Discordant Rates (%) | 20.77 | 14.89 | 7.48 | 21.09 |
| FILTER 2 | | | | |
| Remove reads with >10% poor quality bases for both mate pairs | 1.75E+08 | 1.46E+07 | 2.90E+07 | 1.05E+08 |
| Remove PCR duplicates | | | | |
| Remove reads with stepwise multiple alignments | | | | |
| FILTER 3 | | | | |
| Remove reads that fall alignment characteristics | 1.11E+07 | 3.32E+06 | 3.47E+06 | 3.42E+07 |
| FILTER 4 | | | | |
| Remove unmappable reads | 1.13E+06 | 4.95E+05 | 5.81E+05 | 2.41E+07 |
| Remove mitochondrial reads | | | | |
| Select putative translocation | | | | |
| FILTER 5 | | | | |
| Remove singleton reads (400 bp window) | 1.96E+03 | 4.49E+02 | 1.13E+03 | 1.11E+05 |
| Remove centromere alignments | | | | |
| RepeatMask | | | | |
| FILTER 6 | | | | |
| Remove reads consistent with controls | 65 | | | 76 |
| Joint Z scores >5 (p < $10^6$–7) | | | | |
| Number of Regions identified | 2 | | | 1 |

False positive consistency checks utilized a control data set and removed structural rearrangements found in both data sets. A putative structural rearrangement between chromosome 2 and 5 was found in both the test and pooled "control" set (FIG. 5) suggesting that this region is likely to be a false positive. Subsequent data filtering identified 65 and 76 putative paired end reads containing structural rearrangements with Z scores>5 corresponding to 2 and 1 regions for Mixture B and Plasma C, respectively. Z scores were calculated according to equation A;

$$Z = \frac{(X_a - X_b) - (\mu_a - \mu_b)}{\sqrt{(\sigma_a^2 + \sigma_b^2)}} \quad (A)$$

where a and b are the test and pooled "control" set and based on the distributions of putative translocation events at a 1 Mb resolution, which were assumed normal.

Figure 5B:
FIG. 5A-B shows an observed, likely false positive, translocation between chromosome 2 and 5 for Mixture B (FIG. 5A) and the "pooled" control set (FIG. 5B). Grey bars indicate regions of repetitive elements. The left and right coordinates corresponds to chromosome 2 and 5 (hg19), respectively.
Figure 5A:
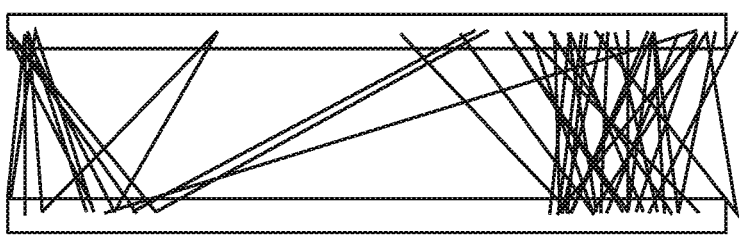

Mixture B was a model system with sheared genomic DNA, fragmented to approximate the size of ccf DNA, from a known translocation of t(2;22)(q23;q13), and mixed at various concentrations with a non-pregnant plasma sample. After data filtering, two putative translocations were identified between chromosomes 4 (152 Mb) and 11 (67 Mb) and chromosomes 2 (149 Mb) and 22 (45 Mb). Although the putative chromosome 4/11 translocation was highly significant (Z=6.50, p=4.02e-11), the boundary of the junction (position 106 of the manually assembled 213 bp region) contained several poorly annotated sequences (Table 4) suggesting that this was most likely a false positive. The second significant region involved chromosomes 2p23 and 22q13 with Z=7.52 (p=2.74e-14). Post-processing reassembly of 35 reads (4, 4, 0, and 27 reads for 15, 30, 50, and 100% genomic sheared sample, respectively) demonstrated a clear structural rearrangement with no flanking repetitive elements (FIG. 5C). The existence of the observed chromosome rearrangement was supported by the fact that no other regions between chromosomes 2 and 22 were identified and the reassembled evidence for the structural rearrangement supported previous annotations.

tions resulting in copy number neutral events including balanced translocations have proven to be more challenging and have yet to be detected non-invasively from ccf DNA.

Whole blood was collected from a 38 year-old pregnant female at 15 weeks, 5 days gestation prior to undergoing an invasive procedure. Indications for amniocentesis included advanced maternal age and a sister known to carry a balanced translocation. Results from the subsequent karyotype analysis revealed a fetal translocation occurring between the short arms of chromosomes 8 and 11 [karyotype results: balanced translocation 46 XY, t(8;11)(p11.2;p11.2)].

Prior to performing methods on the affected individual, analytical and laboratory models were developed to enable detection of fetal translocations (see Example 1). In silico data modeling was performed to evaluate multiple methods, ultimately leveraging the short length of ccf DNA and paired end sequencing to construct mapping characteristics derived by base incremental alignments. Secondly, mixtures containing a genomic DNA sample with a known translocation were created to simulate the proportion of affected DNA present in ccf DNA from a pregnant female to optimize data filtering methods.

Figure 1B:
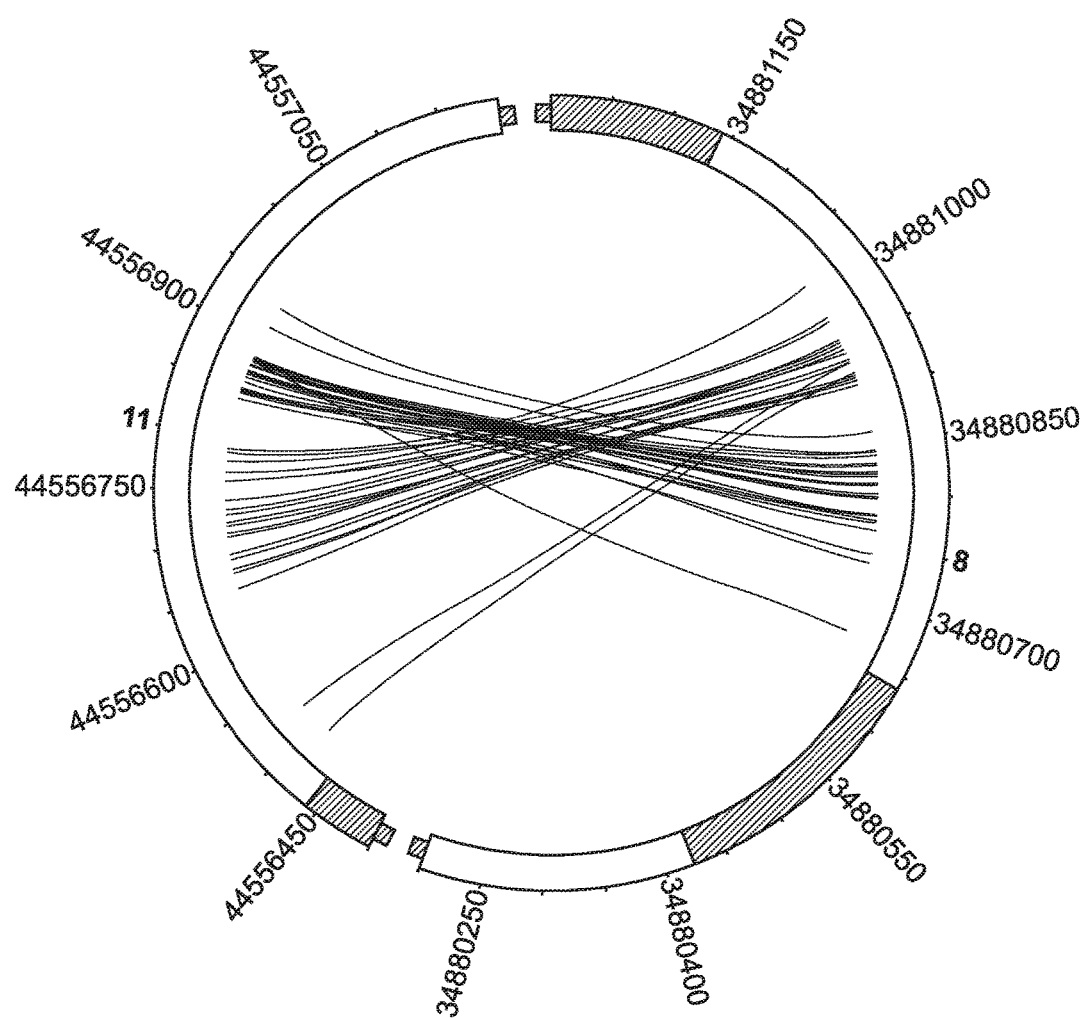
Figure 2A:
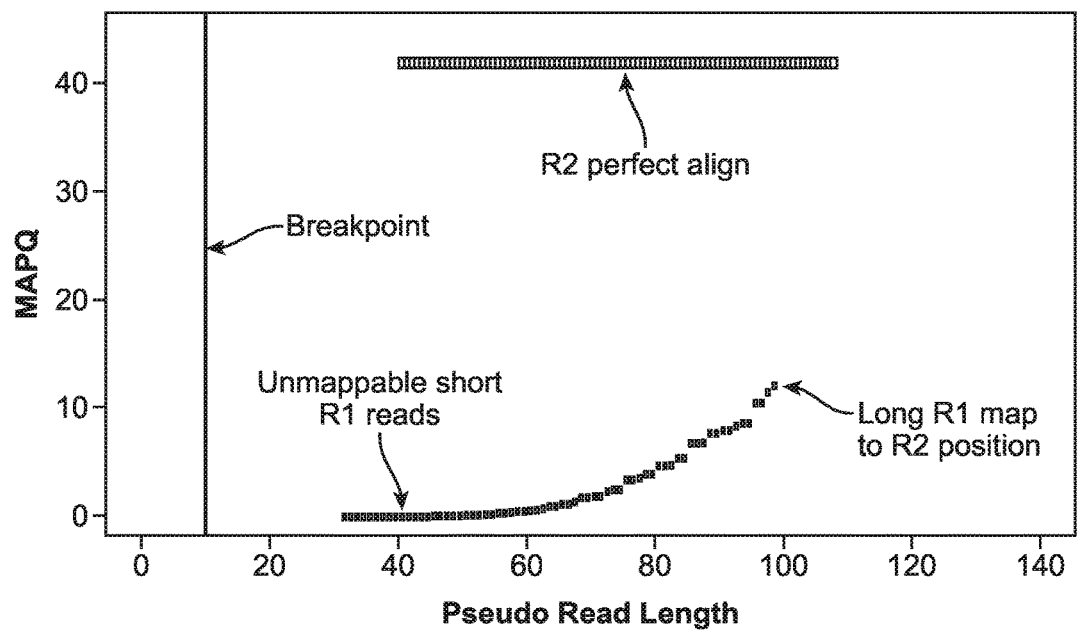
FIG. 2A-D shows average MAPQ scores for sequence read subsequences of simulated reads containing structural rearrangement breakpoints (vertical black line) at varying positions. Sequence read subsequences were generated at single base increments.
Figure 2B:
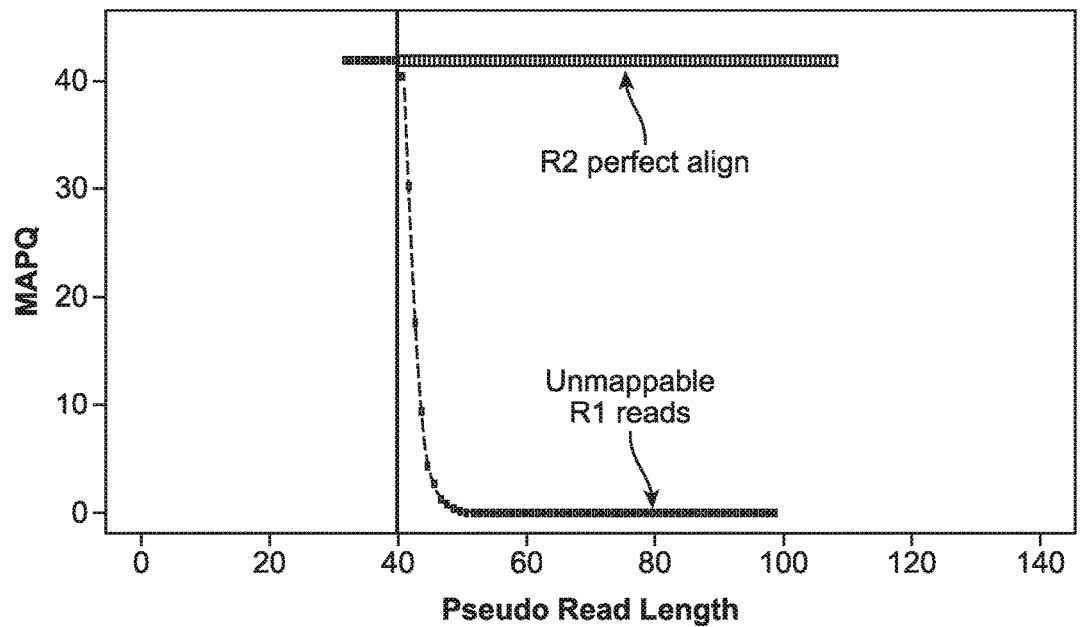
Figure 2C:
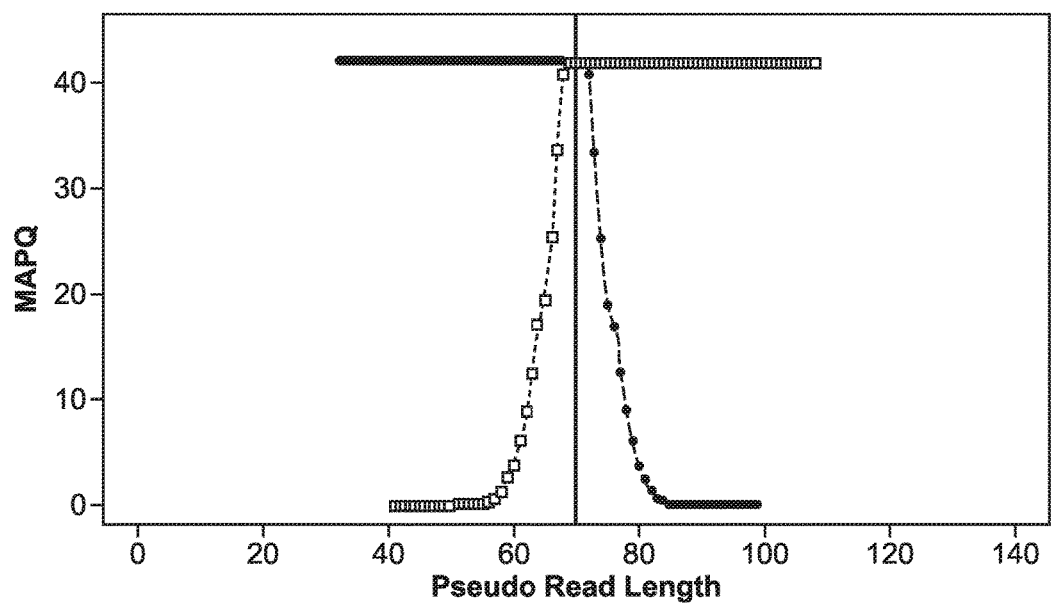
Figure 2D:
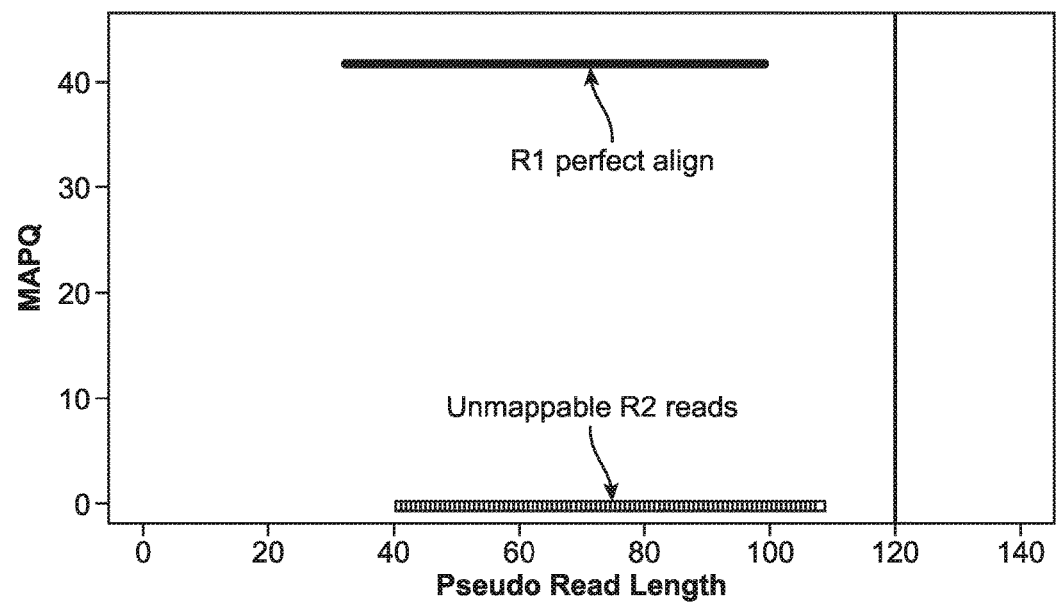

After these analytical methods were developed, the plasma ccf DNA from the mother carrying the affected fetus was isolated and analyzed. The fetal fraction in this sample was 16% and the DNA was of sufficient quality to generate a standard sequencing library. Sequencing was performed using Illumina technology, which yielded $2.7 \times 10^9$ total paired end sequencing reads. The developed methods were applied to identify the presence and precise location of the chromosomal breakpoint at single base resolution. The applied methods clearly identified the known translocation ($p=1.2 \times 10^{-8}$) and discounted the likelihood of others, enabling a putative expansion of the fetal karyotype to include a base specific breakpoint t(8;11)(34880907; 44556834)(hg19) (FIG. 1). Furthermore, a 6 bp deletion was identified at the junction of chromosome 11 and chromosome 8, which was absent from the reciprocal rearrangement (FIG. 1C).

Taken together, this data demonstrated a proof of concept for the non-invasive detection and characterization of a balanced fetal translocation event at a base specific resolution by sequencing ccf DNA from maternal plasma.

TABLE 4

BLAT9 results of the de novo assembled 213 bp region of a putative translocation found significant for mixture B.
genome.ucsc.edu/blat Results

| SCORE | START | END | QSIZE | IDENTITY | CHRO | STRAND | START | END | SPAN |
|---|---|---|---|---|---|---|---|---|---|
| 109 | 105 | 213 | 213 | 100.00% | 4 | − | 152365079 | 152365187 | 109 |
| 106 | 1 | 106 | 213 | 100.00% | 11 | + | 67766574 | 67766679 | 106 |
| 22 | 67 | 89 | 213 | 100.00% | 1 | − | 11671886 | 11671912 | 27 |
| 21 | 86 | 106 | 213 | 100.00% | 6_qbl_hap6 | + | 3210351 | 3210371 | 21 |
| 21 | 86 | 106 | 213 | 100.00% | 6_mcf_hap5 | + | 3296401 | 3296421 | 21 |
| 21 | 86 | 106 | 213 | 100.00% | 6 | + | 31916557 | 31916577 | 21 |
| 21 | 181 | 201 | 213 | 100.00% | 16 | + | 81869479 | 81869499 | 21 |
| 20 | 144 | 165 | 213 | 95.50% | 6 | − | 3156526 | 3156547 | 22 |
| 20 | 144 | 165 | 213 | 95.50% | 6 | − | 3180086 | 3180107 | 22 |

Example 2

Massively parallel sequencing of circulating cell free (ccf) DNA from maternal plasma has emerged as a predominant technology for non-invasive prenatal testing. The most established methods have utilized sequencing to detect certain autosomal trisomies and other copy number variations with high sensitivity and specificity. While the detection of CNVs has been previously described, chromosome altera- Example 3: Examples of Embodiments The examples set forth below illustrate certain embodiments and do not limit the technology.

A1. A system comprising memory and one or more microprocessors, which memory comprises instructions and which one or more microprocessors are configured to perform, according to the instructions, a process for determining the presence or absence of one or more chromosome alterations in sample nucleic acid, which process comprises:
- (a) identifying discordant read pairs from paired-end sequence reads, wherein the paired-end sequence reads are reads of circulating, cell-free nucleic acid from a test subject sample, thereby identifying discordant read mates;
- (b) characterizing the mappability of a plurality of sequence read subsequences of each discordant read mate aligned to a reference genome, each of which sequence read subsequences of each discordant read mate is of a different length;
- (c) selecting a subset of the discordant read mates according to a change in mappability, wherein the subset comprises reads comprising a candidate breakpoint;
- (d) comparing (i) the number of discordant read mates from the sample associated with the candidate breakpoints and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison; and
- (e) determining the presence or absence of one or more chromosome alterations for the sample according to the comparison in (d).

A1.1. A system comprising a sequencing apparatus and one or more computing apparatus, which sequencing apparatus is configured to produce signals corresponding to nucleotide bases of a nucleic acid loaded in the sequencing apparatus, which nucleic acid is circulating cell-free nucleic acid from a test subject sample, or which nucleic acid loaded in the sequencing apparatus is a modified variant of the circulating cell-free nucleic acid; and which one or more computing apparatus comprise memory and one or more processors, which memory comprises instructions executable by the one or more processors and which instructions executable by the one or more processors are configured to:

produce paired-end sequence reads from the signals and align the sequence reads to a reference genome;
- (a) identify discordant read pairs from the paired-end sequence reads, thereby identifying discordant read mates;
- (b) characterize the mappability of a plurality of sequence read subsequences of each discordant read mate aligned to a reference genome, each of which sequence read subsequences of each discordant read mate is of a different length;
- (c) select a subset of the discordant read mates according to a change in mappability, wherein the subset comprises reads comprising a candidate breakpoint;
- (d) compare (i) the number of discordant read mates from the sample associated with the candidate breakpoints and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison; and
- (e) determine the presence or absence of one or more chromosome alterations for the sample according to the comparison in (d).

A1.2. The system of embodiment A1 or A1.1, wherein the one or more chromosome alterations comprise a chromosome translocation.

A1.3. The system of embodiment A1 or A1.1, wherein the one or more chromosome alterations comprise a chromosome deletion.

A1.4. The system of embodiment A1 or A1.1, wherein the one or more chromosome alterations comprise a chromosome inversion.

A1.5. The system of embodiment A1 or A1.1, wherein the one or more chromosome alterations comprise a heterologous insertion.

A1.6. The system of any one of embodiments A1 to A1.5, comprising determining the position of one or more candidate breakpoints.

A2. The system of any one of embodiments A1 to A1.5, wherein the characterizing in (b) comprises generating a fitted relationship between the mappability and the length of each of the sequence read subsequences of each discordant read mate.

A3. The system of any one of embodiments A1 to A2, wherein each of the sequence read subsequences of each discordant read mate is shorter than the next largest fragment or the read mate by about 5 bases or less.

A3.1. The system of embodiment A3, wherein each of the sequence read subsequences of each discordant read mate is shorter than the next largest fragment or the read mate by 1 base or 2 bases.

A4. The system of embodiment A3, wherein each of the sequence read subsequences of each discordant read mate is incrementally shorter than the next largest fragment or the read mate.

A5. The system of embodiment A4, wherein each of the sequence read subsequences of each discordant read mate is incrementally shorter than the next largest fragment or the read mate by about 1 base.

A6. The system of any one of embodiments A2 to A5, wherein the a change in mappability comprise a slope of the fitted relationship.

A7. The system of any one of embodiments A1 to A6, wherein the selecting in (c) is according to a mappability threshold.

A8. The system of any one of embodiments A1 to A7, comprising filtering the discordant read mates.

A9. The system of embodiment A8, wherein the filtering comprises removing one or both of the discordant read mates.

A10. The system of embodiment A8 or A9, wherein the filtering is chosen from one or more of (i) removing low quality reads, (ii) removing concordant reads, (iii) removing PCR duplicated reads, (iv) removing reads mapped to mitochondrial DNA, (v) removing reads mapped to repetitive elements, (vi) removing unmappable reads, (vi) removing reads comprising step-wise multiple alignments and (vii) removing reads mapped to a centromere.

A11. The system of any one of embodiments A8 to A10, wherein the filtering comprises removing one or more singleton events.

A12. The system of any one of embodiments A8 to A10, wherein the filtering comprises removing discordant read mates in instances where the substantially similar breakpoint is present in the reference.

A13. The system of any one of embodiments A1 to A12, wherein the location of the breakpoint is identified at a single base resolution.

A14. The system of any one of embodiments A2 to A13, wherein the presence of a balanced translocation is determined in (e).

A15. The system of any one of embodiments A14, wherein the balanced translocation is a balanced translocation.

A16. The system of any one of embodiments A1 to A15, wherein the presence of an unbalanced translocation is determined in (e).

A17. The system of any one of embodiments A1 to A16, wherein determining the presence of the chromosome alteration in (e) comprises identifying a substantially greater number of sequence reads from the sample compared to the reference in the comparison of (d).

A18. The system of any one of embodiments A1 to A17, wherein a first break point and a second breakpoint are identified according to the comparison in (d).

A19. The system of embodiment A18, wherein the presence of a chromosome alteration is identified in (e) according to the first and second breakpoints.

A20. The system of any one of embodiments A1 to A19, wherein the selecting in (c) or the comparing in (d), or the selecting in (c) and the comparing in (d), does not comprise performing a clustering analysis.

A21. The system of any one of embodiments A1 to A20, wherein the comparison in (d) comprises determining a level of confidence.

A22. The system of embodiment A21, wherein determining the level of confidence comprises determining a p value.

A23. The system of embodiment A21, wherein determining the level of confidence comprises determining a Z-score.

A24. The system of any one of embodiments A1 to A23, which comprises one or more machines.

A25. The system of embodiment A24, which comprises a sequencing machine configured to generate the sequence reads.

A26. The system of embodiment A24 or A25, which is embodied in one machine.

A27. The system of any one of embodiments A1 to A26, wherein the memory comprises the sequence reads, the discordant read pairs, the subset of discordant read mates, the change in mappability, the breakpoints, or a combination thereof.

A28. The system of any one of embodiments A1 to A27, wherein the sample nucleic acid is circulating cell-free nucleic acid from a pregnant female bearing a fetus.

A29. The system of any one of embodiments A1 to A27, wherein the sample nucleic acid is circulating cell-free nucleic acid from a subject having or suspected of having a cell proliferative disorder.

A30. The system of embodiment A29, wherein the cell proliferative disorder is cancer.

A31. The system of any one of embodiments A1 to A30, wherein the presence or absence of one or more chromosome alterations is determined for a minority nucleic acid species.

A32. The system of embodiment A31, wherein the minority nucleic acid species comprises fetal nucleic acid.

A33. The system of embodiment A31, wherein the minority nucleic acid species comprises nucleic acid from cancer cells.

B1. A method of determining the presence or absence of one or more chromosome alterations in sample nucleic acid, comprising:
(a) identifying discordant read pairs from paired-end sequence reads, wherein the paired-end sequence reads are reads of circulating, cell-free nucleic acid from a test subject sample, thereby identifying discordant read mates;

(b) characterizing the mappability of a plurality of sequence read subsequences of each discordant read mate aligned to a reference genome, each of which sequence read subsequences of each discordant read mate is of a different length;

(c) selecting a subset of the discordant read mates according to a change in mappability, wherein the subset comprises reads comprising a candidate breakpoint;

(d) comparing (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison; and (e) determining the presence or absence of one or more chromosome alterations for the sample according to the comparison in (d).

B1.1. A method of determining the presence or absence of one or more chromosome alterations in sample nucleic acid, comprising:

loading a sequencing apparatus with circulating cell-free nucleic acid from a test sample, or loading the sequencing apparatus with a modified variant of the nucleic acid, which sequencing apparatus produces signals corresponding to nucleotide bases of the nucleic acid;

generating paired-end sequence reads from the signals of the nucleic acid by, after optionally transferring the signals to, a system comprising one or more computing apparatus, wherein the one or more computing apparatus in the system comprise memory and one or more processors, and determining the presence or absence of one or more chromosome alterations in the sample nucleic acid by the system, wherein one computing apparatus, or combination of computing apparatus, in the system is configured to:

align the sequence reads to a reference genome;

(a) identify discordant read pairs from the paired-end sequence reads thereby identifying discordant read mates;

(b) characterize the mappability of a plurality of sequence read subsequences of each discordant read mate aligned to a reference genome, each of which sequence read subsequences of each discordant read mate is of a different length;

(c) select a subset of the discordant read mates according to a change in mappability, wherein the subset comprises reads comprising a candidate breakpoint;

(d) compare (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison; and (e) determine the presence or absence of one or more chromosome alterations for the sample according to the comparison in (d).

B1.2. The method of embodiment B1 or B1.1, wherein the one or more chromosome alterations comprise a chromosome translocation.
B1.3. The method of embodiment B1 or B1.1, wherein the one or more chromosome alterations comprise a chromosome deletion.
B1.4. The method of embodiment B1 or B1.1, wherein the one or more chromosome alterations comprise a chromosome inversion.
B1.5. The method of embodiment B1 or B1.1, wherein the one or more chromosome alterations comprise a heterologous insertion.
B1.6. The method of any one of embodiments B1 to B1.5, comprising determining the position of one or more candidate breakpoints.
B2. The method of any one of embodiments B1 to B1.6, wherein the characterizing in (b) comprises generating a fitted relationship between the mappability and the length of each of the sequence read subsequences of each discordant read mate.
B3. The method of any one of embodiments B1 to B2, wherein each of the sequence read subsequences of each discordant read mate is shorter than the next largest fragment or the read mate by about 5 bases or less.
B3.1. The method of embodiment B3, wherein each of the sequence read subsequences of each discordant read mate is shorter than the next largest fragment or the read mate by 1 base or 2 bases.
B4. The method of embodiment B3, wherein each of the sequence read subsequences of each discordant read mate is incrementally shorter than the next largest fragment or the read mate.
B5. The method of embodiment B4, wherein each of the sequence read subsequences of each discordant read mate is incrementally shorter than the next largest fragment or the read mate by about 1 base.
B6. The method of any one of embodiments B2 to B5, wherein the change in mappability is determined from a slope in the fitted relationship.
B6.1. The method of any one of embodiments B2 to B5, wherein the change in mappability comprise a slope of the fitted relationship.
B7. The method of any one of embodiments B1 to B6, wherein the selecting in (c) is according to a mappability threshold.
B8. The method of any one of embodiments B1 to B7, comprising filtering the discordant read mates.
B9. The method of embodiment B8, wherein the filtering comprises removing one or both of the discordant read mates.
B10. The method of embodiment B8 or B9, wherein the filtering is chosen from one or more of (i) removing low quality reads, (ii) removing concordant reads, (iii) removing PCR duplicated reads, (iv) removing reads mapped to mitochondrial DNA, (v) removing reads mapped to repetitive elements, (vi) removing unmappable reads, (vii) removing reads comprising step-wise multiple alignments and (viii) removing reads mapped to a centromere.
B11. The method of any one of embodiments B8 to B10, wherein the filtering comprises removing one or more singleton events.
B12. The method of any one of embodiments B8 to B10, wherein the filtering comprises removing discordant read mates in instances where the substantially similar breakpoint is present in the reference.
B13. The method of any one of embodiments B1 to B12, wherein the location of the breakpoint is identified at a single base resolution.
B14. The method of any one of embodiments B1 to B13, wherein the presence of a balanced translocation is determined in (e).
B15. The method of embodiment B14, wherein the balanced translocation is a balanced translocation.
B16. The method of any one of embodiments B1 to B15, wherein the presence of an unbalanced translocation is determined in (e).
B17. The method of any one of embodiments B1 to B16, wherein determining the presence of the chromosome alteration in (e) comprises identifying a substantially greater number of sequence reads from the sample compared to the reference in the comparison of (d).
B18. The method of any one of embodiments B1 to B17, wherein a first break point and a second breakpoint are identified according to the comparison in (d).
B19. The method of embodiment B18, wherein the presence of a chromosome alteration is identified in (e) according to the first and second breakpoints.
B20. The method of any one of embodiments B1 to B19, wherein the selecting in (c) or the comparing in (d), or the selecting in (c) and the comparing in (d), does not comprise performing a clustering analysis.
B21. The method of any one of embodiments B1 to B20, wherein the comparison in (d) comprises determining a level of confidence.
B22. The method of embodiment B21, wherein determining the level of confidence comprises determining a p value.
B23. The method of embodiment B21, wherein determining the level of confidence comprises determining a Z-score.
B24. The method of any one of embodiments B1 to B23, which comprises one or more machines.
B25. The method of embodiment B24, which comprises a sequencing machine configured to generate the sequence reads.
B26. The method of embodiment B24 or B25, which is embodied in one machine.
B27. The method of any one of embodiments B1 to B26, which comprises obtaining the sequence reads, the discordant read pairs, the subset of discordant read mates, the change in mappability, the breakpoints, or a combination thereof.
B28. The method of any one of embodiments B1 to B27, wherein the sample nucleic acid is circulating cell-free nucleic acid from a pregnant female bearing a fetus.
B29. The method of any one of embodiments B1 to B27, wherein the sample nucleic acid is circulating cell-free nucleic acid from a subject having or suspected of having a cell proliferative disorder.
B30. The method of embodiment B29, wherein the cell proliferative disorder is cancer.
B31. The method of any one of embodiments B1 to B30, wherein the presence or absence of one or more chromosome alterations is determined for a minority nucleic acid species.
B32. The method of embodiment B31, wherein the minority nucleic acid species comprises fetal nucleic acid.
B33. The method of embodiment B31, wherein the minority nucleic acid species comprises nucleic acid from cancer cells.
C1. An apparatus comprising one or more processors and memory, which memory comprises instructions executable by the one or more processors and which memory comprises nucleic acid sequence reads mapped to a reference genome; and which instructions executable by the one or more processors are configured to:
  (a) identify discordant read pairs from paired-end sequence reads, wherein the paired-end sequence reads are reads of circulating, cell-free nucleic acid from a test subject sample, thereby identifying discordant read mates;
  (b) characterize the mappability of a plurality of sequence read subsequences of each discordant read mate aligned to a reference genome, each of which sequence read subsequences of each discordant read mate is of a different length;
  (c) select a subset of the discordant read mates according to a change in mappability, wherein the subset comprises reads comprising a candidate breakpoint;
  (d) compare (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison; and
  (e) determine the presence or absence of one or more chromosome alterations for the sample according to the comparison in (d).

C1.1. The apparatus of embodiment C1, wherein the one or more chromosome alterations comprise a chromosome translocation.

C1.2. The apparatus of embodiment C1, wherein the one or more chromosome alterations comprise a chromosome deletion.

C1.3. The apparatus of embodiment C1, wherein the one or more chromosome alterations comprise a chromosome inversion.

C1.4. The apparatus of embodiment C1, wherein the one or more chromosome alterations comprise a heterologous insertion.

C1.5. The apparatus of any one of embodiments C1 to C1.4, comprising determining the position of one or more candidate breakpoints.

C2. The apparatus of any one of embodiments C1 to C1.5, wherein the characterizing in (b) comprises generating a fitted relationship between the mappability and the length of each of the sequence read subsequences of each discordant read mate.

C3. The apparatus of any one of embodiments C1 to C2, wherein each of the sequence read subsequences of each discordant read mate is shorter than the next largest fragment or the read mate by about 5 bases or less.

C3.1. The apparatus of embodiment C3, wherein each of the sequence read subsequences of each discordant read mate is shorter than the next largest fragment or the read mate by 1 base or 2 bases.

C4. The apparatus of embodiment C3, wherein each of the sequence read subsequences of each discordant read mate is incrementally shorter than the next largest fragment or the read mate.

C5. The apparatus of embodiment C4, wherein each of the sequence read subsequences of each discordant read mate is incrementally shorter than the next largest fragment or the read mate by about 1 base.

C6. The apparatus of any one of embodiments C2 to C5, wherein the change in mappability comprise a slope of the fitted relationship.

C7. The apparatus of any one of embodiments C1 to C6, wherein the selecting in (c) is according to a mappability threshold.

C8. The apparatus of any one of embodiments C1 to C7, comprising instructions executable by the one or more processors configured to filter the discordant read mates.

C9. The apparatus of embodiment C8, wherein the filtering comprises removing one or both of the discordant read mates.

C10. The apparatus of embodiment C8 or C9, wherein the filtering is chosen from one or more of (i) removing low quality reads, (ii) removing concordant reads, (iii) removing PCR duplicated reads, (iv) removing reads mapped to mitochondrial DNA, (v) removing reads mapped to repetitive elements, (vi) removing unmappable reads, (vi) removing reads comprising step-wise multiple alignments and (vii) removing reads mapped to a centromere.

C11. The apparatus of any one of embodiments C8 to C10, wherein the filtering comprises removing one or more singleton events.

C12. The apparatus of any one of embodiments C8 to C10, wherein the filtering comprises removing discordant read mates in instances where the substantially similar breakpoint is present in the reference.

C13. The apparatus of any one of embodiments C1 to C12, wherein the location of the breakpoint is identified at a single base resolution.

C14. The apparatus of any one of embodiments C2 to C13, wherein the presence of a balanced translocation is determined in (e).

C15. The apparatus of any one of embodiments C14, wherein the balanced translocation is a balanced translocation.

C16. The apparatus of any one of embodiments C1 to C15, wherein the presence of an unbalanced translocation is determined in (e).

C17. The apparatus of any one of embodiments C1 to C16, wherein determining the presence of the translocation in (e) comprises identifying a substantially greater number of sequence reads from the sample compared to the reference in the comparison of (d).

C18. The apparatus of any one of embodiments C1 to C17, wherein a first break point and a second breakpoint are identified according to the comparison in (d).

C19. The apparatus of embodiment C18, wherein the presence of a chromosome alteration is identified in (e) according to the first and second breakpoints.

C20. The apparatus of any one of embodiments C1 to C19, wherein the selecting in (c) or the comparing in (d), or the selecting in (c) and the comparing in (d), does not comprise performing a clustering analysis.

C21. The apparatus of any one of embodiments C1 to C20, wherein the comparison in (d) comprises determining a level of confidence.

C22. The apparatus of embodiment C21, wherein determining the level of confidence comprises determining a p value.

C23. The apparatus of embodiment C21, wherein determining the level of confidence comprises determining a Z-score.

C24. The apparatus of any one of embodiments C1 to C23, which comprises one or more machines.

C25. The apparatus of embodiment C24, which comprises a sequencing machine configured to generate the sequence reads.

C26. The apparatus of embodiment C24 or C25, which is embodied in one machine.

C27. The apparatus of any one of embodiments C1 to C26, wherein the memory comprises the sequence reads, the discordant read pairs, the subset of discordant read mates, the change in mappability, the candidate breakpoints, or a combination thereof.

C28. The apparatus of any one of embodiments C1 to C27, wherein the sample nucleic acid is circulating cell-free nucleic acid from a pregnant female bearing a fetus.

C29. The apparatus of any one of embodiments C1 to C27, wherein the sample nucleic acid is circulating cell-free nucleic acid from a subject having or suspected of having a cell proliferative disorder.

C30. The apparatus of embodiment C29, wherein the cell proliferative disorder is cancer.

C31. The apparatus of any one of embodiments C1 to C30, wherein the presence or absence of one or more chromosome alterations is determined for a minority nucleic acid species.

C32. The apparatus of embodiment C31, wherein the minority nucleic acid species comprises fetal nucleic acid.

C33. The apparatus of embodiment C31, wherein the minority nucleic acid species comprises nucleic acid from cancer cells.

D1. A non-transitory computer-readable storage medium with an executable program stored thereon, which program is configured to instruct a microprocessor to:
  (a) identify discordant read pairs from paired-end sequence reads, wherein the paired-end sequence reads are reads of circulating, cell-free nucleic acid from a test subject sample, thereby identifying discordant read mates;
  (b) characterize the mappability of a plurality of sequence read subsequences of each discordant read mate aligned to a reference genome, each of which sequence read subsequences of each discordant read mate is of a different length;
  (c) select a subset of the discordant read mates according to a change in mappability, wherein the subset comprises reads comprising a candidate breakpoint;
  (d) compare (i) the number of discordant read mates from the sample associated with a candidate breakpoint and optionally one or more substantially similar breakpoints, to (ii) the number of discordant read mates from a reference associated with the candidate breakpoint and optionally the one or more substantially similar breakpoints, for the discordant read mates in the subset selected in (c), thereby generating a comparison; and
  (e) determine the presence or absence of one or more chromosome alterations for the sample according to the comparison in (d).

D1.1. The storage medium of embodiment D1, wherein the one or more chromosome alterations comprise a chromosome translocation.

D1.2. The storage medium of embodiment D1, wherein the one or more chromosome alterations comprise a chromosome deletion.

D1.3. The storage medium of embodiment D1, wherein the one or more chromosome alterations comprise a chromosome inversion.

D1.4. The storage medium of embodiment D1, wherein the one or more chromosome alterations comprise a heterologous insertion.

D1.5. The storage medium of any one of embodiments D1 to D1.4, where the program instructs a microprocessor to determine the position of one or more candidate breakpoints.

D2. The storage medium of any one of embodiments D1 to D1.5, wherein the characterizing in (b) comprises generating a fitted relationship between the mappability and the length of each of the sequence read subsequences of each discordant read mate.

D3. The storage medium of any one of embodiments D1 to D2, wherein each of the sequence read subsequences of each discordant read mate is shorter than the next largest fragment or the read mate by about 5 bases or less.

D3.1. The storage medium of any one of embodiments D1 to D3, wherein each of the sequence read subsequences of each discordant read mate is shorter than the next largest fragment or the read mate by 1 base or 2 bases.

D4. The storage medium of any one of embodiments D1 to D3.1, wherein each of the sequence read subsequences of each discordant read mate is incrementally shorter than the next largest fragment or the read mate.

D5. The storage medium of any one of embodiments D1 to D4, wherein each of the sequence read subsequences of each discordant read mate is incrementally shorter than the next largest fragment or the read mate by about 1 base.

D6. The storage medium of any one of embodiments D2 to D5, wherein the change in mappability comprise a slope of the fitted relationship.

D7. The storage medium of any one of embodiments D1 to D6, wherein the selecting in (c) is according to a mappability threshold.

D8. The storage medium of any one of embodiments D1 to D7, wherein the program instructs the processor to filter the discordant read mates.

D9. The storage medium of embodiment D8, wherein the filtering comprises removing one or both of the discordant read mates.

D10. The storage medium of embodiment D8 or D9, wherein the filtering is chosen from one or more of (i) removing low quality reads, (ii) removing concordant reads, (iii) removing PCR duplicated reads, (iv) removing reads mapped to mitochondrial DNA, (v) removing reads mapped to repetitive elements, (vi) removing unmappable reads, (vi) removing reads comprising step-wise multiple alignments and (vii) removing reads mapped to a centromere.

D11. The storage medium of any one of embodiments D8 to D10, wherein the filtering comprises removing one or more singleton events.

D12. The storage medium of any one of embodiments D8 to D10, wherein the filtering comprises removing discordant read mates in instances where the substantially similar breakpoint is present in the reference.

D13. The storage medium of any one of embodiments D1 to D12, wherein the location of the breakpoint is identified at a single base resolution.

D14. The storage medium of any one of embodiments D1 to D13, wherein the presence of a balanced translocation is determined in (e).

D15. The storage medium of any one of embodiments D14, wherein the balanced translocation is a balanced translocation.

D16. The storage medium of any one of embodiments D1 to D15, wherein the presence of an unbalanced translocation is determined in (e).

D17. The storage medium of any one of embodiments D1 to D16, wherein determining the presence of the chromosome alteration in (e) comprises identifying a substantially greater number of sequence reads from the sample compared to the reference in the comparison of (d).

D18. The storage medium of any one of embodiments D1 to D17, wherein a first break point and a second breakpoint are identified according to the comparison in (d).

D19. The storage medium of embodiment D18, wherein the presence of a chromosome alteration is identified in (e) according to the first and second breakpoints.

D20. The storage medium of any one of embodiments D1 to D19, wherein the selecting in (c) or the comparing in (d), or the selecting in (c) and the comparing in (d), does not comprise performing a clustering analysis.

D21. The storage medium of any one of embodiments D1 to D20, wherein the comparison in (d) comprises determining a level of confidence.

D22. The storage medium of embodiment D21, wherein determining the level of confidence comprises determining a p value.

D23. The storage medium of embodiment D21, wherein determining the level of confidence comprises determining a Z-score.

D24. The storage medium of any one of embodiments D1 to D23, which comprises one or more machines.

D25. The storage medium of embodiment D24, which comprises a sequencing machine configured to generate the sequence reads.

D26. The storage medium of embodiment D24 or D25, which is embodied in one machine.

D27. The storage medium of any one of embodiments D1 to D26, wherein the storage medium comprises the sequence reads, the discordant read pairs, the subset of discordant read mates, the change in mappability, the breakpoints, or a combination thereof.

D28. The storage medium of any one of embodiments D1 to D27, wherein the sample nucleic acid is circulating cell-free nucleic acid from a pregnant female bearing a fetus.

D29. The storage medium of any one of embodiments D1 to D27, wherein the sample nucleic acid is circulating cell-free nucleic acid from a subject having or suspected of having a cell proliferative disorder.

D30. The storage medium of embodiment D29, wherein the cell proliferative disorder is cancer.

D31. The storage medium of any one of embodiments D1 to D30, wherein the presence or absence of one or more chromosome alterations is determined for a minority nucleic acid species.

D32. The storage medium of embodiment D31, wherein the minority nucleic acid species comprises fetal nucleic acid.

D33. The storage medium of embodiment D31, wherein the minority nucleic acid species comprises nucleic acid from cancer cells.

E1. A system comprising memory and one or more microprocessors, which memory comprises instructions and which one or more microprocessors are configured to perform, according to the instructions, a process for determining the presence or absence of one or more chromosome alterations in sample nucleic acid, which process comprises:
  (a) characterizing mappability of a plurality of sequence read subsequences for sequence reads, wherein:
    there are multiple sequence read subsequences for each sequence read,
    the sequence read subsequences for each sequence read are of different lengths, and
    the sequence reads are of the sample nucleic acid;
  (b) identifying a subset of sequence reads for which there is a change in mappability of one or more subsequences;
  (c) comparing (i) the number of each of the sequence reads in the subset identified in (b) from the sample, to (ii) the number of each of the sequence reads in the subset identified in
  (b) from a reference, thereby generating a comparison; and
  (d) determining the presence or absence of one or more chromosome alterations for the sample according to the comparison in (c).

E1.1. A system comprising a sequencing apparatus and one or more computing apparatus,
  which sequencing apparatus is configured to produce signals corresponding to nucleotide bases of a nucleic acid loaded in the sequencing apparatus, which nucleic acid is circulating cell-free nucleic acid from a test subject sample, or which nucleic acid loaded in the sequencing apparatus is a modified variant of the circulating cell-free nucleic acid; and
  which one or more computing apparatus comprise memory and one or more processors, which memory comprises instructions executable by the one or more processors and which instructions executable by the one or more processors are configured to:
  produce sequence reads from the signals and align the sequence reads to a reference genome;
    (a) characterize mappability of a plurality of sequence read subsequences for the sequence reads, wherein:
      there are multiple sequence read subsequences for each sequence read,
      the sequence read subsequences for each sequence read are of different lengths, and
      the sequence reads are of the sample nucleic acid;
    (b) identify a subset of sequence reads for which there is a change in mappability of one or more subsequences;
    (c) compare (i) the number of each of the sequence reads in the subset identified in (b) from the sample, to (ii) the number of each of the sequence reads in the subset identified in (b) from a reference, thereby generating a comparison; and
    (d) determine the presence or absence of one or more chromosome alterations for the sample according to the comparison in (c).

E2. The system of embodiment E1 or E1.1, wherein the sequence reads are of circulating, cell-free nucleic acid.

E3. The system of embodiment E1, E1.1 or E2, wherein the average length of a polynucleotide in the sample nucleic acid is less than about 300 base pairs.

E4. The system of embodiment E2 or E3, wherein the circulating, cell-free nucleic acid is from serum or plasma.

E5. The system of any one of embodiments E1 to E4, wherein the sequence reads have been mapped to a reference genome or portion thereof.

E6. The system of embodiment E5, comprising, prior to (a), identifying a subset of sequence reads for which all bases do not align with the reference genome or portion thereof, and performing (a), (b), (c) and (d) for the subset.

E7. The system of any one of embodiments E1 to E6, wherein the sequence reads are single-end sequence reads.

E7.1. The system of any one of embodiments E1 to E7, wherein the sequence reads are discordant reads.

E7.2. The system of embodiment E7.1, wherein the change in mappability is determined for the discordant reads.

E8. The system of any one of embodiments E1 to E6, wherein the sequence reads are paired-end sequence reads.

E9. The system of embodiments E8, wherein the sequence reads are discordant read pairs.

E10. The system of any one of embodiments E1 to E9.1, comprising identifying discordant read pairs thereby providing discordant read mates.

E10.1. The system of embodiment E10, wherein the change in mappability is determined for the discordant read mates.

E11. The system of any one of embodiments E1 to E10.1, wherein chimeric read pairs are not identified prior to (a).

E12. The system of any one of embodiments E1 to E11, comprising identifying a candidate breakpoint for each sequence read in the subset prior to the comparing in (c).

E13. The system of embodiment E12, wherein the candidate breakpoint for each sequence read is identified according to the change in the mappability.

E14. The system of embodiment E12 or E13, wherein the comparing in (c) comprises comparing (i) the number of each of the sequence reads in the subset identified in (b) from the sample associated with the candidate breakpoint, to (ii) the number of each of the sequence reads in the subset identified in (b) from a reference associated with the candidate breakpoint.

E15. The system of any one of embodiments E1 to E14, wherein the sequence reads have a minimum length of about 32 contiguous bases in the subset identified in (b).

E16. The system of any one of embodiments E12 to E15, wherein there are at least about 15 contiguous bases to about 20 contiguous bases on each side of the candidate breakpoint in each of the sequence reads in the subset identified in (b).

E17. The system of any one of embodiments E1 to E16, wherein the sequence reads are of nucleic acid fragments having an average, mean, median or maximum length of about 20 bases to about 500 bases.

E17.1. The system of embodiment E17, wherein the sequence reads are of nucleic acid fragments having an average, mean, median or maximum length of about 40 bases to about 500 bases.

E18. The system of any one of embodiments E1 to E17.1, wherein the one or more chromosome alterations comprise a chromosome translocation.

E18.1 The system of any one of embodiments E1 to E18, wherein the one or more chromosome alterations comprise a balanced chromosome translocation.

E19. The system of any one of embodiments E1 to E17, wherein the one or more chromosome alterations comprise a chromosome deletion.

E20. The system of any one of embodiments E1 to E17, wherein the one or more chromosome alterations comprise a chromosome inversion.

E21. The system of any one of embodiments E1 to E17, wherein the one or more chromosome alterations comprise a heterologous insertion.

E22. The system of any one of embodiments E1 to E21, comprising providing a position of one or more breakpoints in instances where the presence of the one or more chromosome alterations is determined in (d).

E23. The system of embodiment E22, wherein the position of each of the one or more breakpoints is provided with a one base pair resolution.

E24. The system of any one of embodiments E1 to E23, wherein the identifying in (b) comprises generating a fitted relationship between the mappability and the length of each of the sequence read subsequences of each of the reads.

E25. The system of embodiment E24, wherein the change in mappability is determined from a slope in the relationship.

E26. The system of any one of embodiments E1 to E25, wherein sequence reads, for which there is alignment of sequence read subsequences of increasing length to a first chromosome, followed by alignment to a second chromosome and then followed by alignment to the first chromosome, are not included in the subset identified in (b).

E26.1. The system of any one of embodiments E1 to E26, wherein sequence reads, for which there is alignment of sequence read subsequences of increasing length to a first chromosome, followed by alignment to a second chromosome are included in the subset identified in (b).

E27. The system of any one of embodiments E1 to E26.1, wherein the comparison in (c) is determined according to a z-score between the number of sequence reads in (c)(i) and the number of sequence reads in (c)(ii).

E28. The system of any one of embodiments E12 to E27, wherein each of the sequence reads in the subset identified in (b) comprises substantially similar candidate breakpoints.

E29. The system of any one of embodiments E1 to E28, wherein each of the sequence read subsequences of each read is shorter than the next largest fragment or the read by about 5 bases or less.

E30. The system of embodiment E29, wherein each of the sequence read subsequences of each read is shorter than the next largest fragment or the read by 1 base or 2 bases.

E31. The system of embodiment E30, wherein each of the sequence read subsequences of each read is incrementally shorter than the next largest fragment or the read.

E32. The system of embodiment E31, wherein each of the sequence read subsequences of each read is incrementally shorter than the next largest fragment or the read by about 1 base.

E33. The system of any one of embodiments E24 to E32, wherein the characterizing the mappability of a plurality of sequence read subsequences comprises determining a slope of the fitted relationship.

E34. The system of any one of embodiments E1 to E33, wherein the identifying in (b) is according to a mappability threshold.

E35. The system of any one of embodiments E1 to E34, comprising filtering reads.

E36. The system of any one of embodiments E10 to E34, wherein the filtering comprises removing one or both of the discordant read mates.

E37. The system of embodiment E35 or E36, wherein the filtering is chosen from one or more of (i) removing low quality reads, (ii) removing concordant reads, (iii) removing PCR duplicated reads, (iv) removing reads mapped to mitochondrial DNA, (v) removing reads mapped to repetitive elements, (vi) removing unmappable reads, (vi) removing reads comprising step-wise multiple alignments and (vii) removing reads mapped to a centromere.

E38. The system of any one of embodiments E35 to E37, wherein the filtering comprises removing one or more singleton events.

E39. The method of any one of embodiments E35 to E38, wherein the filtering comprises removing the subset of reads identified in (b) in instances where the number of each of the sequence reads in the subset from the sample are substantially similar to the number of each of the sequence reads in the subset from the reference.

E40. The system of any one of embodiments E28 to E39, wherein the location of the candidate breakpoint is identified at a single base resolution.

E41. The system of any one of embodiments E1 to E40, wherein the presence of a balanced translocation is determined in (d).

E42. The system of any one of embodiments E1 to E41, wherein the presence of an unbalanced translocation is determined in (d).

E43. The system of any one of embodiments E1 to E42, wherein determining the presence of the chromosome alteration in (d) comprises identifying a substantially greater number of sequence reads from the sample compared to the reference in the comparison of (c).

E44. The system of any one of embodiments E1 to E43, wherein a breakpoint is identified according to the comparison in (c).
E45. The system of any one of embodiments E1 to E44, wherein a first breakpoint and a second breakpoint are identified according to the comparison in (c).
E46. The system of embodiment E45, wherein the presence of a chromosome alteration is identified in (d) according to the first and the second breakpoints.
E47. The system of any one of embodiments E1 to E46, wherein the comparison in (c) comprises determining a level of confidence.
E48. The system of embodiment E47, wherein determining the level of confidence comprises determining a p value.
E49. The system of embodiment E47, wherein determining the level of confidence comprises determining a Z-score.
E50. The system of any one of embodiments E1 to E49, which comprises one or more machines.
E51. The system of embodiment E50, which comprises a sequencing machine configured to generate the sequence reads.
E52. The system of embodiment E50 or E51, which is embodied in one machine.
E53. The system of any one of embodiments E1 to E52, wherein the memory comprises one or more of the sequence reads, the plurality of sequence read subsequences, the discordant read pairs, the subsets of reads, the candidate breakpoints, or a combination thereof.
E54. The system of any one of embodiments E1 to E35, wherein the sample nucleic acid is circulating cell-free nucleic acid from a pregnant female bearing a fetus.
E55. The system of any one of embodiments E1 to E53, wherein the sample nucleic acid is circulating cell-free nucleic acid from a subject having or suspected of having a cell proliferative disorder.
E56. The system of embodiment E55, wherein the cell proliferative disorder is cancer.
E57. The system of any one of embodiments E1 to E56, wherein the presence or absence of one or more chromosome alterations is determined for a minority nucleic acid species.
E58. The system of embodiment E57, wherein the minority nucleic acid species comprises fetal nucleic acid.
E59. The system of embodiment E57, wherein the minority nucleic acid species comprises nucleic acid from cancer cells.
F1. A method comprising memory and one or more microprocessors, which memory comprises instructions and which one or more microprocessors are configured to perform, according to the instructions, a process for determining the presence or absence of one or more chromosome alterations in sample nucleic acid, which process comprises:
  (a) characterizing mappability of a plurality of sequence read subsequences for sequence reads, wherein:
    there are multiple sequence read subsequences for each sequence read,
    the sequence read subsequences for each sequence read are of different lengths, and
    the sequence reads are of the sample nucleic acid;
  (b) identifying a subset of sequence reads for which there is a change in mappability of one or more subsequences;
  (c) comparing (i) the number of each of the sequence reads in the subset identified in (b) from the sample, to (ii) the number of each of the sequence reads in the subset identified in (b) from a reference, thereby generating a comparison; and
  (d) determining the presence or absence of one or more chromosome alterations for the sample according to the comparison in (c).

F1.1. A method of determining the presence or absence of one or more chromosome alterations in sample nucleic acid, comprising:
  loading a sequencing apparatus with circulating cell-free nucleic acid from a test sample, or loading the sequencing apparatus with a modified variant of the nucleic acid, which sequencing apparatus produces signals corresponding to nucleotide bases of the nucleic acid;
  generating sequence reads from the signals of the nucleic acid by, after optionally transferring the signals to, a system comprising one or more computing apparatus, wherein the one or more computing apparatus in the system comprise memory and one or more processors, and
  determining the presence or absence of one or more chromosome alterations in the sample nucleic acid by the system, wherein one computing apparatus, or combination of computing apparatus, in the system is configured to:
    align the sequence reads to a reference genome;
    (a) characterize mappability of a plurality of sequence read subsequences for the sequence reads, wherein:
      there are multiple sequence read subsequences for each sequence read,
      the sequence read subsequences for each sequence read are of different lengths, and
      the sequence reads are of the sample nucleic acid;
    (b) identify a subset of sequence reads for which there is a change in mappability of one or more subsequences;
    (c) compare (i) the number of each of the sequence reads in the subset identified in (b) from the sample, to (ii) the number of each of the sequence reads in the subset identified in (b) from a reference, thereby generating a comparison; and
    (d) determine the presence or absence of one or more chromosome alterations for the sample according to the comparison in (c).

F1.2. A method of determining the presence or absence of one or more chromosome alterations in sample nucleic acid, comprising:
  loading a sequencing apparatus with circulating cell-free nucleic acid from a test sample, or loading the sequencing apparatus with a modified variant of the nucleic acid, which sequencing apparatus produces signals corresponding to nucleotide bases of the nucleic acid;
  generating sequence reads from the signals of the nucleic acid by, after optionally transferring the signals to, a system comprising one or more computing apparatus, wherein the one or more computing apparatus in the system comprise memory and one or more processors, and
  determining the presence or absence of one or more chromosome alterations in the sample nucleic acid by the system, wherein one computing apparatus, or combination of computing apparatus, in the system is configured to:
    align the sequence reads to a reference genome;
    (a) identify discordant read pairs from the paired-end sequence reads thereby identifying discordant read mates;
    (a) characterize mappability of a plurality of sequence read subsequences for the sequence reads, wherein:
      there are multiple sequence read subsequences for each sequence read,
      the sequence read subsequences for each sequence read are of different lengths, and
      the sequence reads are of the sample nucleic acid;

(b) identify a subset of sequence reads for which there is a change in mappability of one or more subsequences;

(c) compare (i) the number of each of the sequence reads in the subset identified in (b) from the sample, to (ii) the number of each of the sequence reads in the subset identified in (b) from a reference, thereby generating a comparison; and (d) determine the presence or absence of one or more chromosome alterations for the sample according to the comparison in (c).

F2. The method of embodiment F1 or F1.1, wherein the sequence reads are of circulating, cell-free nucleic acid.

F3. The method of embodiment F1, F1.1 or F2, wherein the average length of a polynucleotide in the sample nucleic acid is less than about 300 base pairs.

F4. The method of embodiment F2 or F3, wherein the circulating, cell-free nucleic acid is from serum or plasma.

F5. The method of any one of embodiments F1 to F4, wherein the sequence reads have been mapped to a reference genome or portion thereof.

F6. The method of embodiment F5, comprising, prior to (a), identifying a subset of sequence reads for which all bases do not align with the reference genome or portion thereof, and performing (a), (b), (c) and (d) for the subset.

F7. The method of any one of embodiments F1 to F6, wherein the sequence reads are single-end sequence reads.

F7.1. The method of any one of embodiments F1 to F7, wherein the sequence reads are discordant reads.

F7.2. The method of embodiment F7.1, wherein the change in mappability is determined for the discordant reads.

F8. The method of any one of embodiments F1 to F6, wherein the sequence reads are paired-end sequence reads.

F9. The method of embodiments F8, wherein the sequence reads are discordant read pairs.

F10. The method of any one of embodiments F1 to F9, comprising identifying discordant read pairs thereby providing discordant read mates.

F10.1. The system of embodiment F10, wherein the change in mappability is determined for the discordant read mates.

F11. The method of any one of embodiments F1 to F10.1, wherein chimeric read pairs are not identified prior to (a).

F12. The method of any one of embodiments F1 to F11, comprising identifying a candidate breakpoint for each sequence read in the subset prior to the comparing in (c).

F13. The method of embodiment F12, wherein the candidate breakpoint for each sequence read is identified according to the change in the mappability.

F14. The method of embodiment F12 or F13, wherein the comparing in (c) comprises comparing (i) the number of each of the sequence reads in the subset identified in (b) from the sample associated with the candidate breakpoint, to (ii) the number of each of the sequence reads in the subset identified in (b) from a reference associated with the candidate breakpoint.

F15. The method of any one of embodiments F1 to F14, wherein the sequence reads have a minimum length of about 32 contiguous bases in the subset identified in (b).

F16. The method of any one of embodiments F12 to F15, wherein there are at least about 15 contiguous bases to about 20 contiguous bases on each side of the candidate breakpoint in each of the sequence reads in the subset identified in (b).

F17. The method of any one of embodiments F1 to F16, wherein the sequence reads are of nucleic acid fragments having an average, mean, median or maximum length of about 20 bases to about 500 bases.

F17.1. The method of embodiment F17, wherein the sequence reads are of nucleic acid fragments having an average, mean, median or maximum length of about 40 bases to about 500 bases.

F18. The method of any one of embodiments F1 to F17.1, wherein the one or more chromosome alterations comprise a chromosome translocation.

F18.1 The method of any one of embodiments F1 to F18, wherein the one or more chromosome alterations comprise a balanced chromosome translocation.

F19. The method of any one of embodiments F1 to F17, wherein the one or more chromosome alterations comprise a chromosome deletion.

F20. The method of any one of embodiments F1 to F17, wherein the one or more chromosome alterations comprise a chromosome inversion.

F21. The method of any one of embodiments F1 to F17, wherein the one or more chromosome alterations comprise a heterologous insertion.

F22. The method of any one of embodiments F1 to F21, comprising providing the position of one or more breakpoints in instances where the presence of the one or more chromosome alterations is determined in (d).

F23. The method of embodiment F22, wherein the position of each of the one or more breakpoints is provided with a one base pair resolution.

F24. The method of any one of embodiments F1 to F23, wherein the identifying in (b) comprises generating a fitted relationship between the mappability and the length of each of the sequence read subsequences of each of the reads.

F25. The method of embodiment F24, wherein the change in mappability is determined from a slope in the relationship.

F26. The method of any one of embodiments F1 to F25, wherein sequence reads, for which there is alignment of sequence read subsequences of increasing length to a first chromosome, followed by alignment to a second chromosome and then followed by alignment to the first chromosome, are not included in the subset identified in (b).

F26.1. The method of any one of embodiments F1 to F26, wherein sequence reads, for which there is alignment of sequence read subsequences of increasing length to a first chromosome, followed by alignment to a second chromosome are included in the subset identified in (b).

F27. The method of any one of embodiments F1 to F26.1, wherein the comparison in (c) is determined according to a z-score between the number of sequence reads in (c)(i) and the number of sequence reads in (c)(ii).

F28. The method of any one of embodiments F12 to F27, wherein each of the sequence reads in the subset identified in (b) comprises substantially similar candidate breakpoints.

F29. The method of any one of embodiments F1 to F28, wherein each of the sequence read subsequences of each read is shorter than the next largest fragment or the read by about 5 bases or less.

F30. The method of embodiment F29, wherein each of the sequence read subsequences of each read is shorter than the next largest fragment or the read by 1 base or 2 bases.

F31. The method of embodiment F30, wherein each of the sequence read subsequences of each read is incrementally shorter than the next largest fragment or the read.

F32. The method of embodiment F31, wherein each of the sequence read subsequences of each read is incrementally shorter than the next largest fragment or the read by about 1 base.

F33. The method of any one of embodiments F24 to F32, wherein the characterizing the mappability of a plurality of sequence read subsequences comprises determining a slope of the fitted relationship.

F34. The method of any one of embodiments F1 to F33, wherein the identifying in (b) is according to a mappability threshold.

F35. The method of any one of embodiments F1 to F34, comprising filtering reads.

F36. The method of embodiment F35, wherein the filtering comprises removing one or both of the discordant read mates.

F37. The method of embodiment F35 or F36, wherein the filtering is chosen from one or more of (i) removing low quality reads, (ii) removing concordant reads, (iii) removing PCR duplicated reads, (iv) removing reads mapped to mitochondrial DNA, (v) removing reads mapped to repetitive elements, (vi) removing unmappable reads, (vi) removing reads comprising step-wise multiple alignments and (vii) removing reads mapped to a centromere.

F38. The method of any one of embodiments F35 to F37, wherein the filtering comprises removing one or more singleton events.

F39. The method of any one of embodiments F35 to F38, wherein the filtering comprises removing the subset of reads identified in (b) in instances where the number of each of the sequence reads in the subset from the sample are substantially similar to the number of each of the sequence reads in the subset from the reference.

F40. The method of any one of embodiments F28 to F39, wherein the location of the candidate breakpoint is identified at a single base resolution.

F41. The method of any one of embodiments F1 to F40, wherein the presence of a balanced translocation is determined in (d).

F42. The method of any one of embodiments F1 to F41, wherein the presence of an unbalanced translocation is determined in (d).

F43. The method of any one of embodiments F1 to F42, wherein determining the presence of the chromosome alteration in (d) comprises identifying a substantially greater number of sequence reads from the sample compared to the reference in the comparison of (c).

F44. The method of any one of embodiments F1 to F43, wherein a breakpoint is identified according to the comparison in (c).

F45. The method of any one of embodiments F1 to F44, wherein a first breakpoint and a second breakpoint are identified according to the comparison in (c).

F46. The method of embodiment F45, wherein the presence of a chromosome alteration is identified in (d) according to the first and the second breakpoints.

F47. The method of any one of embodiments F1 to F46, wherein the comparison in (c) comprises determining a level of confidence.

F48. The method of embodiment F47, wherein determining the level of confidence comprises determining a p value.

F49. The method of embodiment F47, wherein determining the level of confidence comprises determining a Z-score.

F50. The method of any one of embodiments F1 to F49, wherein the memory comprises one or more of the sequence reads, the plurality of sequence read subsequences, the discordant read pairs, the subsets of reads, the candidate breakpoints, or a combination thereof.

F51. The method of any one of embodiments F1 to F50, wherein the sample nucleic acid is circulating cell-free nucleic acid from a pregnant female bearing a fetus.

F52. The method of any one of embodiments F1 to F50, wherein the sample nucleic acid is circulating cell-free nucleic acid from a subject having or suspected of having a cell proliferative disorder.

F53. The method of embodiment F52, wherein the cell proliferative disorder is cancer.

F54. The method of any one of embodiments F1 to F53, wherein the presence or absence of one or more chromosome alterations is determined for a minority nucleic acid species.

F55. The method of embodiment F54, wherein the minority nucleic acid species comprises fetal nucleic acid.

F56. The method of embodiment F54, wherein the minority nucleic acid species comprises nucleic acid from cancer cells.

G1. A non-transitory computer-readable storage medium with an executable program stored thereon, which program is configured to instruct a microprocessor to:
  (a) characterize mappability of a plurality of sequence read subsequences for sequence reads, wherein:
    there are multiple sequence read subsequences for each sequence read,
    the sequence read subsequences for each sequence read are of different lengths, and
    the sequence reads are of the sample nucleic acid;
  (b) identify a subset of sequence reads for which there is a change in mappability of one or more subsequences;
  (c) compare (i) the number of each of the sequence reads in the subset identified in (b) from the sample, to (ii) the number of each of the sequence reads in the subset identified in (b) from a reference, thereby generating a comparison; and
  (d) determine the presence or absence of one or more chromosome alterations for the sample according to the comparison in (c).

G2. The storage medium of embodiment G1, wherein the sequence reads are of circulating, cell-free nucleic acid.

G3. The storage medium of embodiment G1 or G2, wherein the sequence reads are discordant read pairs.

G4. The storage medium of any one of embodiments G1 to G3, wherein the program is configured to instruct a microprocessor to identify a candidate breakpoint for each sequence read in the subset.

G5. The storage medium of any one of embodiments G1 to G4, wherein the one or more chromosome alterations comprise a chromosome translocation.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed can be resorted to by those skilled in the art, and such modifications and variations are considered within the scope of this technology.

Certain embodiments of the technology are set forth in the claim(s) that follow(s).

What is claimed is:

1. A method for determining the presence or absence of one or more chromosome alterations in a test sample of nucleic acids, which method comprises:
   (a) obtaining sequence reads from high-throughput sequencing of the test sample of nucleic acids and a reference sample of nucleic acids;
   (b) generating a plurality of sequence read subsequences for each obtained sequence read for the test sample and a plurality of sequence read subsequences from each read for the reference sample,
   (c) aligning each of the sequence read subsequences to a reference genome to determine the mappability of the sequence read subsequence using a computer processor,
   (d) identifying a subset of the sequence reads for which there is a change in the mappability of one or more of the subsequences of each identified sequence read for the test sample and for the reference sample;
   (e) comparing (i) the number of each of the sequence reads in the subset identified in (d) from the test sample, to (ii) the number of each of the sequence reads in the subset identified in (d) from the reference sample, thereby generating a comparison; and
   (f) determining the presence or absence of one or more chromosome alterations for the sample according to the comparison in (e).

SEQUENCE LISTING

<160> NUMBER OF SEQ ID NOS: 4

<210> SEQ ID NO 1
<211> LENGTH: 50
<212> TYPE: DNA
<213> ORGANISM: Homo sapiens

<400> SEQUENCE: 1
cagattgaga gtcgatccac agacagccta gcagagcaat ccaagagtaa            50

<210> SEQ ID NO 2
<211> LENGTH: 50
<212> TYPE: DNA
<213> ORGANISM: Homo sapiens

<400> SEQUENCE: 2
cagattgaga gtcgatccac agacaagggc ggggctgggt tttagccgta            50

<210> SEQ ID NO 3
<211> LENGTH: 50
<212> TYPE: DNA
<213> ORGANISM: Homo sapiens

<400> SEQUENCE: 3
acaactggag gatctgggcg cctcgagggc ggggctgggt tttagccgta            50

<210> SEQ ID NO 4
<211> LENGTH: 44
<212> TYPE: DNA
<213> ORGANISM: Homo sapiens

<400> SEQUENCE: 4
acaactggag gatctgggcg cctagcagag caatccaaga gtaa                  44

2. The method of claim 1, wherein the sequence reads have been mapped to a reference genome or a portion thereof, and wherein the method comprises, prior to (b), identifying a subset of sequence reads for which all bases do not align with the reference genome or portion thereof, and performing (b), (c), (d), (e), and (f) for the subset of sequence reads.

3. The method of claim 1, wherein the sequence reads are single-end sequence reads, the sequence reads are discordant reads, and the change in mappability is determined for the discordant reads.

4. The method of claim 1, wherein the sequence reads are paired-end sequence reads and the sequence reads are discordant read pairs.

5. The method of claim 1, wherein the method comprises identifying discordant read pairs thereby providing discordant read mates, and wherein the change in mappability in (d) is determined for the discordant read mates.

6. The method of claim 1, comprising identifying a candidate breakpoint for each sequence read in the subset prior to the comparing in (e), wherein the candidate breakpoint for each sequence read is identified according to the change in the mappability.

7. The method of claim 6, wherein the comparing in (e) comprises comparing (i) the number of each of the sequence reads in the subset identified in (d) from the sample associated with the candidate breakpoint, to (ii) the number of each of the sequence reads in the subset identified in (d) from the reference sample associated with the candidate breakpoint.

8. The method of claim 1, wherein the identifying in (d) comprises generating a fitted relationship between the mappability and the length of each of the sequence read subsequences of each of the reads, and wherein the change in mappability of the sequence reads subsequence is determined from a slope in the relationship.

9. The method of claim 1, wherein the comparison in (e) is determined according to a z-score between the number of sequence reads in (e)(i) and the number of sequence reads in (e)(ii).

10. The method of claim 1, wherein determining the presence of the one or more chromosome alterations in (f) comprises identifying a substantially greater number of sequence reads from the test sample compared to the reference sample in the comparison of (e).

11. The method of claim 1, wherein a breakpoint is identified according to the comparison in (e).

12. The method of claim 1, wherein a first breakpoint and a second breakpoint are identified according to the comparison in (e), and wherein the presence of a chromosome alteration is identified in (f) according to the first and the second breakpoints.

13. The method of claim 1, comprising filtering the sequence reads.

14. The method of claim 13, wherein the filtering is chosen from one or more of (i) removing low quality reads, (ii) removing concordant reads, (iii) removing PCR duplicated reads, (iv) removing reads mapped to mitochondrial DNA, (v) removing reads mapped to repetitive elements, (vi) removing unmappable reads, (vi) removing reads comprising stepwise multiple alignments, and (vii) removing reads mapped to a centromere.

15. The method of claim 13, wherein the filtering comprises removing one or more singleton events.

16. The method of claim 13, wherein the filtering comprises removing the subset of reads identified in (d) in instances where the number of each of the sequence reads in the subset from the sample are substantially similar to the number of each of the sequence reads in the subset from the reference.

17. The method of claim 5, comprising filtering reads, wherein the filtering comprises removing one or both of the discordant read mates provided from each identified read pair.

18. The method of claim 1, wherein the sequence reads are of circulating, cellfree nucleic acids.

19. The method of claim 18, wherein the circulating, cell-free nucleic acids are from serum or plasma.

20. The method of claim 1, wherein the one or more chromosome alterations comprise one or more of a chromosome translocation, a balanced chromosome translocation, a chromosome deletion, a chromosome inversion, and a heterologous insertion.

* * * * *